(12) United States Patent
Radu et al.

(10) Patent No.: US 10,586,929 B2
(45) Date of Patent: Mar. 10, 2020

(54) SOLVENT-RESISTANT HOLE TRANSPORT LAYERS

(71) Applicant: LG Chem, Ltd., Seoul (KR)

(72) Inventors: Nora Sabina Radu, Landenberg, PA (US); Adam Fennimore, Wilmington, DE (US)

(73) Assignee: LG Chem, Ltd. (KR)

( * ) Notice: Subject to any disclaimer, the term of this patent is extended or adjusted under 35 U.S.C. 154(b) by 650 days.

(21) Appl. No.: 15/101,133

(22) PCT Filed: Dec. 9, 2014

(86) PCT No.: PCT/US2014/069273
§ 371 (c)(1),
(2) Date: Jun. 2, 2016

(87) PCT Pub. No.: WO2015/089027
PCT Pub. Date: Jun. 18, 2015

(65) Prior Publication Data
US 2016/0308141 A1 Oct. 20, 2016

Related U.S. Application Data

(60) Provisional application No. 61/915,132, filed on Dec. 12, 2013.

(51) Int. Cl.
*H01L 51/00* (2006.01)
*C07D 327/06* (2006.01)
(Continued)

(52) U.S. Cl.
CPC ........ *H01L 51/0071* (2013.01); *C07D 327/06* (2013.01); *C07D 333/72* (2013.01);
(Continued)

(58) Field of Classification Search
CPC . C07D 333/72; C07D 327/06; H01L 51/5088; H01L 51/0036; H01L 51/5056
See application file for complete search history.

(56) References Cited

U.S. PATENT DOCUMENTS 5,871,876 A 2/1999 Ikuno et al.
6,670,645 B2 12/2003 Grushin et al.
(Continued)

FOREIGN PATENT DOCUMENTS

WO 2003/008424 A1 1/2003
WO 2003/040257 A1 5/2003
(Continued)

OTHER PUBLICATIONS

Croce, et al., Macromolecules, 2007, vol. 40, pp. 6028-6031 (Year: 2007).*
(Continued)

*Primary Examiner* — Sadie White
(74) *Attorney, Agent, or Firm* — Lerner, David, Littenberg, Krumholz & Mentlik, LLP

(57) ABSTRACT

There is provided a hole transport material having Formula I, Formula Ia, or Formula II: In the formulae: A is an aromatic moiety including at least one triarylamino group; B' is an aromatic moiety; E is an end group which is H, D, alkyl, aryl, halide, deuterated alkyl, or deuterated aryl; G is G1, G2, or a deuterated analog thereof where the asterisk represents the point of attachment; n is an integer greater than 0; and m1 and m2 represent non-zero mole fractions, such that $m1+m2=1$.

15 Claims, 2 Drawing Sheets

(51) Int. Cl.
*C08G 61/10* (2006.01)
*C08G 73/02* (2006.01)
*C07D 333/72* (2006.01)
*C08G 61/12* (2006.01)
*H01L 51/50* (2006.01)
*H01L 51/56* (2006.01)

(52) U.S. Cl.
CPC ............. *C08G 61/10* (2013.01); *C08G 61/12* (2013.01); *C08G 73/026* (2013.01); *H01L 51/0035* (2013.01); *H01L 51/0043* (2013.01); *C08G 2261/12* (2013.01); *C08G 2261/145* (2013.01); *C08G 2261/148* (2013.01); *C08G 2261/149* (2013.01); *C08G 2261/1412* (2013.01); *C08G 2261/1644* (2013.01); *C08G 2261/312* (2013.01); *C08G 2261/3162* (2013.01); *C08G 2261/412* (2013.01); *C08G 2261/512* (2013.01); *C08G 2261/95* (2013.01); *H01L 51/0003* (2013.01); *H01L 51/5056* (2013.01); *H01L 51/5064* (2013.01); *H01L 51/56* (2013.01)

(56) References Cited

U.S. PATENT DOCUMENTS

| | | | | |
|---|---|---|---|---|
| 2007/0096082 | A1* | 5/2007 | Gaynor | C07C 211/60 257/40 |
| 2009/0227765 | A1* | 9/2009 | Towns | C08G 73/02 528/422 |
| 2010/0045174 | A1* | 2/2010 | Okabe | C08G 65/18 313/504 |
| 2011/0062390 | A1* | 3/2011 | Cardona | B82Y 10/00 252/519.2 |

FOREIGN PATENT DOCUMENTS

| | | |
|---|---|---|
| WO | 2003/063555 A1 | 7/2003 |
| WO | 2003/091688 A2 | 11/2003 |
| WO | 2004/016710 A1 | 2/2004 |
| WO | 2005/052027 A1 | 6/2005 |

OTHER PUBLICATIONS

Wang, Y., Kirk-Othmer Encyclopedia of Chemical Technology, Fourth Edition, vol. 18, 1996, (Book Not Included).

Tashbaev, G.A., "Reactions of 1,3-dihydrobenzo[c]thiophene 2,2-dioxides with electrophilic agents," Russian Chemical Bulletin, International Edition, 2005, vol. 54, No. 2, pp. 437-440.

Tang, Kuo-Chun et al., "Photochemistry and photodissociation of benzosultine and naphthosultine: electronic relaxation of sultine and kinetics and theoretical studies of fragment o-quinodimethanes", Journal of Photochemistry and Photobiology A: Chemistry, 2005, vol. 170, pp. 69-81.

PCT International Search Report for Application No. PCT/US2014/069273, Han Jung Hee, Authorized Officer, ISA/KR; dated Mar. 23, 2015.

Gustafsson, G. et al. "Flexible light-emitting diodes made from soluble conducting polymers" Letters to Nature, vol. 357, Jun. 11, 1992, pp. 477-479.

CRC Handbook of Chemistry and Physics, 81st Edition, 2000-2001 (Book Not Included).

* cited by examiner

SOLVENT-RESISTANT HOLE TRANSPORT LAYERS

BACKGROUND INFORMATION

Field of the Disclosure

The present disclosure relates to novel hole transport materials and layers made therefrom. The disclosure further relates to electronic devices having at least one novel hole transport layer.

Description of the Related Art

In organic electronic devices, such as organic light emitting diodes ("OLED"), that make up OLED displays, an organic active layer is sandwiched between two electrical contact layers. In an OLED the organic layer emits light through the light-transmitting electrical contact layer upon application of a voltage across the electrical contact layers.

It is well known to use organic electroluminescent compounds as the photoactive component in light-emitting diodes. Simple organic molecules, conjugated polymers, and organometallic complexes have been used. Devices that use electroluminescent materials frequently include one or more added electroactive layers, which are positioned between the electroluminescent layer and a contact layer. A hole transport layer can be positioned between the electroluminescent layer and the hole-injecting contact layer. The hole-injecting contact layer may also be called the anode. An electron transport layer can be positioned between the electroluminescent layer and the electron-injecting contact layer. The electron-injecting contact layer may also be called the cathode.

There is a continuing need for hole transport materials for use in electronic devices.

SUMMARY

There is provided a hole transport material having Formula I, Formula Ia, or Formula II:

(I)

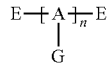
(Ia)

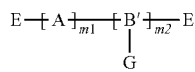
(II)

wherein:
- A is an aromatic moiety including at least one triarylamino group;
- B' is an aromatic moiety;
- E is the same or different at each occurrence and is an end group selected from the group consisting of H, D, halide, alkyl, aryl, deuterated alkyl, and deuterated aryl;
- G is selected from the group consisting of G1, G2, and deuterated analogs thereof

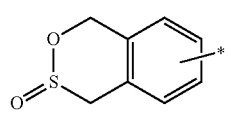
G1

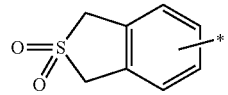
G2 where the asterisk represents the point of attachment;
n is an integer greater than 0;
m1 and m2 represent non-zero mole fractions, such that m1+m2=1.

There is also provided hole transport material comprising:
(a) a material having at least one triarylamino group; and
(b) a material having Formula III, Formula IIIa, or Formula IV:

(III)

(IIIa)

(IV)

wherein:
- J is an aromatic moiety;
- K is selected from the group consisting of alkyl, aryl, substituted derivatives thereof, and deuterated analogs thereof;
- M is selected from the group consisting of alkyl, aryl, substituted derivatives thereof, and deuterated analogs thereof;
- E is the same or different at each occurrence and is an end group selected from the group consisting of H, D, halide, alkyl, aryl, deuterated alkyl, and deuterated aryl.
- G is selected from the group consisting of G1, G2, and deuterated analogs thereof

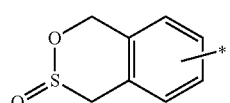
G1

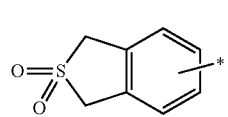
G2 where the asterisk represents the point of attachment;
n is an integer greater than 0;
s1 and s2 represent mole fractions, such that s2≠0 and s1+s2=1.

There is also provided a process for making a hole transport layer from the above material.

There is also provided an electronic device having the above hole transport layer.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
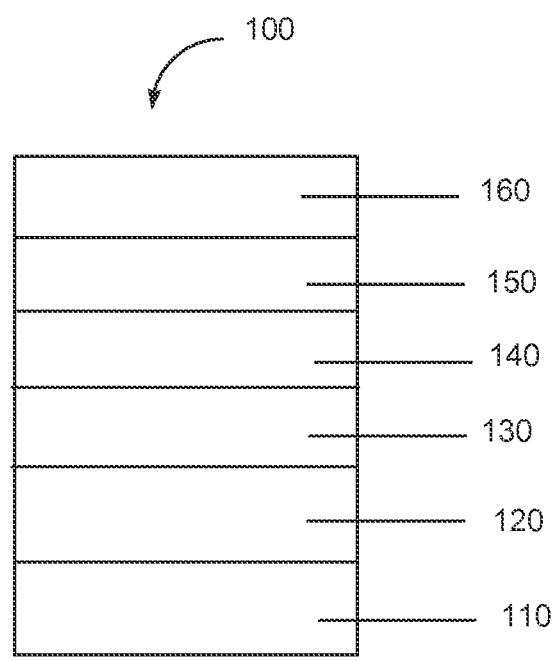
FIG. 1 includes an illustration of one example of an organic electronic device.

Skilled artisans appreciate that objects in the figures are illustrated for simplicity and clarity and have no necessarily been drawn to scale. For example, the dimensions of some of the objects in the figures may be exaggerated relative to other objects to help to improve understanding of embodiments.

DETAILED DESCRIPTION

There is provided a hole transport material having Formula I, Formula Ia, or Formula II:

  (I)

  (Ia)

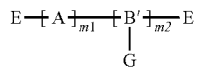  (II)

wherein:
- A is an aromatic moiety including at east one triarylamino group;
- B' is an aromatic moiety;
- E is the same or different at each occurrence and is an end group selected from the group consisting of H, D, halide, alkyl, aryl, deuterated alkyl, and deuterated aryl;
- G is selected from the group consisting of G1, G2, and deuterated analogs thereof

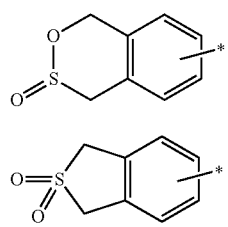

where the asterisk represents the point of attachment;
n is an integer greater than 0;
m1 and m2 represent non-zero mole fractions, such that m1+m2=1.

There is also provided hole transport material comprising:
(a) a material having at least one triarylamino group; and
(b) a material having Formula III, Formula IIIa, or Formula IV:

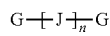  (III)

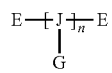  (IIIa)

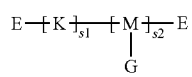  (IV)

wherein:
- J is an aromatic moiety;
- K is selected from the group consisting of alkyl, aryl, substituted derivatives thereof, and deuterated analogs thereof;
- M is selected from the group consisting of alkyl, aryl, substituted derivatives thereof, and deuterated analogs thereof;
- E is the same or different at each occurrence and is an end group selected from the group consisting of H, D, halide, alkyl, aryl, deuterated alkyl, and deuterated aryl;
- G is selected from the group consisting of G1, G2, and deuterated analogs thereof

G1

G2 where the asterisk represents the point of attachment;
n is an integer greater than 0;
s1 and s2 represent mole fractions, such that s2≠0 and s1+s2=1.

There is also provided a process for making a hole transport layer from any of the above hole transport materials.

There is also provided an electronic device having any of the above hole transport layers.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Hole Transport Material, the Process, the Electronic Device, and finally Examples.

1. Definitions and Clarification of Terms

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "alkoxy" is intended to mean the group —$OR^a$, where $R^a$ is alkyl.

The term "aromatic" refers to a compound or group having at least one unsaturated cyclic group having delocalized pi electrons. The aromatic ring has 4n+2 pi electrons and is essentially planar.

The term "aryl" means an aromatic carbocyclic moiety, which may be a single ring (monocyclic) or multiple rings (bicyclic, or more) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 60 carbon atoms; in some embodiments. 6 to 30 carbon atoms. The term is intended to include heteroaryl groups. Heteroaryl groups may have from 4-50 carbon atoms; in some embodiments, 4-30 carbon atoms.

The term "aryloxy" is intended to mean the group —$OR^a$, where $R^a$ is aryl.

The term "bake" and its verb variants refers to the process of exposing a material, member, or structure to a heated environment. The bake temperature is the temperature of the environment. The material, member, or structure may or may not reach the bake temperature.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "electroactive" as it refers to a layer or a material, is intended to indicate a layer or material which electronically facilitates the operation of the device. Examples of active materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The prefix "hetero" indicates that one or more carbon atoms has been replaced with a different atom. In some embodiments, the heteroatom is O, N, S, or combinations thereof.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "liquid medium" is intended to mean a liquid material, including a pure liquid and a combination of liquids. Liquid medium is used in the singular, regardless of whether one or more solvents are present.

The term "photoactive" is intended to mean a material that emits light when activated by an applied voltage (such as in a light emitting diode or chemical cell) or responds to radiant energy and generates a signal with or without an applied bias voltage (such as in a photodetector or a photovoltaic cell).

The term "polymer" is intended to mean a material having at least one repeating monomeric unit. The term includes homopolymers having only one kind of monomeric unit, and copolymers having two or more different monomeric units. Copolymers are a subset of polymers. In some embodiments, a polymer has at least 5 repeating units; in some embodiments, at least 10 repeating units; in some embodiments, at least 20 repeating units. In some embodiments, a polymer has a weight average molecular weight greater than 10,000. In some embodiments, a polymer has a weight average molecular weight greater than 50,000. In some embodiments, a polymer has a weight average molecular weight greater than 100,000.

The term "silyl" refers to the group $(R^d)_3Si$—, where $R^d$ is H, D, C1-20 alkyl, fluoroalkyl, or aryl. In some embodiments, one or more carbons in an $R^a$ alkyl group are replaced with Si. In some embodiments, the silyl groups are $(hexyl)_2Si(Me)CH_2CH_2Si(Me)_2$- and $[CF_3(CF_2)_6CH_2CH_2]_2SiMe$-.

The term "siloxane" refers to the group $(R^aO)_3Si$—, where $R^a$ is H, D, C1-20 alkyl, or fluoroalkyl.

The term "workpiece" is intended to mean a substrate at any particular point of a process sequence. Note that the substrate may not significantly change during a process sequence, whereas the workpiece significantly changes during the process sequence. For example, at a beginning of a process sequence, the substrate and workpiece are the same. After a layer is formed over the substrate, the substrate has not changed, but now the workpiece includes the substrate and the layer.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

Unless otherwise indicated, all groups can be unsubstituted or substituted. In some embodiments, the substituents are selected from the group consisting of deuterium, halide, alkyl, alkoxy, aryl, amino, silyl, and cyano.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Hole Transport Material (i) Formula I

In some embodiments, the hole transport material has Formula I:

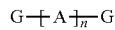
(I)

wherein:
A is an aromatic moiety including at least one triarylamino group;
G is selected from the group consisting of G1, G2, and deuterated analogs thereof

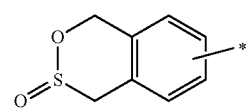
G1

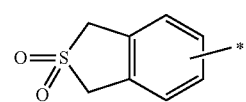
G2 where the asterisk represents the point of attachment; and n is an integer greater than 0.

As used in the formulae and structures herein, the asterisk indicates the point of attachment.

In some embodiments, G1 is G1-a

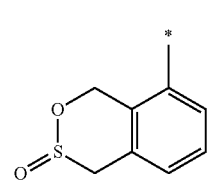
G1-a

In some embodiments, G1 is G1-b

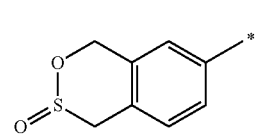
G1-b

In some embodiments, G1 is G1-c

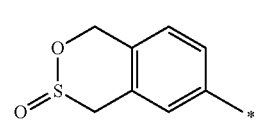
G1-c

In some embodiments, G1 is G1-d

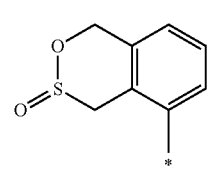
G1-d

In some embodiments, G1 is a mixture of two or more of G1-a, G1-b, G1-c, and G1-d.

In some embodiments, G1 is a mixture of G1-b and G1-c.

In some embodiments, G2 is G2-a

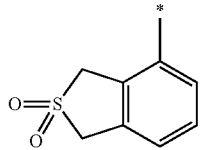

G2-a

In some embodiments, G2 is G2-b

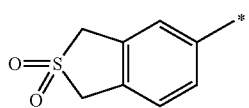

G2-b

In some embodiments, G2 is a mixture of G2-a and G2-b.

In some embodiments, the material having Formula I is a small molecule with n=1.

In some embodiments, the material having Formula I is an oligomer with n=2-5.

In some embodiments, the material having Formula I is a polymer with n>5. In some embodiments, the polymer has a weight average molecular weight, $M_w$>20,000; in some embodiments, $M_w$>50,000; in some embodiments, $M_w$>100,000.

In some embodiments, the material having Formula I is deuterated. The term "deuterated" is intended to mean that at least one H has been replaced by D. The term "deuterated analog" refers to a structural analog of a compound or group in which one or more available hydrogens have been replaced with deuterium. In a deuterated compound or deuterated analog, the deuterium is present in at least 100 times the natural abundance level. In some embodiments, the compound is at least 10% deuterated. By "% deuterated" or "% deuteration" is meant the ratio of deuterons to the sum of protons plus deuterons, expressed as a percentage. In some embodiments, the material is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

The G group in Formula I can be bonded directly to an aromatic ring of group A, or it can be bonded to a substituent group on an aromatic ring of group A.

In some embodiments, group G is bonded to an alkyl substituent on group A.

In some embodiments of Formula I, group A has formula A-1

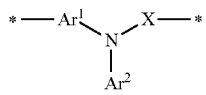

A-1 wherein:

Ar¹-Ar² are the same or different and are aryl groups; and

X is the same or different at each occurrence and is selected from a single bond, an aryl group, and a deuterated aryl group, with the proviso that N is not bonded directly to G.

In some embodiments of formula A-1, Ar¹ and Ar² are selected from the group consisting of phenyl, naphthyl, anthracenyl, carbazolyl, combinations of such groups linked together covalently, and deuterated analogs thereof.

In some embodiments of formula A-1, X is aryl.

In some embodiments of formula A-1, X is selected from the group consisting of phenyl, naphthyl, anthracenyl, combinations of such groups linked together covalently, and deuterated analogs thereof.

In some embodiments of Formula I, group A has formula A-2:

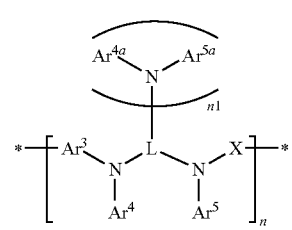

A-2 wherein:

Ar³, Ar⁴, Ar⁴ᵃ, Ar⁵ and Ar⁵ᵃ are the same or different and are aryl groups;

L is the same or different at each occurrence and is aryl, (CR'₂)_q, adamantyl, bicyclic cyclohexyl, or a bicyclic group having aliphatic rings connected through a single atom;

R' is the same or different at each occurrence and is H, D, alkyl, fluoroalkyl, aryl, deuterated alkyl, deuterated fluoroalkyl, and deuterated aryl;

X is the same or different at each occurrence and is selected from a single bond, an aryl group, and a deuterated aryl group, with the proviso that N is not bonded directly to G;

n1 is 0 or 1; and q is an integer from 1-5.

In some embodiments of formula A-2, Ar³, Ar⁴, Ar⁴ᵃ, Ar⁵ and Ar⁵ᵃ are selected from the group consisting of phenyl, naphthyl, anthracenyl, carbazolyl, combinations of such groups linked together covalently, and deuterated analogs thereof.

In some embodiments of formula A-2, X is aryl.

In some embodiments of formula A-2, X is selected from the group consisting of phenyl, naphthyl, anthracenyl, combinations of such groups linked together covalently, and deuterated analogs thereof.

In some embodiments of Formula I, group A has formula A-3

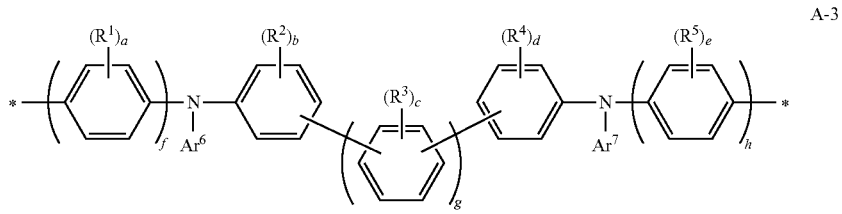

wherein:
- $Ar^6$ and $Ar^7$ are the same or different and are aryl groups;
- $R^1$ through $R^5$ are independently the same or different at each occurrence and are selected from the group consisting of D, F, alkyl, aryl, alkoxy, silyl, deuterated alkyl, deuterated aryl, deuterated alkoxy, and deuterated silyl;
- a through e are independently an integer from 0 to 4;
- f is 1 or 2;
- g is 0, 1 or 2; and
- h is 1 or 2; and
- n is an integer greater than 0.

In some embodiments of formula A-3, $Ar^6$ and $Ar^7$ are aryl groups having no fused rings.

In some embodiments of formula A-3, $Ar^6$ and $Ar^7$ have Formula x

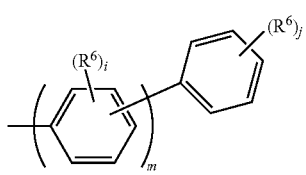

where:
- $R^6$ is the same or different at each occurrence and is selected from the group consisting of D, alkyl, alkoxy, siloxane, silyl, deuterated alkyl, deuterated alkoxy, deuterated siloxane, and deuterated silyl;
- i is the same or different at each occurrence and is an integer from 0-4;
- j is an integer from 0-5; and
- m is an integer from 1 to 5.

In some embodiments of formula A-3, $Ar^6$ and $Ar^7$ have Formula y

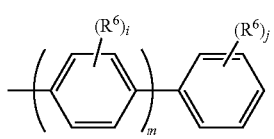

where:
- $R^6$ is the same or different at each occurrence and is selected from the group consisting of D, alkyl, alkoxy, siloxane and silyl;
- i is the same or different at each occurrence and is an integer from 0-4;
- j is an integer from 0-5; and
- m is an integer from 1 to 5.

In some embodiments of Formulae x and y, at least one of i and j is not zero. In some embodiments, m=1-3.

In some embodiments of formula A-3, $Ar^6$ and $Ar^7$ are selected from the group consisting of phenyl, biphenyl, terphenyl, deuterated analogs thereof, and derivatives thereof having one or more substituents selected from the group consisting of alkyl, alkoxy, and silyl.

In some embodiments of Formula A-3, $R^1$ through $R^5$ are D or $C_{1-10}$ alkyl. In some embodiments, the alkyl group is deuterated.

In some embodiments of formula A-3, a=e=0. In some embodiments of formula A-3, a=e=4 and $R^1$ and $R^5$ are D.

In some embodiments of formula A-3, b>0 and at least one $R^2$ is alkyl. In some embodiments of formula A-3, the alkyl group is deuterated.

In some embodiments of formula A-3, b=4, one $R^2$ is alkyl and the remainder are D.

In some embodiments of formula A-3, c>0 and at least one $R^3$ is alkyl. In some embodiments of formula A-3, the alkyl group is deuterated. In some embodiments of formula A-3, c=4, one $R^3$ is alkyl and the remainder are D. In some embodiments of formula A-3, c=4, two $R^3$ are alkyl and two $R^3$ are D.

In some embodiments of formula A-3, d>0 and at least one $R^4$ is alkyl. In some embodiments of formula A-3, the alkyl group is deuterated. In some embodiments of formula A-3, d=4, one $R^4$ is alkyl and the remainder are D.

In some embodiments of formula A-3, f=h=2.
In some embodiments of formula A-3, g=1.
In some embodiments of Formula I, A has formula A-4

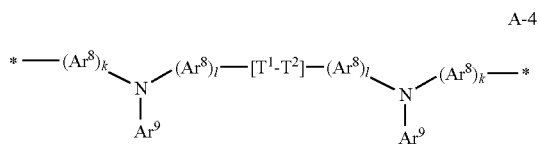

wherein:
- $Ar^8$ is the same or different at each occurrence and is selected from the group consisting of phenylene, substituted phenylene, naphthylene, substituted naphthylene, and deuterated analogs thereof;
- $Ar^9$ is the same or different at each occurrence and is an aryl group;
- $T^1$ and $T^2$ are independently the same or different at each occurrence and are conjugated moieties which are connected in a non-planar configuration;
- k is the same or different at each occurrence and is an integer from 1 to 6; and l is the same or different at each occurrence and is an integer from 1 to 6;

In some embodiments of formula A-4, at least one $Ar^8$ is a substituted phenyl with a substituent selected from the group consisting of alkyl, alkoxy, silyl, and deuterated analogs thereof.

In some embodiments of formula A-4, k is 1-4.

In some embodiments of formula A-4, k is 1-3.

In some embodiments of formula A-4, k=1.

In some embodiments of formula A-4, l is 1-3. In some embodiments l is 1-2.

In some embodiments of formula A-4, l is 1.

In some embodiments of formula A-4, $Ar^9$ has formula x, as defined above.

In some embodiments of formula A-4, $Ar^9$ has formula y, as defined above.

In some embodiments of formula A-4, $Ar^9$ is selected from the group consisting of a group having Formula a, naphthyl, phenylnaphthyl, naphthylphenyl, and deuterated analogs thereof.

In some embodiments of formula A-4, $Ar^9$ is selected from the group consisting phenyl, p-biphenyl, p-terphenyl, naphthyl, phenylnaphthyl, naphthylphenyl, and deuterated analogs thereof.

In some embodiments of formula A-4, $Ar^9$ is selected from the group consisting of phenyl, biphenyl, terphenyl, and deuterated analogs thereof.

Any of the aromatic rings in formula A-4 may be substituted at any position. The substituents may be present to improve one or more physical properties of the compound, such as solubility. In some embodiments, the substituents are selected from the group consisting of $C_{1-12}$ alkyl groups, $C_{1-12}$ alkoxy groups, silyl groups, and deuterated analogs thereof. In some embodiments, the alkyl groups are heteroalkyl groups. In some embodiments, the alkyl groups are fluoroalkyl groups.

In some embodiments of formula A-4, at least one $Ar^9$ has a substituent selected from the group consisting of alkyl, alkoxy, silyl, and deuterated analogs thereof.

The $T^1$-$T^2$ group introduces non-planarity into the backbone of the A-4 group. The moiety in $T^1$ that is directly linked to a moiety in $T^2$ is linked such that the $T^1$ moiety is oriented in a plane that is different from the moiety in $T^2$ to which it is linked. Although other parts of the $T^1$ unit, for example, substituents, may lie in one or more different planes, it is the plane of the linking moiety in $T^1$ and the linking moiety in $T^2$ in the compound backbone that provide the non-planarity. Because of the non-planar $T^1$-$T^2$ linkage, the compounds are chiral. In general, they are formed as racemic mixtures. The compounds can also be in enantiomerically pure form. The non-planarity can be viewed as the restriction to free rotation about the $T^1$-$T^2$ bond. Rotation about that bond leads to racemization. The half-life of racemization for $T^1$-$T^2$ is greater than that for an unsubstituted biphenyl. In some embodiments, the half-life or racemization is 12 hours or greater at 20° C.

In formula A-4, $T^1$ and $T^2$ are conjugated moieties. In some embodiments. $T^1$ and $T^2$ are aromatic moieties.

In some embodiments of formula A-4, $T^1$ and $T^2$ are selected from the group consisting of phenylene, napthylene, and anthracenyl groups.

In some embodiments of formula A-4, [$T^1$-$T^2$] is a substituted biphenylene group. The term "biphenylene" is intended to mean a biphenyl group having two points of attachment to the compound backbone. The term "biphenyl" is intended to mean a group having two phenyl units joined by a single bond. The biphenylene group can be attached at one of the 2, 3-, 4-, or 5-positions and one of the 2', 3'-, 4'-, or 5'-positions. The substituted biphenylene group has at least one substituent in the 2-position. In some embodiments of formula A-4, the biphenylene group has substituents in at least the 2- and 2'-positions.

In some embodiments of formula A-4, [$T^1$-$T^2$] is a binaphthylene group. The term "binaphthylene" is intended to mean a binapthyl group having 2 points of attachment to the compound backbone. The term "binaphthyl" is intended to mean a group having two naphthalene units joined by a single bond. In some embodiments, the binaphthylene group is a 1,1'-binaphthylene, which is attached to the compound backbone at one of the 3-, 4-, 5-, 6, or 7-positions and one of the 3'-, 4'-, 5'-, 6', or 7'-positions. This is illustrated below, where the dashed lines represent possible points of attachment.

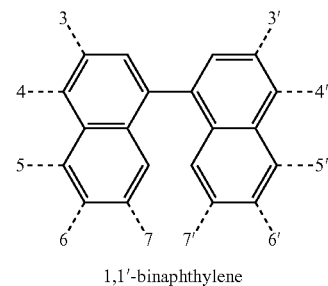

1,1'-binaphthylene

In some embodiments, the binaphthylene group is a 1,2'-binaphthylene having at least one substituent at the 8- or 9'-position, and which is attached to the compound backbone at one of the 3-, 4-, 5-, 6, or 7-positions and one of the 4'-, 5'-, 6'-, 7', or 8'-positions. This is illustrated below, where the dashed lines represent possible points of attachment and at least one R represents a substituent.

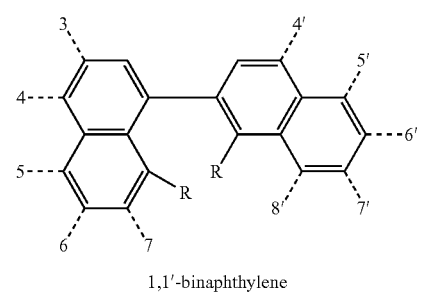

1,1'-binaphthylene

In some embodiments, the binaphthylene group is a 2,2'-binaphthylene having at least one substituent at the 8- or 9'-position, and which is attached to the compound backbone at one of the 4-, 5-, 6-, 7, or 8-positions and one of the 4'-, 5'-, 6'-, 7', or 8'-positions. This is illustrated below, where the dashed lines represent possible points of attachment and at least one R represents a substituent.

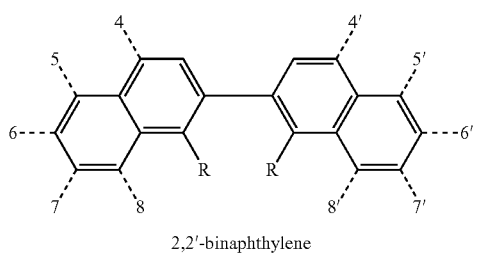

2,2′-binaphthylene

In some embodiments of formula A-4, [T¹-T²] is a phenylene-naphthylene group.

In some embodiments of formula A-4, [T¹-T²] is a phenylene-1-naphthylene group, which is attached to the compound backbone at one of the 3-, 4-, or 5-positions in the phenylene and one of the 3-, 4-, or 5-positions of the naphthylene.

In some embodiments of formula A-4, [T¹-T²] is a phenylene-2-naphthylene group, which is attached to the compound backbone at one of the 3-, 4-, or 5-positions in the phenylene and one of the 4-, 5-, 6-, 7-, or 8-positions of the naphthylene.

In some embodiments of formula A-4, the biphenylene, binaphthylene, and phenylene-naphthylene groups are substituted at one or more positions.

In some embodiments of formula A-4, [T¹-T²] is selected from one of the following:

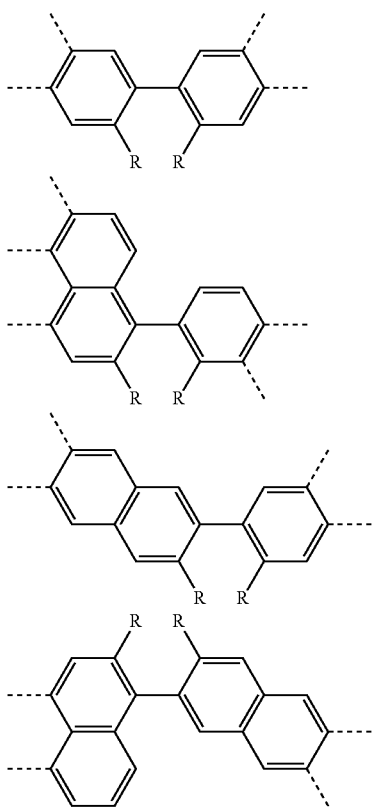

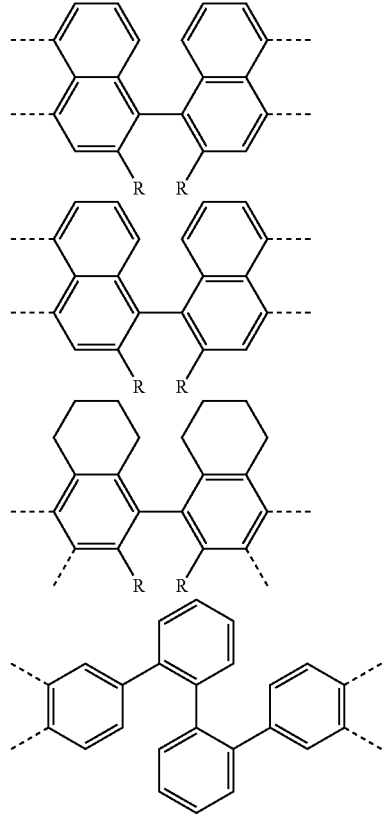

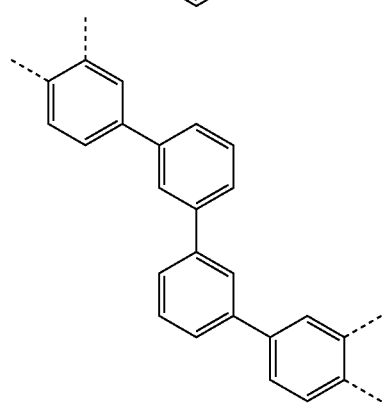

where R is the same or different and is selected from the group consisting of alkyl, aryl, alkoxy, aryloxy, fluoroalkyl, fluoroaryl, fluoroaryloxy fluoroalkyloxy, oxyalkyl, alkenyl groups, silyl, siloxane, and deuterated analogs thereof. The dashed line represents a possible point of attachment to the group backbone. In some embodiments, R is a $C_{1-10}$ alkyl or alkoxy, or deuterated analog thereof; in some embodiments, a $C_{3-8}$ branched alkyl or alkoxy, or deuterated analog thereof. In some embodiments, the two R groups are joined together to form a non-aromatic ring.

In some embodiments of formula A-4, [T¹-T²] is a 1,1-binaphthylene group which is attached to the group backbone at the 4 and 4′ positions, referred to as 4,4′-(1,1-binaphthylene).

In some embodiments of formula A-4, the 4,4′-(1,1-binaphthylene) is the only isomer present.

In some embodiments of formula A-4, two or more isomers are present.

In some embodiments of formula A-4, the 4,4'-(1,1-binaphthylene) is present with up to 50% by weight of a second isomer.

In some embodiments of formula A-4, the second isomer is selected from the group consisting of 4,5'-(1,1-binaphthylene), 4,6'-(1,1-binaphthylene), and 4,7'-(1,1-binaphthylene).

Any of the above embodiments for Formula I can be combined with one or more of the other embodiments, so long as they are not mutually exclusive. For example, the embodiment in which the material is deuterated can be combined with the embodiment where n=1 and the A group has formula A-1. The same is true for the other non-mutually-exclusive embodiments discussed above. The skilled person would understand which embodiments were mutually exclusive and would thus readily be able to determine the combinations of embodiments that are contemplated by the present application.

The monomeric, oligomeric, and polymeric materials having Formula I can be made using any technique that will yield a C—C or C—N bond. A variety of such techniques are known, such as Suzuki, Yamamoto, Stille, and Pd- or Ni-catalyzed C—N couplings. Deuterated compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum dichloride. Exemplary preparations are given in the Examples.

Some non-limiting examples of materials having Formula I include the following:

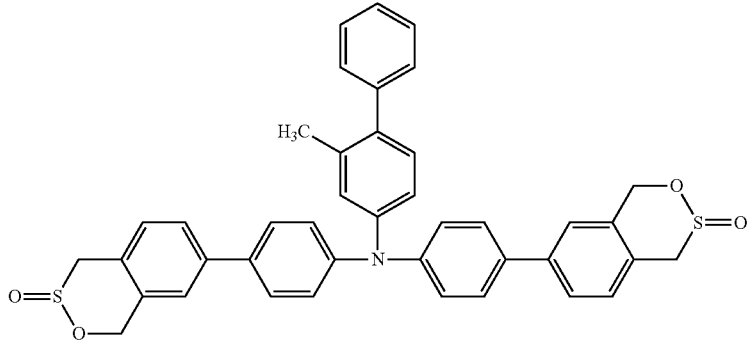

HT1

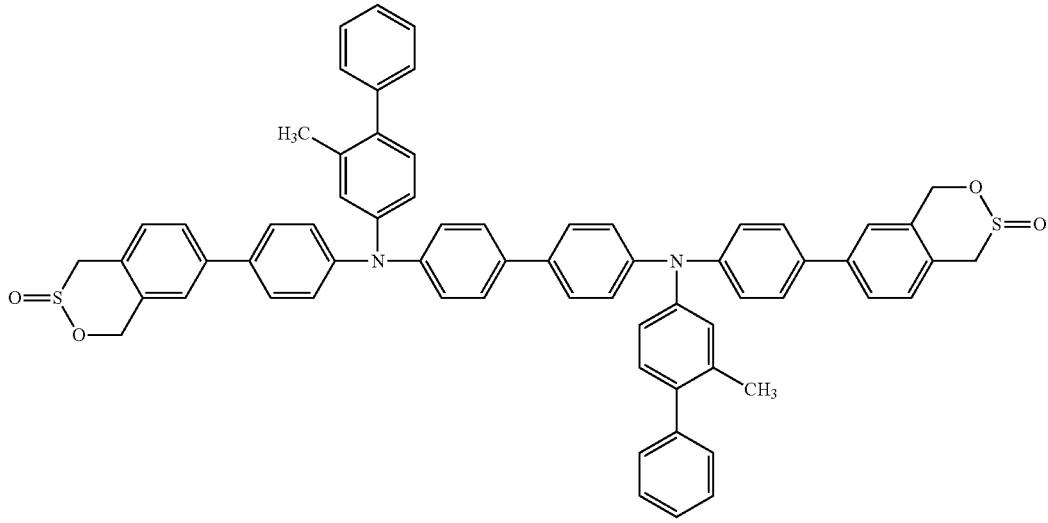

HT2

-continued
HT3
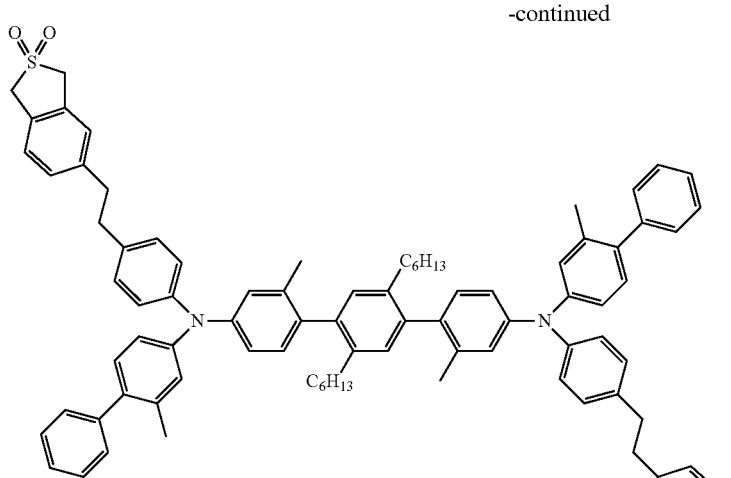
HT4
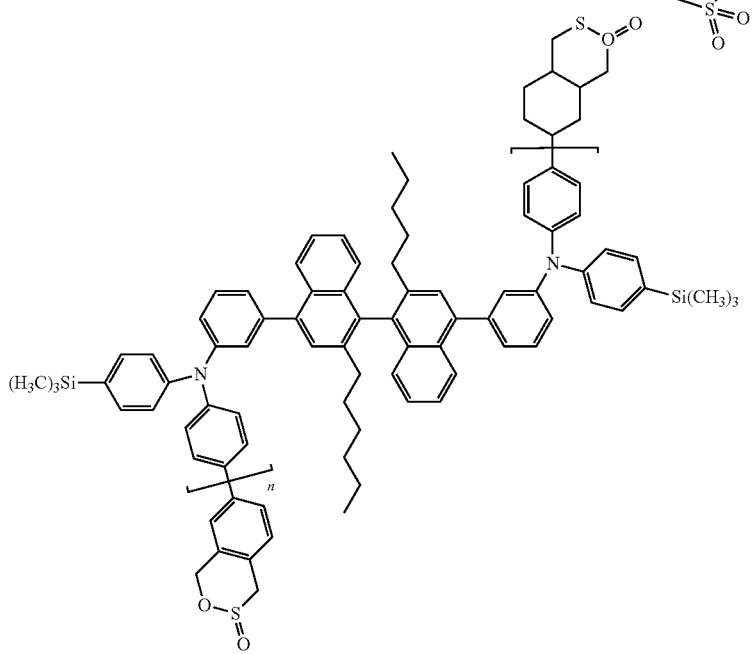
HT5
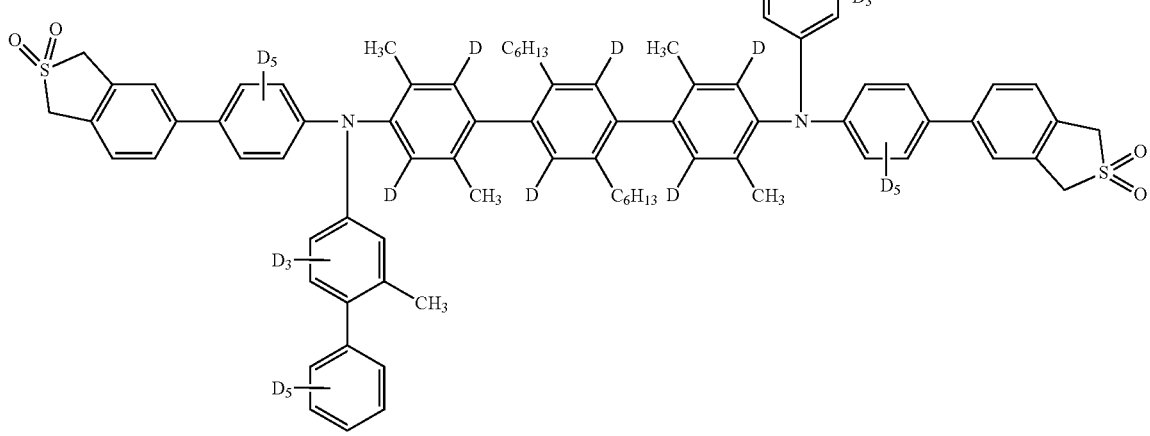

HT6
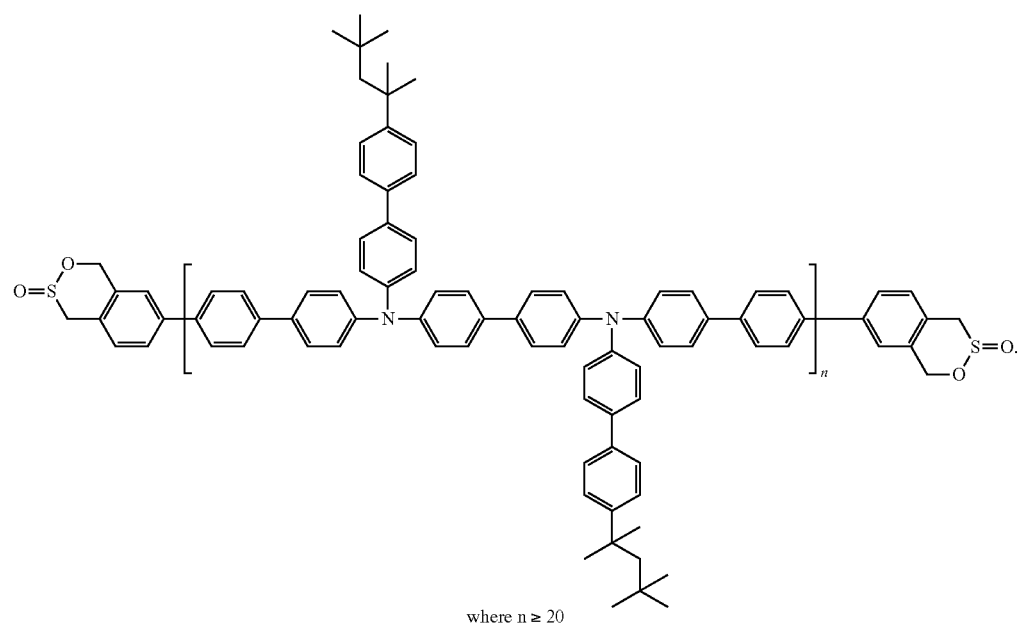
where n ≥ 20
HT7
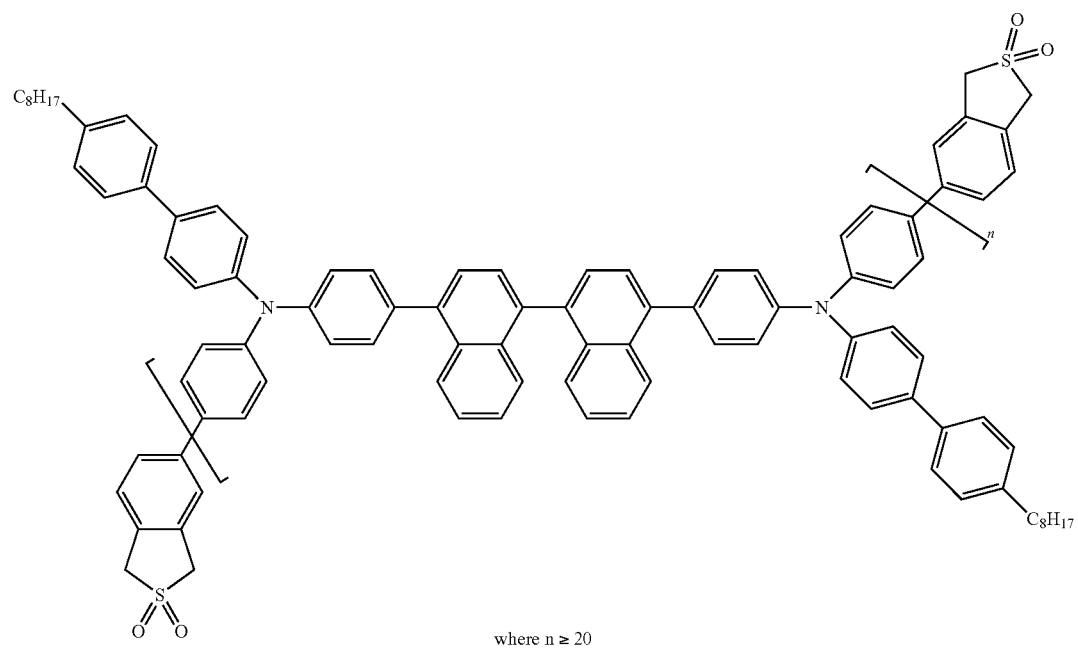
where n ≥ 20

-continued
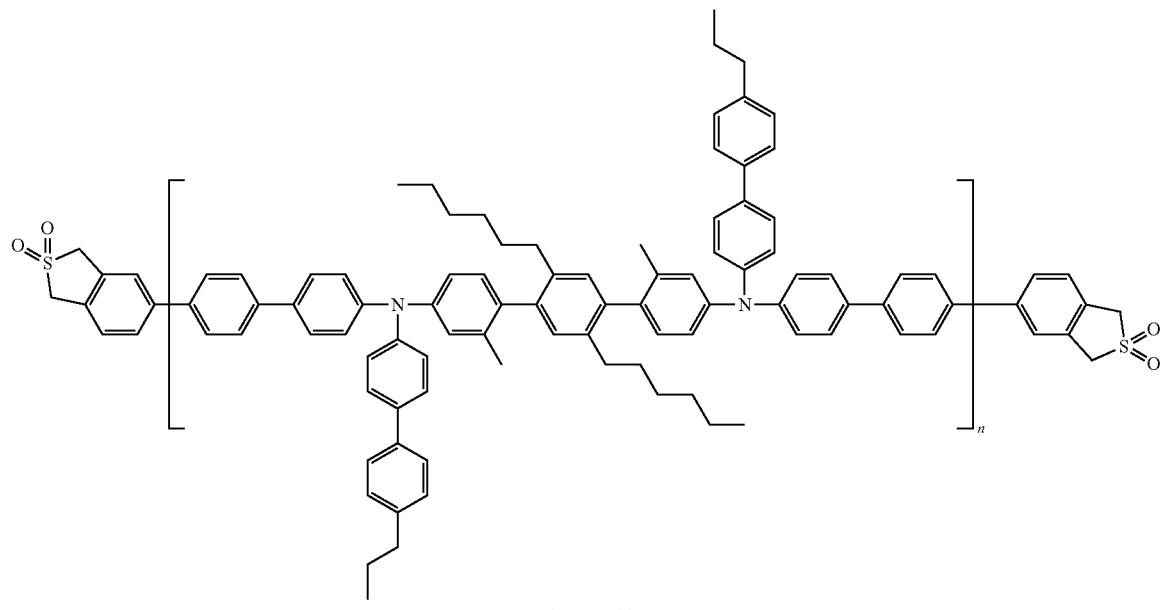
HT8
where n ≥ 20
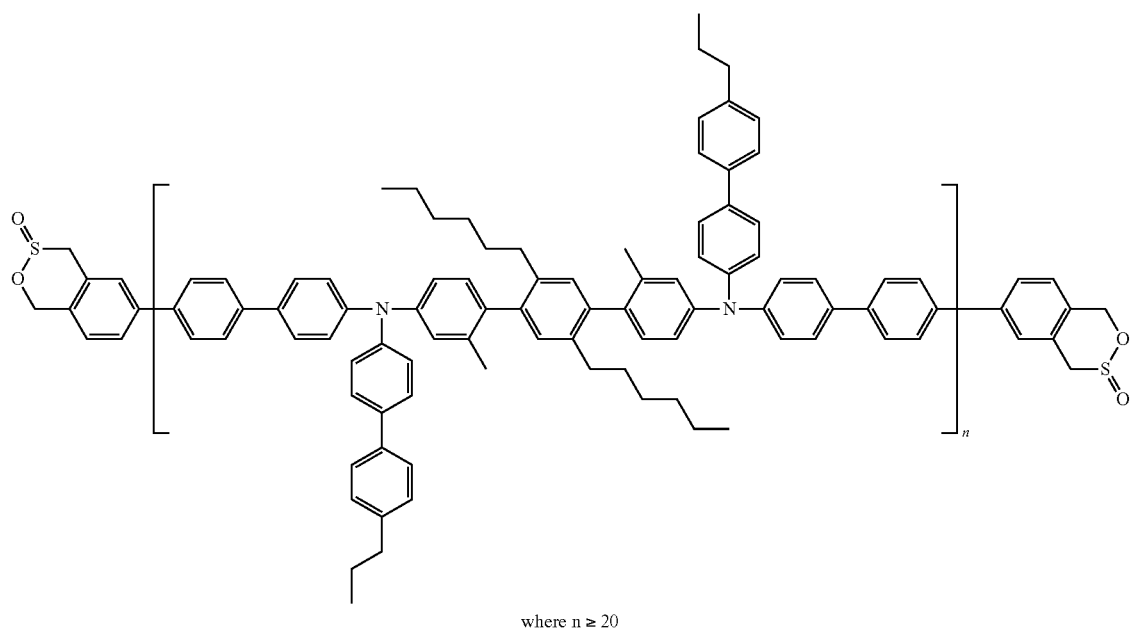
HT9
where n ≥ 20

-continued

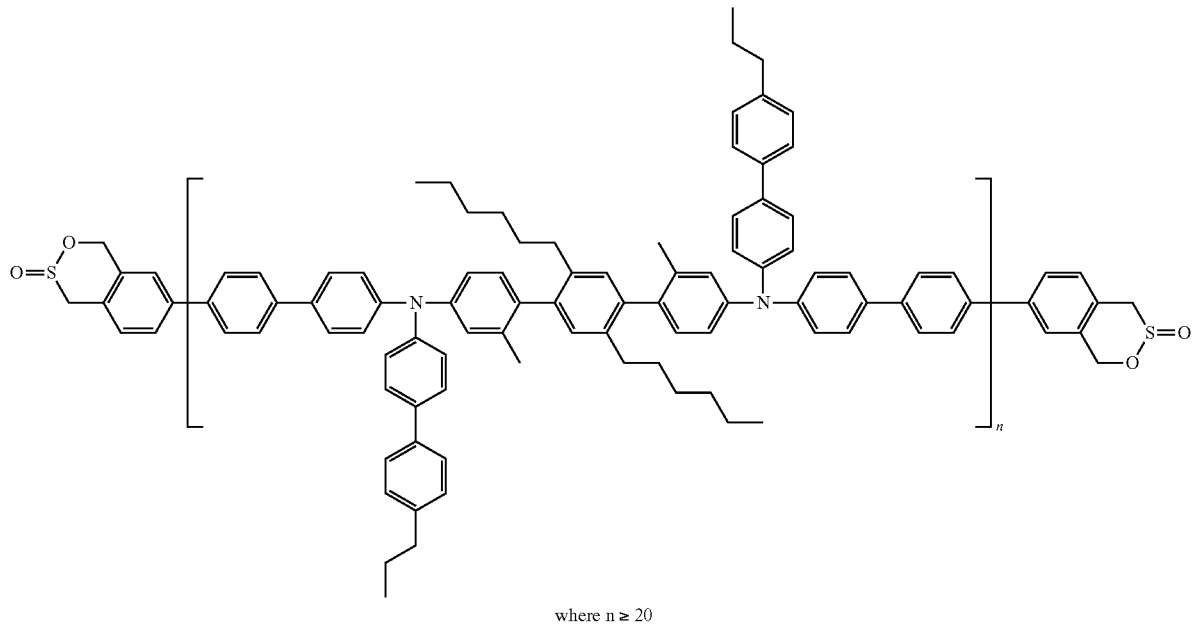

HT10 where n ≥ 20

(ii) Formula Ia

In some embodiments, the hole transport material has Formula Ia

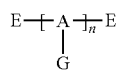  (Ia)

wherein:
  A is an aromatic moiety including at least one triarylamino group;
  E is the same or different at each occurrence and is an end group selected from the group consisting of H, D, halide, alkyl, aryl, deuterated alkyl, and deuterated aryl; and
  G is selected from the group consisting of G1, G2, and deuterated analogs thereof

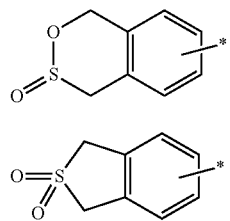

where the asterisk represents the point of attachment; and n is an integer greater than 0.

In some embodiments, the material having Formula Ia is a small molecule with n=1.

In some embodiments, the material having Formula Ia is an oligomer with n=2-5.

In some embodiments, the material having Formula Ia is a polymer with n>5. In some embodiments, the polymer has a weight average molecular weight, $M_w$>20,000; in some embodiments, $M_w$>50,000; in some embodiments, $M_w$>100,000.

In some embodiments, the material having Formula Ia is deuterated. In some embodiments, the material is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments. 100% deuterated.

G1 and G2 are as described above.

The G group in Formula Ia can be bonded directly to an aromatic ring of group A, or it can be bonded to a substituent group on an aromatic ring of group A.

In some embodiments of Formula Ia, group A has formula A-1, as described above. The G group can be bonded directly or through a substituent group to $Ar^2$.

In some embodiments of Formula Ia, group A has formula A-2, as described above. The G group can be bonded directly or through a substituent to group to one or more of $Ar^4$, $Ar^{4a}$, $Ar^5$ or $Ar^{5a}$.

In some embodiments of Formula Ia, group A has formula A-3, as described above. The G group can be bonded directly or through a substituent group to one or more of $Ar^6$, $Ar^7$, $R^2$, $R^3$, $R^4$, or $R^5$, In some embodiments of Formula Ia, group A has formula A-4, as described above. The G group can be bonded directly or through a substituent group to one or more of $Ar^8$ or $Ar^9$.

Any of the above embodiments for Formula Ia can be combined with one or more of the other embodiments, so long as they are not mutually exclusive. For example, the embodiment in which the material is deuterated can be combined with the embodiment where n=1 and the A group has formula A-1. The same is true for the other non-mutually-exclusive embodiments discussed above. The skilled person would understand which embodiments were mutually exclusive and would thus readily be able to determine the combinations of embodiments that are contemplated by the present application.

The monomeric, oligomeric, and polymeric materials having Formula Ia can be made using any technique that will yield a C—C or C—N bond. A variety of such techniques are known, such as Suzuki, Yamamoto, Stille, and Pd- or Ni-catalyzed C—N couplings. Deuterated compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum dichloride. Exemplary preparations are given in the Examples.

Some non-limiting examples of materials having Formula Ia include the following:

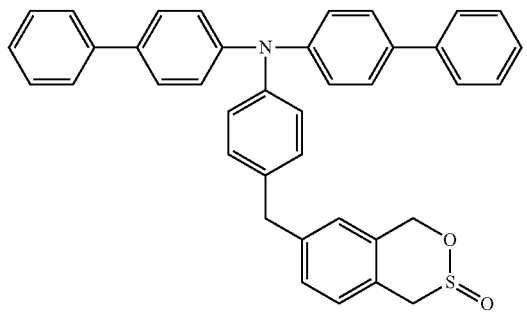

HT11

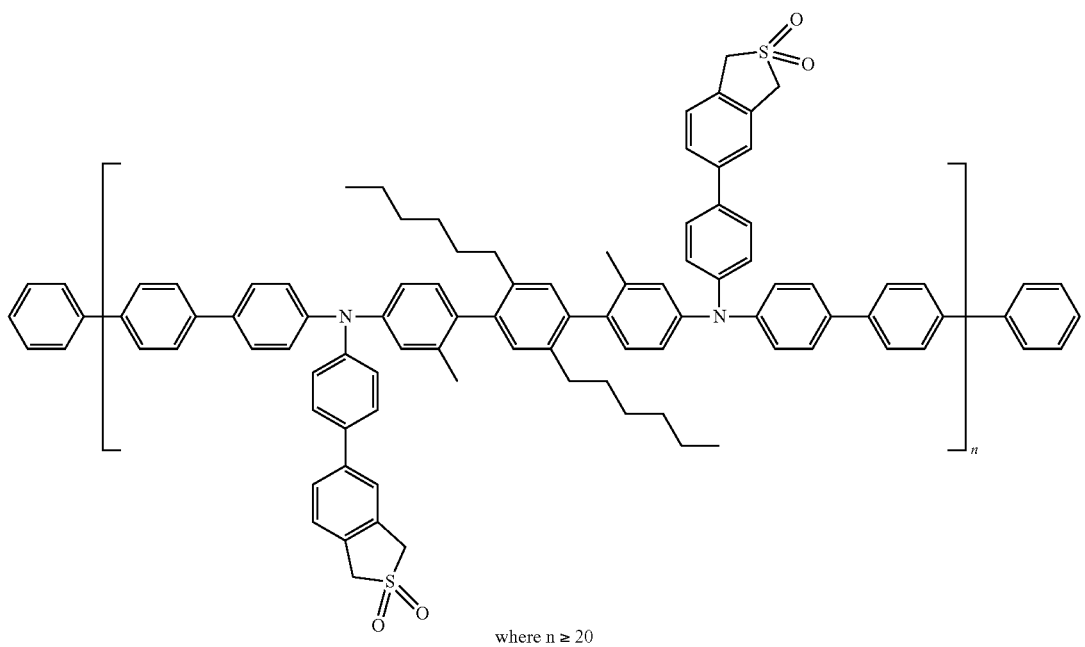

HT12 where n ≥ 20

(iii) Formula II

In some embodiments, the hole transport material has Formula II

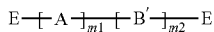
(II)

wherein:
- A is an aromatic moiety including at least one triarylamino group;
- B' is an aromatic moiety having at least one substituent group selected from the group consisting of G1, G2, and deuterated analogs thereof

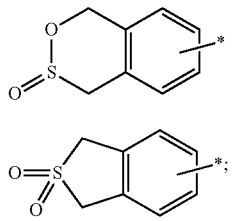

E is the same or different at each occurrence and is an end group selected from the group consisting of H, D, halide, alkyl, aryl, deuterated alkyl, and deuterated aryl: and m1 and m2 represent non-zero mole fractions, such that m1+m2=1.

In some embodiments, the material having Formula II is an oligomer having a molecular weight, $M_w<10,000$.

In some embodiments, the material having Formula II is a polymer.

In some embodiments, the polymer has a molecular weight, $M_w>10,000$; in some embodiments, $M_w>20,000$; in some embodiments, $M_w>50,000$; in some embodiments, $M_w>100,000$.

In Formula II, the "A" and "B" units can be ordered in a regular alternating pattern, in blocks of like monomers, or randomly arranged.

In some embodiments, the material having Formula H is deuterated. In some embodiments, the material is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula II, m2 is less than 0.5. In some embodiments of Formula II, m2 is less than 0.4; in some embodiments, less than 0.3; in some embodiments, less than 0.2; in some embodiments, less than 0.1.

In some embodiments of Formula II, m2 is in the range of 0.01 to 0.30; in some embodiments, in the range of 0.05 to 0.2.

In some embodiments of Formula II, group A has formula A-1, as described above.

In some embodiments of Formula II, group A has formula A-2, as described above.

In some embodiments of Formula II, group A has formula A-3, as described above.

In some embodiments of Formula II, group A has formula A-4, as described above.

In some embodiments of Formula II, group B' includes at least on triarylamino group.

In some embodiments of Formula II, group B' has formula B-1

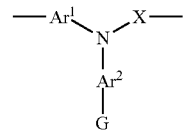
B-1

$Ar^1$-$Ar^2$ are the same or different and are aryl groups;
G is selected from the group consisting of G1, G2, and deuterated analogs thereof

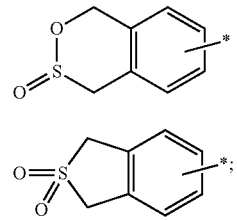

and
X is the same or different at each occurrence and is selected from a single bond, an aryl group, and a deuterated aryl group In some embodiments of formula B'-1, $Ar^1$ and $Ar^2$ are selected from the group consisting of phenyl, naphthyl, anthracenyl, carbazolyl, combinations of such groups linked together covalently, and deuterated analogs thereof.

In some embodiments of formula B-1, X is aryl.

In some embodiments of formula B-1, X is selected from the group consisting of phenyl, naphthyl, anthracenyl, combinations of such groups linked together covalently, and deuterated analogs thereof.

In some embodiments of Formula H, group B' has formula B-2:

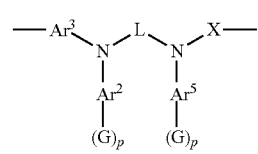
B-2 wherein:
$Ar^3$-$Ar^5$ are the same or different and are aryl groups;
G is selected from the group consisting of G1, G2, and deuterated analogs thereof

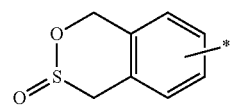
G1

-continued

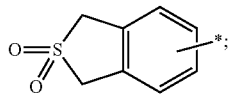
G2

L is the same or different at each occurrence and is aryl, $(CR'_2)_q$, adamantyl, bicyclic cyclohexyl, or a bicyclic group having aliphatic rings connected through a single atom;

R' is the same or different at each occurrence and is H, D, alkyl, fluoroalkyl, aryl, deuterated alkyl, deuterated fluoroalkyl, and deuterated aryl;

X is the same or different at each occurrence and is selected from a single bond, an aryl group, and a deuterated aryl group, with the proviso that N is not bonded directly to G;

p is the same or different at each occurrence and is 0 or 1, with the proviso that at least one p=1; and q is an integer from 1-5.

In some embodiments of formula B-2, $Ar^3$-$Ar^5$ are selected from the group consisting of phenyl, naphthyl, anthracenyl, carbazolyl, combinations of such groups linked together covalently, and deuterated analogs thereof.

In some embodiments of formula B-2, X is aryl.

In some embodiments of formula B-2, X is selected from the group consisting of phenyl, naphthyl, anthracenyl, combinations of such groups linked together covalently, and deuterated analogs thereof.

In some embodiments of Formula II, group B' has formula B-3

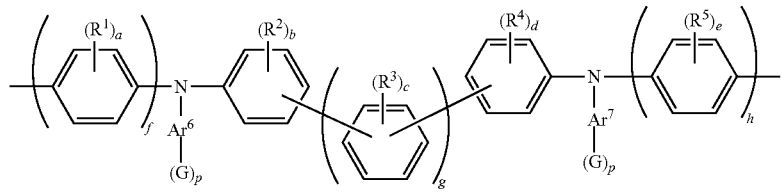
B-3 wherein:
$Ar^6$ and $Ar^7$ are the same or different and are aryl groups;
G is selected from the group consisting of G1, G2, and deuterated analogs thereof

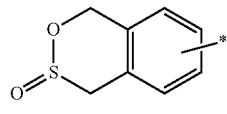
G1

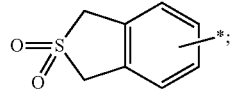
G2

$R^1$ through $R^5$ are independently the same or different at each occurrence and are selected from the group consisting of D, F, alkyl, aryl, alkoxy, silyl, deuterated alkyl, deuterated aryl, deuterated alkoxy, and deuterated silyl;

a through e are independently an integer from 0 to 4;
f is 1 or 2;
g is 0, 1 or 2; h is 1 or 2;
n is an integer greater than 0; and
p is the same or different at each occurrence and is 0 or 1, with the proviso that at least one p=1.

In some embodiments of formula B-3, $Ar^6$ and $Ar^7$ are aryl groups having no fused rings.

In some embodiments of formula B-3, $Ar^6$ and $Ar^7$ have Formula x, as defined above.

In some embodiments of formula B-3, $Ar^6$ and $Ar^7$ have Formula y, as defined above.

In some embodiments of formula B-3, $Ar^6$ and $Ar^7$ are selected from the group consisting of phenyl, biphenyl, terphenyl, deuterated analogs thereof, and derivatives thereof having one or more substituents selected from the group consisting of alkyl, alkoxy, and silyl.

In some embodiments of Formula B-3, $R^1$ through $R^5$ are D or $C_{1-10}$ alkyl. In some embodiments, the alkyl group is deuterated.

In some embodiments of formula B-3, a=e=0. In some embodiments of formula B-3, a=e=4 and $R^1$ and $R^5$ are D.

In some embodiments of formula B-3, b>0 and at least one $R^2$ is alkyl. In some embodiments of formula B-3, the alkyl group is deuterated. In some embodiments of formula B-3, b=4, one $R^2$ is alkyl and the remainder are D.

In some embodiments of formula B-3, c>0 and at least one $R^3$ is alkyl. In some embodiments of formula B-3, the alkyl group is deuterated, In some embodiments of formula B-3, c=4, one $R^3$ is alkyl and the remainder are D. In some embodiments of formula B-3, c=4, two $R^3$ are alkyl and two $R^3$ are D.

In some embodiments of formula B-3, d>0 and at least one $R^4$ is alkyl. In some embodiments of formula B-3, the alkyl group is deuterated.

In some embodiments of formula B-3, d=4, one $R^4$ is alkyl and the remainder are D.

In some embodiments of formula B-3, f=h=2.
In some embodiments of formula B-3, g=1.
In some embodiments of Formula II, group B' has formula B-4

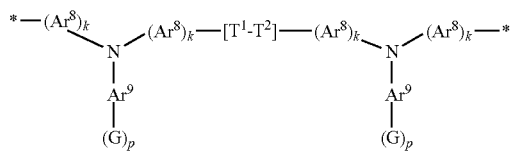
B-4 wherein:
$Ar^8$ is the same or different at each occurrence and is selected from the group consisting of phenylene, substituted phenylene, naphthylene, substituted naphthylene, and deuterated analogs thereof;
$Ar^9$ is the same or different at each occurrence and is an aryl group;

$T^1$ and $T^2$ are independently the same or different at each occurrence and are conjugated moieties which are connected in a non-planar configuration;

k is the same or different at each occurrence and is an integer from 1 to 6;

l is the same or different at each occurrence and is an integer from 1 to 6; and p is the same or different at each occurrence, with the proviso that at least one p=1.

In some embodiments of formula B-4, at least one $Ar^8$ is a substituted phenyl with a substituent selected from the group consisting of alkyl, alkoxy, silyl, and deuterated analogs thereof.

In some embodiments of formula B-4, k is 1-4.

In some embodiments of formula B-4, k is 1-3.

In some embodiments of formula B-4, k=1.

In some embodiments of formula B-4, l is 1-3. In some embodiments l is 1-2.

In some embodiments of formula B-4, l is 1.

In some embodiments of formula B-4, $Ar^9$ has formula x, as defined above.

In some embodiments of formula B-4, $Ar^9$ has formula y, as defined above.

In some embodiments of formula B-4, $Ar^9$ is selected from the group consisting of a group having Formula a, naphthyl, phenylnaphthyl, naphthylphenyl, and deuterated analogs thereof.

In some embodiments of formula B-4, $Ar^9$ is selected from the group consisting phenyl, p-biphenyl, p-terphenyl, naphthyl, phenylnaphthyl, naphthylphenyl, and deuterated analogs thereof.

In some embodiments of formula B-4, $Ar^9$ is selected from the group consisting of phenyl, biphenyl, terphenyl, and deuterated analogs thereof.

Any of the aromatic rings in formula B-4 may be substituted at any position. The substituents may be present to improve one or more physical properties of the compound, such as solubility. In some embodiments, the substituents are selected from the group consisting of $C_{1-12}$ alkyl groups, $C_{1-12}$ alkoxy groups, silyl groups, and deuterated analogs thereof. In some embodiments, the alkyl groups are heteroalkyl groups. In some embodiments, the alkyl groups are fluoroalkyl groups.

In some embodiments of formula B-4, at least one $Ar^9$ has a substituent selected from the group consisting of alkyl, alkoxy, silyl, and deuterated analogs thereof.

The $T^1$-$T^2$ group introduces non-planarity into the backbone of the B-4 group. The moiety in $T^1$ that is directly linked to a moiety in $T^2$ is linked such that the $T^1$ moiety is oriented in a plane that is different from the moiety in $T^2$ to which it is linked. Although other parts of the $T^1$ unit, for example, substituents, may lie in one or more different planes, it is the plane of the linking moiety in $T^1$ and the linking moiety in $T^2$ in the compound backbone that provide the non-planarity. Because of the non-planar $T^1$-$T^2$ linkage, the compounds are chiral. In general, they are formed as racemic mixtures. The compounds can also be in enantiomerically pure form. The non-planarity can be viewed as the restriction to free rotation about the $T^1$-$T^2$ bond. Rotation about that bond leads to racemization. The half-life of racemization for $T^1$-$T^2$ is greater than that for an unsubstituted biphenyl. In some embodiments, the half-life or racemization is 12 hours or greater at 20° C.

In formula B-4, $T^1$ and $T^2$ are conjugated moieties. In some embodiments, $T^1$ and $T^2$ are aromatic moieties.

In some embodiments of formula B-4, $T^1$ and $T^2$ are selected from the group consisting of phenylene, napthylene, and anthracenyl groups.

In some embodiments of formula B-4, [$T^1$-$T^2$] is a substituted biphenylene group. The term "biphenylene" is intended to mean a biphenyl group having two points of attachment to the compound backbone. The term "biphenyl" is intended to mean a group having two phenyl units joined by a single bond. The biphenylene group can be attached at one of the 2-, 3-, 4-, or 5-positions and one of the 2'-, 3'-, 4'-, or 5'-positions. The substituted biphenylene group has at least one substituent in the 2-position. In some embodiments of formula B-4, the biphenylene group has substituents in at least the 2- and 2'-positions.

In some embodiments of formula B-4, [$T^1$-$T^2$] is a binaphthylene group. The term "binaphthylene" is intended to mean a binapthyl group having 2 points of attachment to the compound backbone. The term "binaphthyl" is intended to mean a group having two naphthalene units joined by a single bond. In some embodiments, the binaphthylene group is a 1,1'-binaphthylene, which is attached to the compound backbone at one of the 3-, 4-, 5-, 6, or 7-positions and one of the 3'-, 4'-, 5'-, 6', or 7'-positions. This is illustrated below, where the dashed lines represent possible points of attachment.

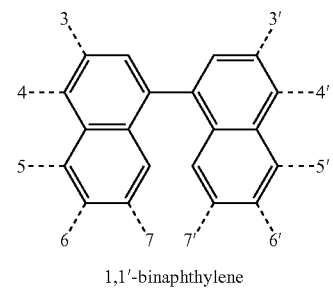

1,1'-binaphthylene

In some embodiments, the binaphthylene group is a 1,2'-binaphthylene having at least one substituent at the 8- or 9'-position, and which is attached to the compound backbone at one of the 3-, 4-, 5-, 6, or 7-positions and one of the 4'-, 5'-, 6'-, 7', or 8'-positions. This is illustrated below, where the dashed lines represent possible points of attachment and at least one R represents a substituent.

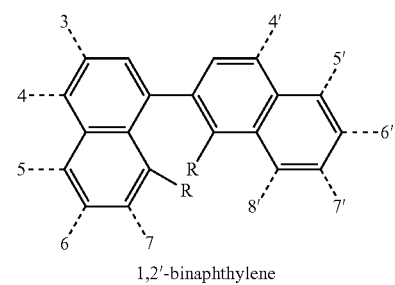

1,2'-binaphthylene

In some embodiments, the binaphthylene group is a 2,2'-binaphthylene having at least one substituent at the 8- or 9'-position, and which is attached to the compound backbone at one of the 4-, 5-, 6-, 7, or 8-positions and one of the 4'-, 5'-, 6'-, 7', or 8'-positions. This is illustrated below, where the dashed lines represent possible points of attachment and at least one R represents a substituent.

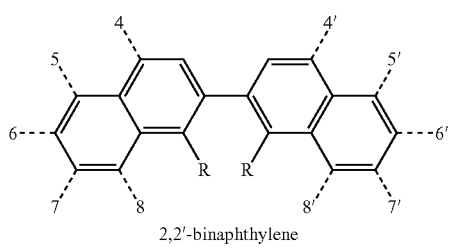

2,2'-binaphthylene

In some embodiments of formula B-4, [$T^1$-$T^2$] is a phenylene-naphthylene group, In some embodiments of formula B-4, [$T^1$-$T^2$] is a phenylene-1-naphthylene group, which is attached to the compound backbone at one of the 3-, 4-, or 5-positions in the phenylene and one of the 3-, 4-, or 5-positions of the naphthylene.

In some embodiments of formula B-4, [$T^1$-$T^2$] is a phenylene-2-naphthylene group, which is attached to the compound backbone at one of the 3-, 4-, or 5-positions in the phenylene and one of the 4-, 5-, 6-, 7-, or 3-positions of the naphthylene.

In some embodiments of formula B-4 the biphenylene, binaphthylene, and phenylene-naphthylene groups are substituted at one or more positions.

In some embodiments of formula B-4, [$T^1$-$T^2$] is selected from one of the following:

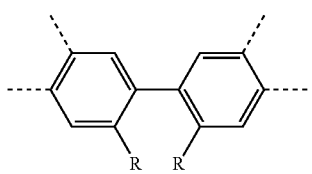

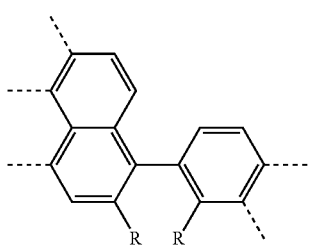

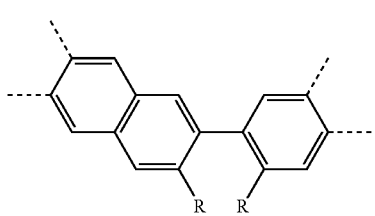

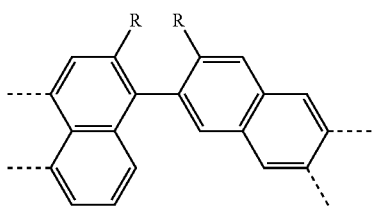

-continued

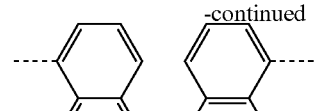

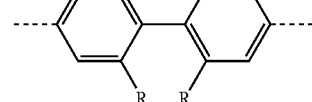

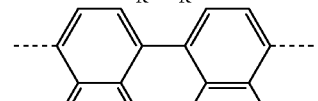

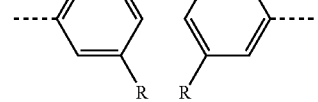

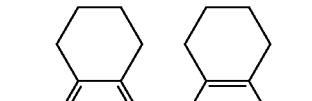

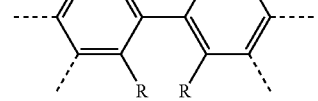

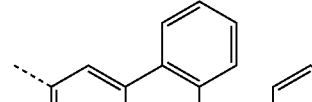

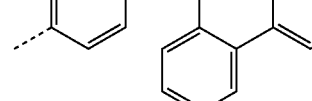

where R is the same or different and is selected from the group consisting of alkyl, aryl, alkoxy, aryloxy, fluoroalkyl, fluoroaryl, fluoroaryloxy fluoroalkyloxy, oxyalkyl, alkenyl groups, silyl, siloxane, and deuterated analogs thereof. The dashed line represents a possible point of attachment to the group backbone. In some embodiments, R is a $C_{1-10}$ alkyl or alkoxy, or deuterated analog thereof; in some embodiments, a $C_{3-8}$ branched alkyl or alkoxy, or deuterated analog thereof. In some embodiments, the two R groups are joined together to form a non-aromatic ring.

In some embodiments of formula B-4, [$T^1$-$T^2$] is a 1,1-binaphthylene group which is attached to the group backbone at the 4 and 4' positions, referred to as 4,4'-(1,1-binaphthylene).

In some embodiments of formula B-4, the 4,4'-(1,1-binaphthylene) is the only isomer present.

In some embodiments of formula B-4, two or more isomers are present.

In some embodiments of formula B-4, the 4,4'-(1,1-binaphthylene) is present with up to 50% by weight of a second isomer.

In some embodiments of formula B-4, the second isomer is selected from the group consisting of 4,5'-(1,1-binaphthylene), 4,6'-(1,1-binaphthylene), and 4,7'-(1,1-binaphthylene).

In some embodiments of Formula II, group B' has no arylamino groups.

In some embodiments of Formula II, group B' has formula B-5

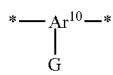

B-5 wherein:
$Ar^{10}$ is a carbocyclic aromatic group having 6-60 ring carbons or a deuterated analog thereof; and
G is selected from the group consisting of G1, G2, and deuterated analogs thereof

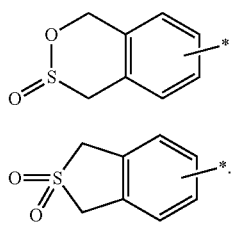

In some embodiments of formula B-5, $Ar^{10}$ is a substituted aryl group having at least, one substituent selected from the group consisting of alkyl, alkoxy, silyl, and deuterated analogs thereof.

In some embodiments of formula B-5, $Ar^{10}$ is selected from the group consisting of phenyl, naphthyl, anthracenyl, combinations of such groups linked together covalently, substituted derivatives thereof, and deuterated analogs thereof.

In some embodiments of formula B-5, $Ar^{10}$ is selected from the group consisting of phenyl, biphenyl, terphenyl, substituted derivatives thereof, and deuterated analogs thereof.

In some embodiments of Formula II, the E group is selected from the group consisting of H, D, phenyl, and deuterated phenyl.

In some embodiments of Formula II, group A has formula A-1 and group B' has formula B-1.

In some embodiments of Formula II, group A has formula A-2 and group B' has formula B-2.

In some embodiments of Formula II, group A has formula A-3 and group B' has formula B-3.

In some embodiments of Formula II, group A has formula A-4 and group B' has formula B-4.

In some embodiments of Formula II, group A has formula A-3 and group B' has formula B-5.

In some embodiments of Formula II, group A has formula A-4 and group B' has formula B-5.

Any of the above embodiments for Formula II can be combined with one or more of the other embodiments, so long as they are not mutually exclusive. For example, the embodiment in which the material is deuterated can be combined with the embodiment where the A group has formula A-1 and the B group has formula B-2. The same is true for the other non-mutually-exclusive embodiments discussed above. The skilled person would understand which embodiments were mutually exclusive and would thus readily be able to determine the combinations of embodiments that are contemplated by the present application.

The materials having Formula II can be made using known coupling and polymerization techniques, as discussed above.

Some non-limiting examples of hole transport materials having Formula II are given below.

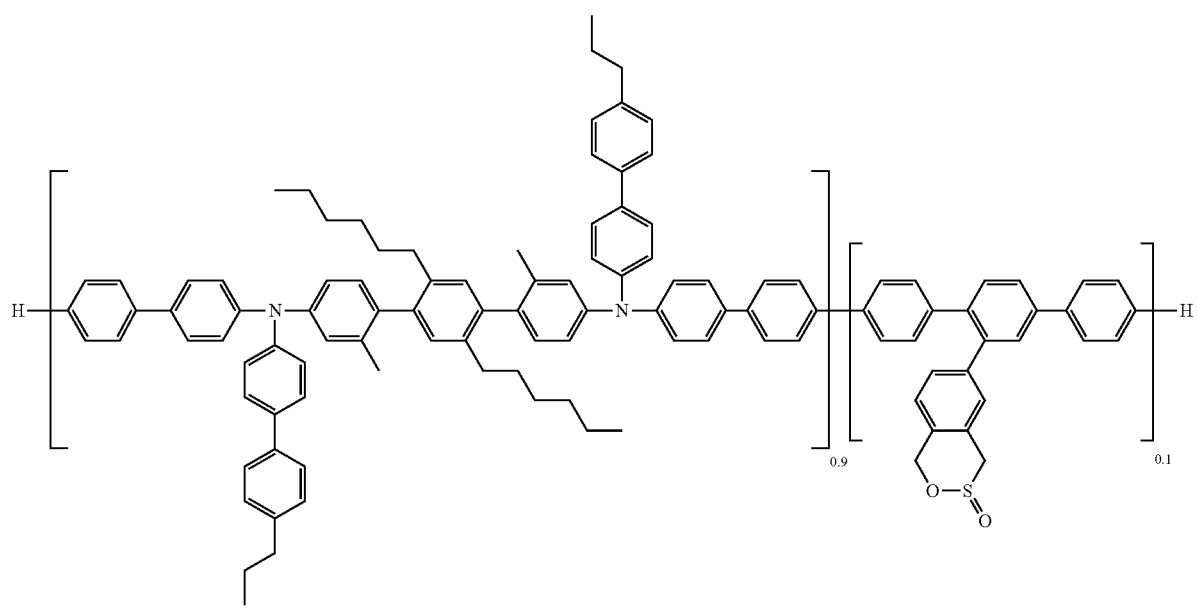

HT13

HT14

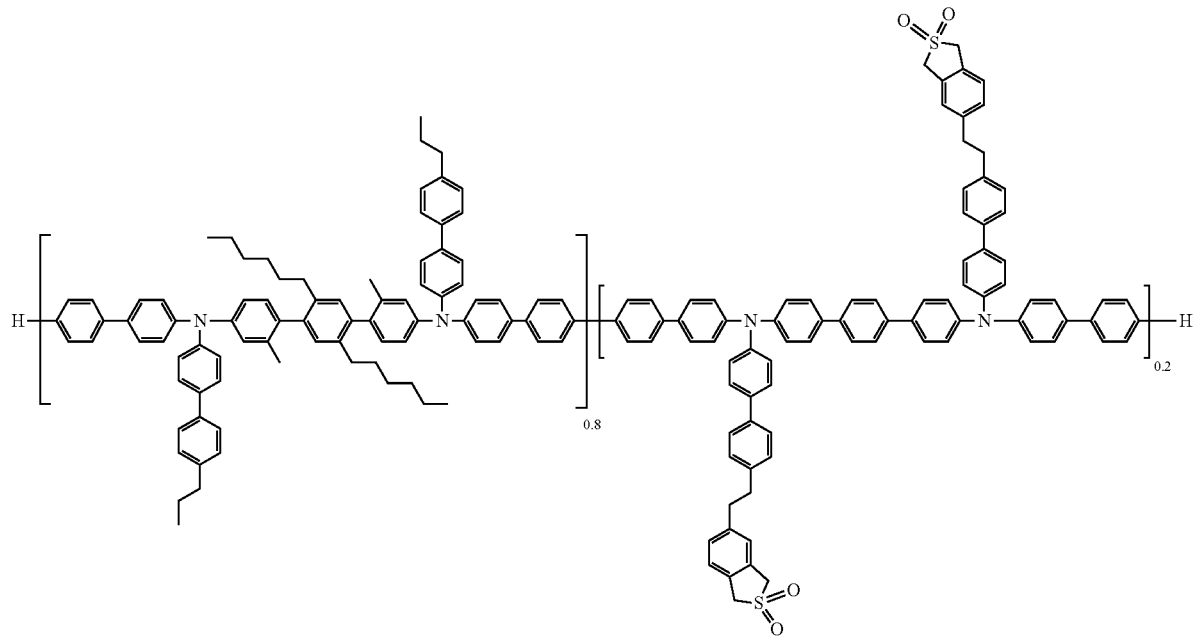

(iv) Formula III

In some embodiments, the hole transport composition includes:
(a) a material having at least one triarylamino group; and
(b) a material having Formula III:

$$G\!-\!\!\!+\!\!J\!\!-\!\!\!\!\!\!-\!\!\!_n\!\!G \quad (III)$$

wherein:
J is an aromatic moiety;
G is selected from the group consisting of G1, G2, and deuterated analogs thereof

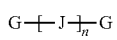 G1

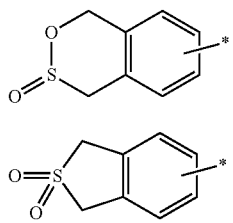 G2 where the asterisk represents the point of attachment; and
n is an integer greater than 0.

In some embodiments, the material having at least one triarylamino group is deuterated. In some embodiments, the material is at least 10% deuterated. In some embodiments, the material is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments, the material having at least one triarylamino group, has formula C-1

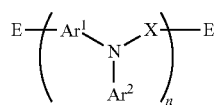 C-1 wherein:
Ar$^1$-Ar$^2$ are the same or different at each occurrence and are aryl groups or deuterated aryl groups;
E is the same or different at each occurrence and is an end group selected from the group consisting of H, D, halide, alkyl, aryl, deuterated alkyl, and deuterated aryl;
X is the same or different at each occurrence and is selected from a single bond, an aryl group, and a deuterated aryl group; and n is an integer greater than 0.

In some embodiments of formula C-1, Ar$^1$ and Ar$^2$ are selected from the group consisting of phenyl, naphthyl, anthracenyl, carbazolyl, combinations of such groups linked together covalently, and deuterated analogs thereof.

In some embodiments of formula C-1, X is aryl,

In some embodiments of formula C-1, X is selected from the group consisting of phenyl, naphthyl, anthracenyl, combinations of such groups linked together covalently, and deuterated analogs thereof.

In some embodiments of formula C-1, E is selected from the group consisting of H, D, phenyl, and deuterated phenyl.

In some embodiments of formula C-1, n=1 and E is H or D.

In some embodiments of formula C-1, n=2-5.

In some embodiments of formula C-1, n>5; in some embodiments n=6-1000.

In some embodiments, the material having at least one triarylamino group has formula C-2:

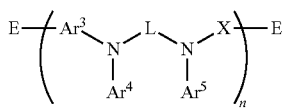

C-2 wherein:
Ar³-Ar⁵ are the same or different at each occurrence and and are aryl groups or deuterated aryl groups;
E is the same or different at each occurrence and is an end group selected from the group consisting of H, D, halide, alkyl, aryl, deuterated alkyl, and deuterated aryl;
L is the same or different at each occurrence and is selected from the group consisting of aryl, $(CR'_2)_q$, adamantyl, bicyclic cyclohexyl, a bicyclic group having aliphatic rings connected through a single atom, and deuterated analogs thereof;
R' is the same or different at each occurrence and is selected from the group consisting of H, D, alkyl, fluoroalkyl, aryl, deuterated alkyl, deuterated fluoroalkyl, and deuterated aryl;
X is the same or different at each occurrence and is selected from a single bond, an aryl group, and a deuterated aryl group;
q is an integer from 1-5; and
n is an integer greater than 0.

In some embodiments of formula C-2, Ar³-Ar⁵ are selected from the group consisting of phenyl, naphthyl, anthracenyl, carbazolyl, combinations of such groups linked together covalently, and deuterated analogs thereof.

In some embodiments of formula C-2, X is aryl.

In some embodiments of formula C-2, X is selected from the group consisting of phenyl, naphthyl, anthracenyl, combinations of such groups linked together covalently, and deuterated analogs thereof.

In some embodiments of formula C-2, L is selected from the group consisting of phenyl, deuterated phenyl, and $C(CF_3)_2$.

In some embodiments of formula C-2, L is $(CR'_2)_q$, where R' is H or D and q=1 or 2.

In some embodiments of formula C-2, E is selected from the group consisting of H, D, phenyl, and deuterated phenyl.

In some embodiments of formula C-2, n=1.
In some embodiments of formula C-2, n=2-5.
In some embodiments of formula C-2, n>5; in some embodiments n=6-1000.

In some embodiments, the material having at least one triarylamino group has formula C-3 wherein:
Ar⁶ and Ar⁷ are the same or different and are aryl groups;
E is the same or different at each occurrence and is an end group selected from the group consisting of H, D, halide, alkyl, aryl, deuterated alkyl, and deuterated aryl;
R¹ through R⁵ are independently the same or different at each occurrence and are selected from the group consisting of D, F, alkyl, aryl, alkoxy, silyl, deuterated alkyl, deuterated aryl, deuterated alkoxy, and deuterated silyl;
a through e are independently an integer from 0 to 4;
f is 1 or 2;
g is 0, 1 or 2; and
h is 1 or 2; and
n is an integer greater than 0.

In some embodiments of formula C-3, Ar⁶ and Ar⁷ are aryl groups having no fused rings.

In some embodiments of formula C-3, Ar⁶ and Ar⁷ have Formula x

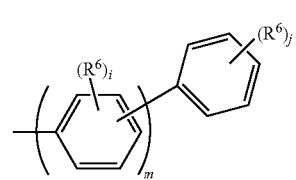

Formula x where:
R⁶ is the same or different at each occurrence and is selected from the group consisting of D, alkyl, alkoxy, siloxane, silyl, deuterated alkyl, deuterated alkoxy, deuterated siloxane, and deuterated silyl;
i is the same or different at each occurrence and is an integer from 0-4;
j is an integer from 0-5; and
m is an integer from 1 to 5.

In some embodiments of formula C-3, Ar⁶ and Ar⁷ have Formula y

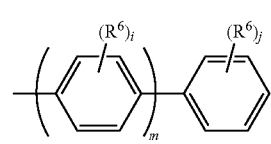

Formula y where:
R⁶ is the same or different at each occurrence and is selected from the group consisting of D, alkyl, alkoxy, siloxane and silyl;

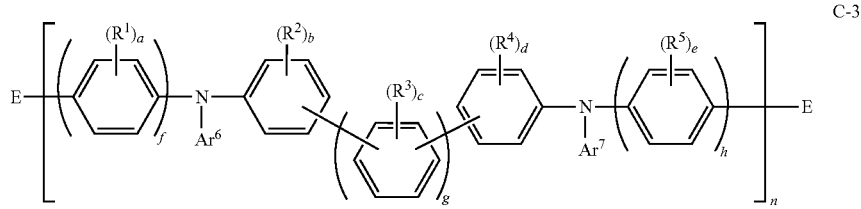

C-3 i is the same or different at each occurrence and is an integer from 0-4;

j is an integer from 0-5; and m is an integer from 1 to 5.

In some embodiments of Formulae x and y, at least one of i and j is not zero. In some embodiments, m=1-3.

In some embodiments of formula C-3, $Ar^6$ and $Ar^7$ are selected from the group consisting of phenyl, biphenyl, terphenyl, deuterated analogs thereof, and derivatives thereof having one or more substituents selected from the group consisting of alkyl, alkoxy, and silyl.

In some embodiments of Formula C-3, $R^1$ through $R^5$ are D or $C_{1-10}$ alkyl. In some embodiments, the alkyl group is deuterated.

In some embodiments of formula C-3, a=e=0. In some embodiments of formula C-3, a=e=4 and $R^1$ and $R^5$ are D.

In some embodiments of formula C-3, b>0 and at least one $R^2$ is alkyl. In some embodiments of formula 0-3, the alkyl group is deuterated. In some embodiments of formula 0-3, b=4, one $R^2$ is alkyl and the remainder are D.

In some embodiments of formula C-3, c>0 and at least one $R^3$ is alkyl. In some embodiments of formula C-3, the alkyl group is deuterated. In some embodiments of formula C-3, c=4, one $R^3$ is alkyl and the remainder are D. In some embodiments of formula C-3, c=4, two $R^3$ are alkyl and two $R^3$ are D.

In some embodiments of formula C-3, d>0 and at least one $R^4$ is alkyl. In some embodiments of formula C-3, the alkyl group is deuterated. In some embodiments of formula C-3, d=4, one $R^4$ is alkyl and the remainder are D.

In some embodiments of formula C-3, f=h=2.

In some embodiments of formula C-3, g=1.

In some embodiments of formula C-3, E is selected from the group consisting of H, D, phenyl, and deuterated phenyl.

In some embodiments of formula C-3, n=1 and E is H or D.

In some embodiments of formula C-3, n=2-5.

In some embodiments of formula C-3, n>5; in some embodiments, n=6-1000.

In some embodiments, the material having triarylamino groups has formula C-4

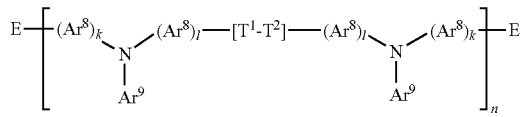

C-4 wherein:

$Ar^8$ is the same or different at each occurrence and is selected from the group consisting of phenylene, substituted phenylene, naphthylene, substituted naphthylene, and deuterated analogs thereof;

$Ar^9$ is the same or different at each occurrence and is an aryl group;

E is the same or different at each occurrence and is an end group selected from the group consisting of H. D, halide, alkyl, aryl, deuterated alkyl, and deuterated aryl;

$T^1$ and $T^2$ are independently the same or different at each occurrence and are conjugated moieties which are connected in a non-planar configuration;

k is the same or different at each occurrence and is an integer from 1 to 6;

l is the same or different at each occurrence and is an integer from 1 to 6; and n is an integer greater than 0.

In some embodiments of formula C-4, at least one $Ar^8$ is a substituted phenyl with a substituent selected from the group consisting of alkyl, alkoxy, silyl, and deuterated analogs thereof.

In some embodiments of formula C-4, k is 1-4.

In some embodiments of formula C-4, k is 1-3.

In some embodiments of formula C-4, k=1.

In some embodiments of formula C-4, l is 1-3 In some embodiments l is 1-2.

In some embodiments of formula C-4, l is 1.

In some embodiments of formula C-4, $Ar^9$ has formula x, as defined above.

In some embodiments of formula C-4, $Ar^9$ has formula y, as defined above.

In some embodiments of formula C-4, $Ar^9$ is selected from the group consisting of a group having Formula a, naphthyl, phenylnaphthyl, naphthylphenyl, and deuterated analogs thereof.

In some embodiments of formula C-4, $Ar^9$ is selected from the group consisting phenyl, p-biphenyl, p-terphenyl, naphthyl, phenylnaphthyl, naphthylphenyl, and deuterated analogs thereof.

In some embodiments of formula C-4, $Ar^9$ is selected from the group consisting of phenyl, biphenyl, terphenyl, and deuterated analogs thereof.

Any of the aromatic rings in formula C-4 may be substituted at any position. The substituents may be present to improve one or more physical properties of the compound, such as solubility. In some embodiments, the substituents are selected from the group consisting of $C_{1-12}$ alkyl groups, $C_{1-12}$ alkoxy groups, silyl groups, and deuterated analogs thereof. In some embodiments, the alkyl groups are heteroalkyl groups. In some embodiments, the alkyl groups are fluoroalkyl groups.

In some embodiments of formula C-4, at least one $Ar^9$ has a substituent selected from the group consisting of alkyl, alkoxy, silyl, and deuterated analogs thereof.

The $T^1$-$T^2$ group introduces non-planarity into the backbone of the C-4 group. The moiety in $T^1$ that is directly linked to a moiety in $T^2$ is linked such that the $T^1$ moiety is oriented in a plane that is different from the moiety in $T^2$ to which it is linked. Although other parts of the $T^1$ unit, for example, substituents, may lie in one or more different planes, it is the plane of the linking moiety in $T^1$ and the linking moiety in $T^2$ in the compound backbone that provide the non-planarity. Because of the non-planar $T^1$-$T^2$ linkage, the compounds are chiral. In general, they are formed as racemic mixtures. The compounds can also be in enantiomerically pure form. The non-planarity can be viewed as the restriction to free rotation about the $T^1$-$T^2$ bond. Rotation about that bond leads to racemization. The half-life of racemization for $T^1$-$T^2$ is greater than that for an unsubstituted biphenyl. In some embodiments, the half-life or racemization is 12 hours or greater at 20° C.

In formula C-4, $T^1$ and $T^2$ are conjugated moieties. In some embodiments, $T^1$ and $T^2$ are aromatic moieties.

In some embodiments of formula C-4, $T^1$ and $T^2$ are selected from the group consisting of phenylene, napthylene, and anthracenyl groups.

In some embodiments of formula C-4, [$T^1$-$T^2$] is a substituted biphenylene group. The term "biphenylene" is intended to mean a biphenyl group having two points of attachment to the compound backbone. The term "biphenyl" is intended to mean a group having two phenyl units joined by a single bond. The biphenylene group can be attached at one of the 2, 3-, 4-, or 5-positions and one of the 2', 3'-, 4'-, or 5'-positions. The substituted biphenylene group has at least one substitutent in the 2-position. In some embodiments of formula C-4, the biphenylene group has substituents in at least the 2- and 2'-positions.

In some embodiments of formula C-4, [T$^1$-T$^2$] is a binaphthylene group. The term "binaphthylene" is intended to mean a binapthyl group having 2 points of attachment to the compound backbone. The term "binaphthyl" is intended to mean a group having two naphthalene units joined by a single bond. In some embodiments, the binaphthylene group is a 1,1'-binaphthylene, which is attached to the compound backbone at one of the 3-, 4-, 5-, 6, or 7-positions and one of the 3'-, 4'-, 5'-, 6', or 7'-positions. This is illustrated below, where the dashed lines represent possible points of attachment.

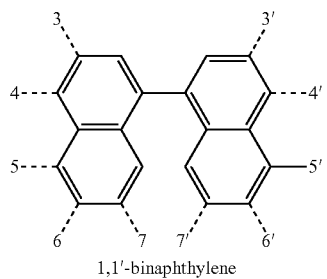

1,1'-binaphthylene

In some embodiments, the binaphthylene group is a 1,2'-binapthylene having at least one substituent at the 8- or 9'-position, and which is attached to the compound backbone at one of the 3-, 4-, 5-, 6, or 7-positions and one of the 4'-, 5'-, 6'-, 7', or 8'-positions. This is illustrated below, where the dashed lines represent possible points of attachment and at least one R represents a substituent.

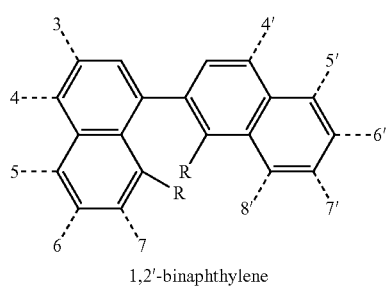

1,2'-binaphthylene

In some embodiments, the binaphthylene group is a 2,2'-binaphthylene having at least one substituent at the 8- or 9'-position, and which is attached to the compound backbone at one of the 4-, 5-, 6-, 7, or 8-positions and one of the 4'-, 5'-, 6'-, 7', or 8'-positions. This is illustrated below, where the dashed lines represent possible points of attachment and at least one R represents a substituent.

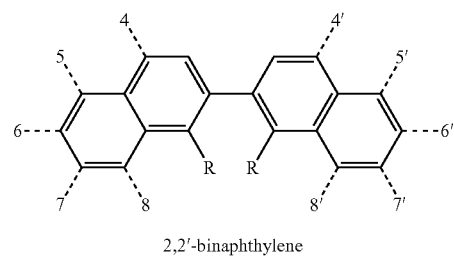

2,2'-binaphthylene

In some embodiments of formula C-4, [T$^1$-T$^2$] is a phenylene-naphthylene group, In some embodiments of formula C-4, [T$^1$-T$^2$] is a phenylene-1-naphthylene group, which is attached to the compound backbone at one of the 3-, 4-, or 5-positions in the phenylene and one of the 3-, 4-, or 5-positions of the naphthylene.

In some embodiments of formula C-4, [T$^1$-T$^2$] is a phenylene-2-naphthylene group, which is attached to the compound backbone at one of the 3-, 4-, or 5-positions in the phenylene and one of the 4-, 5-, 6-, 7-, or 8-positions of the naphthylene.

In some embodiments of formula C-4, the biphenylene, binaphthylene, and phenylene-naphthylene groups are substituted at one or more positions.

In some embodiments of formula C-4, [T$^1$-T$^2$] is selected from one of the following:

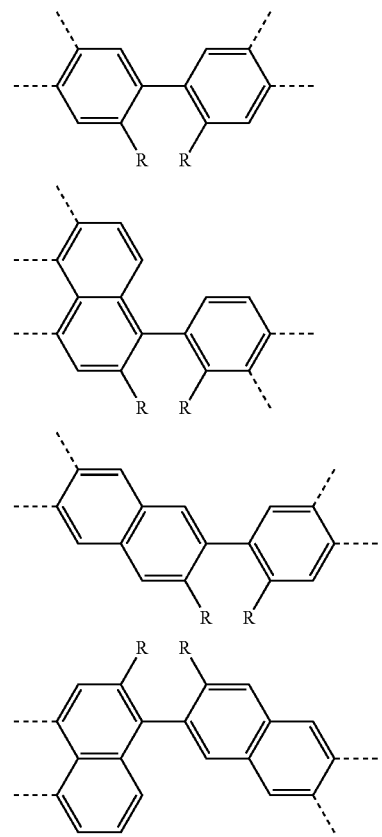

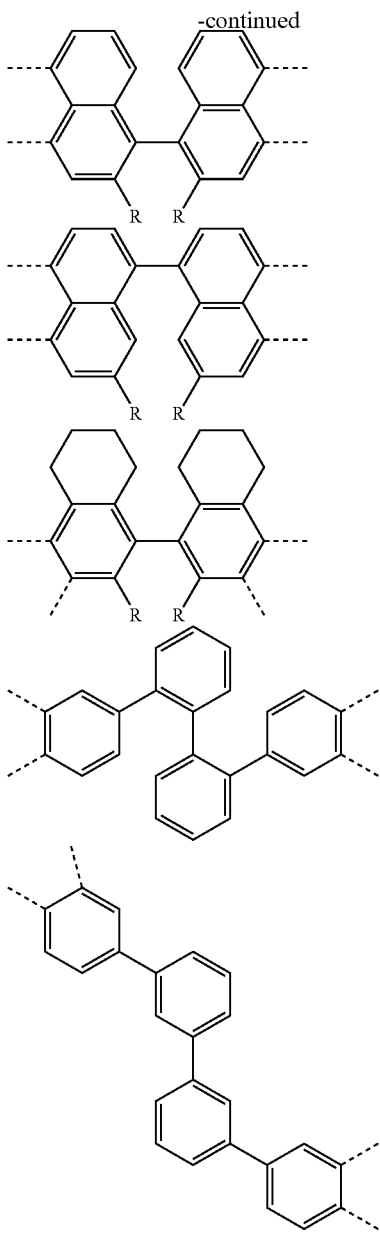

where R is the same or different and is selected from the group consisting of alkyl, aryl, alkoxy, aryloxy, fluoroalkyl, fluoroaryl, fluoroaryloxy fluoroalkyloxy, oxyalkyl, alkenyl groups, silyl, siloxane, and deuterated analogs thereof. The dashed line represents a possible point of attachment to the group backbone. In some embodiments, R is a $C_{1-10}$ alkyl or alkoxy, or deuterated analog thereof; in some embodiments, a $C_{3-8}$ branched alkyl or alkoxy, or deuterated analog thereof. In some embodiments, the two R groups are joined together to form a non-aromatic ring.

In some embodiments of formula C-4, $[T^1-T^2]$ is a 1,1-binaphthylene group which is attached to the group backbone at the 4 and 4' positions, referred to as 4,4'-(1,1-binaphthylene).

In some embodiments of formula C-4, the 4,4'-(1,1-binaphthylene) is the only isomer present.

In some embodiments of formula C-4, two or more isomers are present.

In some embodiments of formula C-4, the 4,4'-(1,1-binaphthylene) is present with up to 50% by weight of a second isomer.

In some embodiments of formula C-4, the second isomer is selected from the group consisting of 4,5'-(1,1-binaphthylene), 4,6'-(1,1-binapthylene), and 4,7'-(1,1-binaphthylene).

In some embodiments of formula C-4, E is selected from the group consisting of H, D, phenyl, and deuterated phenyl.

In some embodiments of formula C-4, n=1 and E is H or D.

In some embodiments of formula C-4, n=2-5.

In some embodiments of formula C-4, n>5. In some embodiments, n=6-1000.

Some examples of materials including at least one triarylamino group have been summarized for example, in Kirk-Othmer Encyclopedia of Chemical Technology, Fourth Edition, Vol. 18, p. 837-860, 1996, by Y. Wang. Commonly used hole transporting molecules include, but are not limited to: 4,4',4"-tris(N,N-diphenyl-amino)-triphenylamine (TDATA); 4,4',4"-tris(N-3-methylphenyl-N-phenyl-amino)-triphenylamine (MTDATA); N,N'-diphenyl-N,N'-bis(3-methylphenyl)-[1,1'-biphenyl]-4,4'-diamine (TPD); 4,4'-bis(carbazol-9-yl)biphenyl (CBP); 1,3-bis(carbazol-9-yl)benzene (mCP); 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); α-phenyl-4-N,N-diphenylaminostyrene (TPS); p-(diethylamino)benzaldehyde diphenylhydrazone (DEH); triphenylamine (TPA); bis[4-(N,N-diethylamino)-2-methylphenyl](4-methylphenyl)methane (MPMP); 1-phenyl-3-[p-(diethylamino)styryl]-5-[p-(diethylamino)phenyl] pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); and N,N'-bis(naphthalen-1-yl)-N,N'-bis-(phenyl)benzidine (α-NPB).

Any of the above embodiments for the material including at least one triarlyamino group can be combined with one or more of the other embodiments, so long as they are not mutually exclusive. The skilled person would understand which embodiments were mutually exclusive and would thus readily be able to determine the combinations of embodiments that are contemplated by the present application.

In some embodiments, the material having Formula III is a small molecule with n=1.

In some embodiments, the material having Formula III is an oligomer with n=2-5.

In some embodiments, the material having Formula III is a polymer with n>5. In some embodiments, the polymer has a weight average molecular weight, $M_w>20,000$; in some embodiments, $M_w>50,000$; in some embodiments, $M_w>100,000$.

In some embodiments, the material having Formula III is deuterated. In some embodiments, the material is at least 10% deuterated. In some embodiments, the material is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments. 100% deuterated.

In some embodiments of Formula III, group J has formula J-1

      J-1 wherein:
$Ar^{10}$ is a carbocyclic aromatic group having 6-60 ring carbons or a deuterated analog thereof.

In some embodiments of formula J-1, $Ar^{10}$ is a substituted aryl group having at least one substituent selected from the group consisting of alkyl, alkoxy, silyl, and deuterated analogs thereof.

In some embodiments of formula J-1, $Ar^{10}$ is selected from the group consisting of phenyl, naphthyl, anthracenyl, combinations of such groups linked together covalently, substituted derivatives thereof, and deuterated analogs thereof.

In some embodiments of formula J-1, $Ar^{10}$ is selected from the group consisting of phenyl, biphenyl, terphenyl, substituted derivatives thereof, and deuterated analogs thereof.

In some embodiments of Formula III, J has formula J-2

      J-2 wherein:
$Ar^{10}$ and $Ar^{11}$ are the same or different at each occurrence and are selected from the group consisting of carbocyclic aromatic groups having 6-60 ring carbons, substituted carbocyclic aromatic groups having 6-60 ring carbons, and deuterated analogs thereof;
L' is selected from the group consisting of alkyl, fluoroalkyl, silyl, and deuterated analogs thereof; and
t is an integer from 1 to 10.

In some embodiments of formula J-2 $Ar^{10}$ is a substituted aryl group having at least one substituent selected from the group consisting of alkyl, alkoxy, silyl, and deuterated analogs thereof.

In some embodiments of formula J-2, $Ar^{10}$ is selected from the group consisting of phenyl, naphthyl, anthracenyl, combinations of such groups linked together covalently, substituted derivatives thereof, and deuterated analogs thereof.

In some embodiments of formula J-2, $Ar^{10}$ is selected from the group consisting of phenyl, biphenyl, terphenyl, substituted derivatives thereof, and deuterated analogs thereof.

In some embodiments of formula J-2, $Ar^{11}$ is a substituted aryl group having at least one substituent selected from the group consisting of alkyl, alkoxy, silyl, and deuterated analogs thereof.

In some embodiments of formula J-2, $Ar^{11}$ is selected from the group consisting of phenyl, naphthyl, anthracenyl, combinations of such groups linked together covalently, substituted derivatives thereof, and deuterated analogs thereof.

In some embodiments of formula J-2, $Ar^{11}$ is selected from the group consisting of phenyl, biphenyl, terphenyl, substituted derivatives thereof, and deuterated analogs thereof.

In some embodiments of formula J-2, L' is a C1-C6 alkyl or deuterated analog thereof.

In some embodiments of formula J-2, L' is a C1-C6 fluoroalkyl or deuterated analog thereof. In some embodiments of formula J-2, L' is a C1-C2 perfluoroalkyl.

In some embodiments of formula J-2, t=1 or 2.

Any of the above embodiments for Formula III can be combined with one or more of the other embodiments, so long as they are not mutually exclusive. For example, the embodiment in which the material is deuterated can be combined with the embodiment where n=1 and the J group has formula J-2. The same is true for the other non-mutually-exclusive embodiments discussed above. The skilled person would understand which embodiments were mutually exclusive and would thus readily be able to determine the combinations of embodiments that are contemplated by the present application.

The material having Formula III can be made using known coupling techniques and polymerization techniques.

Some non-limiting examples of materials having Formula III are given below.

Compound 1

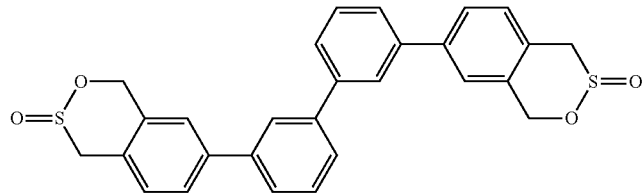

Compound 2

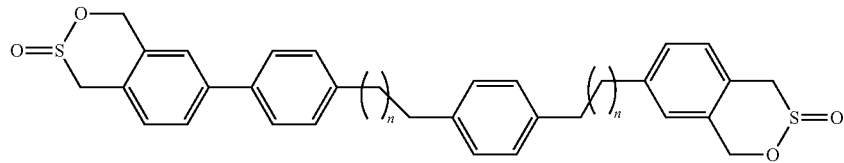

where n is 1 or 2.

Compound 3

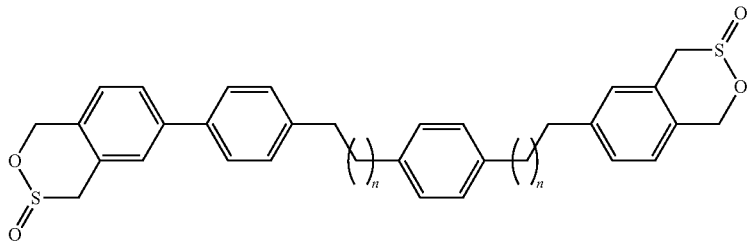

where n is 1 or 2.

Compound 4

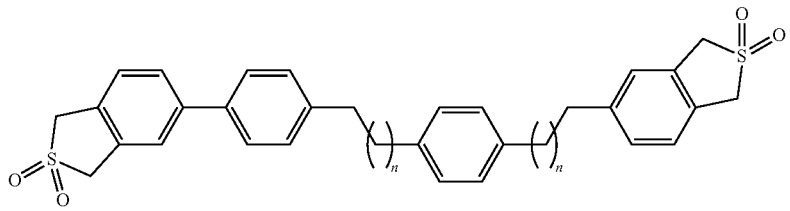

where n is 1 or 2.

The hole transport composition can include any of the materials having at least one triarylamino group, described above, and any of the materials having Formula III.

(v) Formula IIIa

In some embodiments, the hole transport composition includes:
(a) a material having at least one triarylamino group; and
(b) a material having Formula IIIa:

$$E\text{---}(\text{J})_n\text{---}E$$
$$|$$
$$G$$

(IIIa)

wherein:
J is an aromatic moiety;
E is the same or different at each occurrence and is an end group selected from the group consisting of H, D, halide, alkyl, aryl, deuterated alkyl, and deuterated aryl;
G is selected from the group consisting of G1, G2, and deuterated analogs thereof

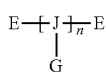

G1

G2

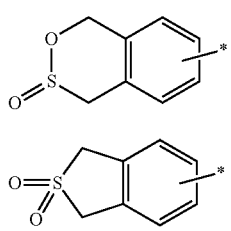

where the asterisk represents the point of attachment; and n is an integer greater than 0.

The material having at least one triarylamino group can be any of those discussed above with respect to Formula III.

In some embodiments, the material having Formula IIIa is a small molecule with n=1.

In some embodiments, the material having Formula IIIa is an oligomer with n=2-5.

In some embodiments, the material having Formula III is a polymer with n>5. In some embodiments, the polymer has a weight average molecular weight, $M_b>20,000$; in some embodiments, $M_w>50,000$; in some embodiments, $M_w>100,000$.

In some embodiments, the material having Formula IIIa is deuterated. In some embodiments, the material is at least 10% deuterated. In some embodiments, the material is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments. 100% deuterated.

In some embodiments of Formula IIIa, group J has formula J-1, as described above.

In some embodiments of Formula IIIa, J has formula J-2, as described above.

Any of the above embodiments for Formula IIIa can be combined with one or more of the other embodiments, so long as they are not mutually exclusive. For example, the embodiment in which the material is deuterated can be combined with the embodiment where n=1 and the J group has formula J-2. The same is true for the other non-mutually-exclusive embodiments discussed above. The skilled person would understand which embodiments were mutually exclusive and would thus readily be able to determine the combinations of embodiments that are contemplated by the present application.

The material having Formula IIIa can be made using known coupling techniques and polymerization techniques.

Some non-limiting examples of materials having Formula IIIa are given below.

Compound 5

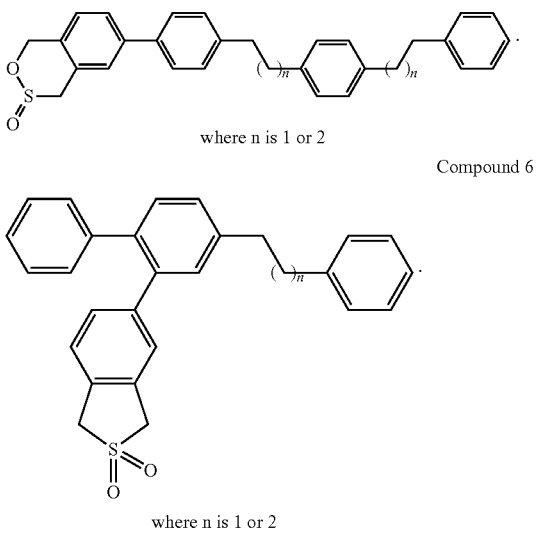

where n is 1 or 2

Compound 6

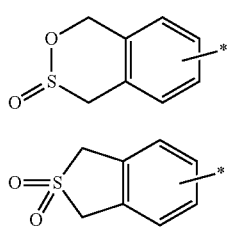

where n is 1 or 2

(vi) Formula IV

In some embodiments, the hole transport composition includes:
(a) a material having at least one triarylamino group; and
(b) a material having Formula IV:

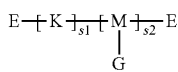 (IV)

wherein:
K is selected from the group consisting of alkyl, aryl, substituted derivatives thereof, and deuterated analogs thereof;
M is selected from the group consisting of alkyl, aryl, substituted derivatives thereof, and deuterated analogs thereof;
E is the same or different at each occurrence and is an end group selected from the group consisting of H. D, halide, alkyl, aryl, deuterated alkyl, and deuterated aryl;
G is selected from the group consisting of G1, G2, and deuterated analogs thereof

G1

G2 where the asterisk represents the point of attachment;
n is an integer greater than 0;
s1 and s2 represent mole fractions, such that s2≠0 and s1+s2=1.

The material having at least one triarylamino group can be any of those discussed above with respect to Formula III.

In Formula IV, the "K" and "M" units can be ordered in a regular alternating pattern, in blocks of like monomers, or randomly arranged.

In some embodiments, the material having Formula IV is deuterated. The deuteration can be present on group K, group M, group E, group G, or combinations thereof. In some embodiments, the material is at least 10% deuterated. In some embodiments, the material is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula IV, K is a monomeric unit derived from an olefin, an acetylenic compound, a stilbene, or a deuterated analog thereof.

In some embodiments of Formula IV, K has formula K-1

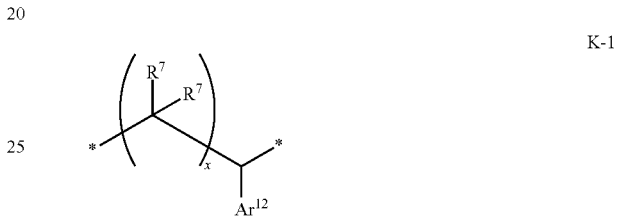 K-1 wherein:
Ar$^{12}$ is selected from the group consisting of carbocyclic aromatic groups having 6-60 ring carbons, substituted carbocyclic aromatic groups having 6-60 ring carbons, and deuterated analogs thereof;
R$^7$ is the same or different at each occurrence and is selected from the group consisting of H, D, F, alkyl, and deuterated alkyl; and
x is an integer from 1-10.

In some embodiments of formula K-1, Ar$^{12}$ is a substituted aryl group having at least one substituent selected Thorn the group consisting of alkyl, alkoxy, silyl, and deuterated analogs thereof.

In some embodiments of formula K-1, Ar$^{12}$ is selected from the group consisting of phenyl, naphthyl, anthracenyl, combinations of such groups linked together covalently, substituted derivatives thereof, and deuterated analogs thereof.

In some embodiments of formula K-1, Ar$^{12}$ is selected from the group consisting of phenyl, biphenyl, terphenyl, substituted derivatives thereof, and deuterated analogs thereof.

In some embodiments of formula K-1, R$^7$ is a C1-3 alkyl group or deuterated analog thereof.

In some embodiments of formula K-1, R$^7$ is selected from the group consisting of H, D, and F.

In some embodiments of formula K-1, x is 1 or 2.

In some embodiments of Formula IV, K has formula K-2

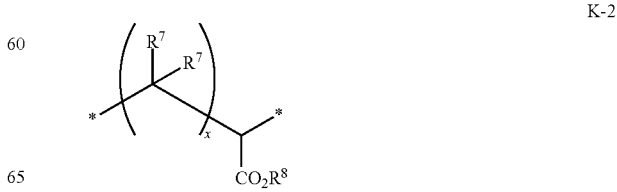 K-2 wherein:

R[7] is the same or different at each occurrence and is selected from the group consisting of H, D, F, alkyl, and deuterated alkyl; and R[8] is selected from the group consisting of alkyl, aryl, and deuterated analogs thereof; and x is an integer from 1-10.

In some embodiments of formula K-2, R[7] is a C1-3 alkyl group or deuterated analog thereof.

In some embodiments of formula K-2, R[7] is selected from the group consisting of H, D, and F.

In some embodiments of formula K-2, R[8] is a C1-3 alkyl group or deuterated analog thereof.

In some embodiments of formula K-2, x is 1 or 2.

In some embodiments of Formula IV, M is a monomeric unit derived from an olefin, an acetylenic compound, a stilbene, or a deuterated analog thereof.

In some embodiments of Formula IV, M has formula M-1

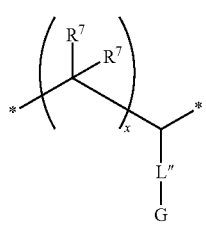

M-1 wherein:

R[7] is the same or different at each occurrence and is selected from the group consisting of H, D, F, alkyl, and deuterated alkyl; and L" is selected from the group consisting of a single bond, an aryl group, and a deuterated aryl group; and x is an integer from 1-10.

In some embodiments of formula M-1-2, R[7] is a C1-3 alkyl group or deuterated analog thereof.

In some embodiments of formula M-1, R[7] is selected from the group consisting of H. D, and F.

In some embodiments of formula M-1, L" is a single bond.

In some embodiments of formula M-1, L" is an aryl group selected from the group consisting of phenyl, biphenyl, naphthyl, and deuterated analogs thereof.

In some embodiments of formula M-1, x is 1 or 2.

In some embodiments of Formula IV, M has formula M-2

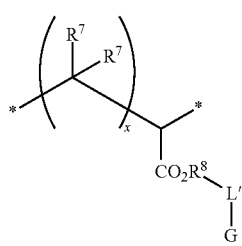

M-2 wherein:

R[7] is the same or different at each occurrence and is selected from the group consisting of H, D, F, alkyl, and deuterated alkyl; and R[8] is selected from the group consisting of alkyl, aryl, and deuterated analogs thereof;

L" is selected from the group consisting of a single bond, an aryl group, and a deuterated aryl group; and x is an integer from 1-10.

In some embodiments of formula M-2, R[7] is a C1-3 alkyl group or deuterated analog thereof.

In some embodiments of formula M-2, R[7] is selected from the group consisting of H, D, and F.

In some embodiments of formula M-2, R[8] is a C1-3 alkyl group or deuterated analog thereof.

In some embodiments of formula M-2, L" is a single bond.

In some embodiments of formula M-2, L" is selected from the group consisting of phenyl, biphenyl, naphthyl, and deuterated analogs thereof.

In some embodiments of formula M-2, x is 1 or 2.

In some embodiments of Formula IV, a is non-zero.

In some embodiments of Formula IV, a>b.

In some embodiments of Formula IV, a=0.60-0.95.

In some embodiments of Formula IV, a=0.70-0.90.

Any of the above embodiments for Formula IV can be combined with one or more of the other embodiments, so long as they are not mutually exclusive. For example, the embodiment in which the material is deuterated can be combined with the embodiment where the K group has formula K-1 and the M group has formula M-1. The same is true for the other non-mutually-exclusive embodiments discussed above. The skilled person would understand which embodiments were mutually exclusive and would thus readily be able to determine the combinations of embodiments that are contemplated by the present application.

The material having Formula IV can be made using known coupling techniques and polymerization techniques.

Some non-limiting examples of material having Formula IV are given below.

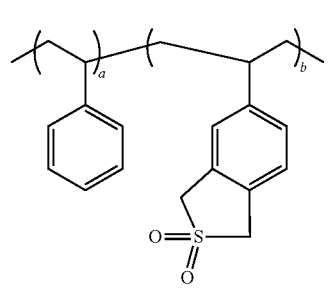

Polymer 1 where a = 0.8 and b = 0.2.

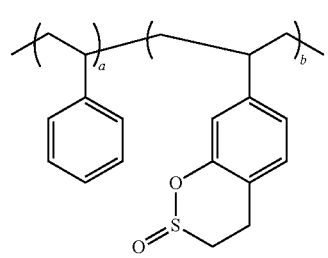

Polymer 2 where a = 0.8 and b = 0.2.

The hole transport composition can include any of the materials having at least one triarylamino group, described above, and any of the materials having Formula IV.

3. Process

There is provided a process to form a hole transport layer having increased solvent resistance.

(i) Formula I

In some embodiments, the process includes the steps:

(1) providing a first liquid composition including a first liquid medium having dispersed therein a material having Formula I:

(I)

wherein:
A is an aromatic moiety including at least one triarylamino group;
G is selected from the group consisting of G1, G2, and deuterated analogs thereof

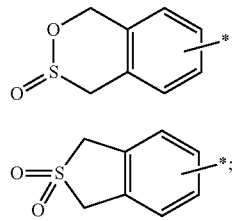

and
n is an integer greater than 0;

(2) depositing the first liquid composition onto a workpiece to form a deposited layer; and (3) baking the deposited layer at a predetermined temperature for a predetermined time to form a hole transport layer.

The first liquid medium is one in which the material having Formula I can be dissolved or dispersed at the desired level, and from which a film can be formed. A suitable liquid medium for a particular material can be readily determined by one skilled in the art.

in some embodiments, the first liquid medium is a polar non-aqueous solvent. Examples of polar solvents include, but are not limited to, $C_1$ to $C_{10}$ alcohols, ethers, and acid esters.

In some embodiments, the first liquid medium is relatively non-polar solvent. Examples of non-polar solvents include, but are not limited to $C_1$ to $C_{12}$ alkanes, aromatics such as toluene, xylenes, trifluorotoluene, and the like.

In some embodiments, the first liquid medium is a mixture of two or more solvents.

In some embodiments, the first liquid medium is selected from the group consisting of a chlorinated hydrocarbon (such as methylene chloride, chloroform, chlorobenzene), an aromatic hydrocarbon (such as a substituted or non-substituted toluene or xylene, including trifluorotoluene), a polar solvent (such as tetrahydrofuran (THF), N-methyl pyrrolidone (NMP)), an ester (such as ethylacetate, methylbenzoate, or diethylphthalate), an ether (such as anisole or dimethoxybenzene), an alcohol (such as isopropanol), a ketone (such as cyclopentanone), and any mixture thereof.

The material having Formula I is generally present in an amount of 0.05 to 10 wt %, based on the total weight of the first liquid composition; in some embodiments, 0.1-5 wt %; in some embodiments 1-4 wt %.

In some embodiments, the material having Formula I is present in an amount of 0.05 to 10% w/v, based on the total volume of the first liquid composition; in some embodiments, 0.1-5% w/v; in some embodiments, 1-4% w/v.

In some embodiments, the workpiece includes a substrate having an electrode thereon. In some embodiments, the electrode is an anode.

In some embodiments, the workpiece includes a substrate having thereon an electrode and one or more organic electroactive layers.

In some embodiments, the workpiece includes a TFT backplane, including electronic components, circuits, and/or conductive members.

In some embodiments, the workpiece includes a TFT backplane and one or more organic electroactive layers thereon.

The first liquid composition is deposited onto the workpiece by any liquid deposition method to form a deposited layer. Liquid deposition techniques include, but are not limited to, spin coating, gravure coating, curtain coating, dip coating, slot-die coating, spray coating, continuous nozzle coating, ink jet printing, gravure printing, and screen printing.

In some embodiments, the first liquid composition is deposited by continuous nozzle coating or ink jet printing.

The deposited layer is then baked to form a first electroactive layer.

In some embodiments, the deposited layer is baked at a temperature less than 350° C. In some embodiments, the baking temperature is less than or equal to 325° C.; in some embodiments, less than or equal to 300° C.; in some embodiments, less than or equal to 275° C.; in some embodiments, less than or equal to 250° C.; in some embodiments, less than or equal to 225° C.; in some embodiments, less than or equal to 200° C.; in some embodiments, less than or equal to 175° C. In general, the baking temperature is at least 100° C.

In some embodiments, the baking step includes two or more different baking stages at different temperatures. When two or more baking stages are used, the highest baking temperature is less than 350° C. In some embodiments, the highest baking temperature is less than or equal to 325° C.; in some embodiments, less than or equal to 300° C.; in some embodiments, less than or equal to 275° C.; in some embodiments, less than or equal to 250° C.; in some embodiments, less than or equal to 225° C.; in some embodiments, less than or equal to 200° C.; in some embodiments, less than or equal to 175° C. In general, the highest baking temperature is at least 100° C.

The predetermined baking time for the deposited layer depends on the baking temperature. The baking time is the time required to remove substantially all of the first liquid medium at the baking temperature selected. By removing "substantially all" it is meant that no detectable liquid medium remains in the deposited layer. In some embodiments, the predetermined time is 30 minutes or less; in some embodiments, 20 minutes or less; in some embodiments, 10 minutes or less. In general, the baking time is at least 5 minutes.

The thus-formed hole transport layer is resistant to mixing with additional liquid media which may be used to coat additional electroactive layers over the hole transport layer. By this it is meant that there is substantially no mixing at the interface between the hole transport layer and the deposited electroactive material.

(ii) Formula Ia

In some embodiments, the process includes the steps:

(1) providing a first liquid composition including a first liquid medium having dispersed therein a material having Formula Ia:

(Ia)

wherein:
A is an aromatic moiety including at least one triarylamino group;
E is the same or different at each occurrence and is selected from the group consisting of H, D, halide, alkyl, aryl, deuterated alkyl, and deuterated aryl;
G is selected from the group consisting of G1, G2, and deuterated analogs thereof

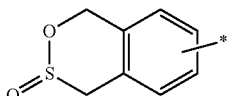
G1

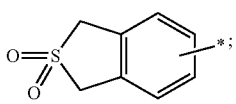
G2 and
n is an integer greater than 0;

(2) depositing the first liquid composition onto a workpiece to form a deposited layer; and (3) baking the deposited layer at a predetermined temperature for a predetermined time to form a hole transport layer.

The first liquid medium is one in which the material having Formula Ia can be dissolved or dispersed at the desired level, and from which a film can be formed. A suitable liquid medium for a particular material can be readily determined by one skilled in the art.

Exemplary liquid media are discussed above with respect to Formula I.

The material having Formula Ia is generally present in an amount of 0.05 to 10 wt %, based on the total weight of the first liquid composition; in some embodiments, 0.1-5 wt %; in some embodiments 1-4 wt %.

In some embodiments, the material having Formula Ia is present in an amount of 0.05 to 10% w/v, based on the total volume of the first liquid composition; in some embodiments, 0.1-5% w/v; in some embodiments, 1-4% w/v.

The workpiece, the deposition method, and the baking are the same as discussed above with respect to Formula I.

The thus-formed hole transport layer is resistant to mixing with additional liquid media which may be used to coat additional electroactive layers over the hole transport layer.

(iii) Formula II

In some embodiments, the process includes the steps:

(1) providing a first liquid composition including a first liquid medium having dispersed therein a material having Formula II

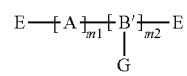
(II)

wherein:
A is an aromatic moiety including at least one triarylamino group;
B' is an aromatic moiety having at least one substituent group selected from the group consisting of G1, G2, and deuterated analogs thereof

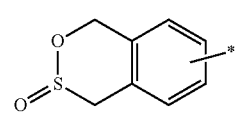
G1

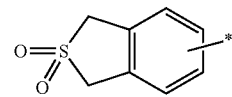
G2

E is the same or different at each occurrence and is an end group selected from the group consisting of H, D, halide, alkyl, aryl, deuterated alkyl, and deuterated aryl; and
m1 and m2 represent non-zero mole fractions, such that m1+m2=1;

(2) depositing the first liquid composition onto a workpiece to form a deposited layer; and (3) baking the deposited layer at a predetermined temperature for a predetermined time to form a hole transport layer.

The first liquid medium is one in which the material having Formula II can be dissolved or dispersed at the desired level, and from which a film can be formed. A suitable liquid medium for a particular material can be readily determined by one skilled in the art.

Exemplary liquid media are discussed above with respect to Formula I.

The material having Formula II is generally present in an amount of 0.05 to 10 wt %, based on the total weight of the first liquid composition; in some embodiments, 0.1-5 wt %; in some embodiments 1-4 wt %, In some embodiments, the material having Formula II is present in an amount of 0.05 to 10% w/v, based on the total volume of the first liquid composition; in some embodiments, 0.1-5% w/v; in some embodiments, 1-4% w/v.

The workpiece, the deposition method, and the baking are the same as discussed above with respect to Formula I.

The thus-formed hole transport layer is resistant to mixing with additional liquid media which may be used to coat additional electroactive layers over the hole transport layer.

(iv) Composition Including Formula III

In some embodiments, the process includes the steps:

(1) providing a first liquid composition including a first liquid medium having dispersed therein a hole transport composition including:
(a) a material having at least one triarylamino group; and
(b) a material having Formula III:

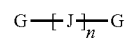
(III)

wherein:
J is an aromatic moiety;
G is selected from the group consisting of G1, G2, and deuterated analogs thereof

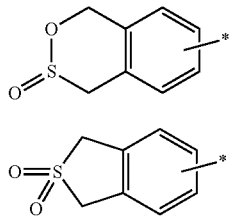

G1

G2 where the asterisk represents the point of attachment; and
n is an integer greater than 0;
(2) depositing the first liquid composition onto a workpiece to form a deposited layer; and
(3) baking the deposited layer at a predetermined temperature for a predetermined time to form a hole transport layer.

The first liquid medium is one in which the hole transport composition can be dissolved or dispersed at the desired level, and from which a film can be formed. A suitable liquid medium for a particular material can be readily determined by one skilled in the art.

Exemplary liquid media are discussed above with respect to Formula I.

The hole transport composition is generally present in an amount of 0.05 to 10 wt %, based on the total weight of the first liquid composition; in some embodiments, 0.1-5 wt %; in some embodiments 1-4 wt %.

In some embodiments, the hole transport composition is present in an amount of 0.05 to 10% w/v, based on the total volume of the first liquid composition; in some embodiments, 0.1-5% w/v; in some embodiments, 1-4% w/v.

The workpiece, the deposition method, and the baking are the same as discussed above with respect to Formula I.

The thus-formed hole transport layer is resistant to mixing with additional liquid media which may be used to coat additional electroactive layers over the hole transport layer.
Composition Including Formula IIIa In some embodiments, the process includes the steps:
(1) providing a first liquid composition including a first liquid medium having dispersed therein a hole transport composition including:
(a) a material having at least one triarylamino group; and
(b) a material having Formula IIIa:

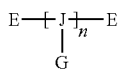

(IIIa)

wherein:
E is the same or different at each occurrence and is an end group selected from the group consisting of H, D, halide, alkyl, aryl, deuterated alkyl, and deuterated aryl;
J is an aromatic moiety;
G is selected from the group consisting of G1, G2, and deuterated analogs thereof

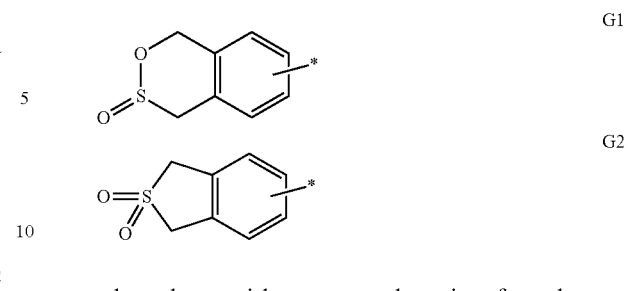

G1

G2 where the asterisk represents the point of attachment; and
n is an integer greater than 0;
(2) depositing the first liquid composition onto a workpiece to form a deposited layer; and
(3) baking the deposited layer at a predetermined temperature for a predetermined time to form a hole transport layer, The first liquid medium is one in which the hole transport composition can be dissolved or dispersed at the desired level, and from which a film can be formed. A suitable liquid medium for a particular material can be readily determined by one skilled in the art.

Exemplary liquid media are discussed above with respect to Formula I.

The hole transport composition is generally present in an amount of 0.05 to 10 wt %, based on the total weight of the first liquid composition; in some embodiments, 0.1-5 wt %; in some embodiments 1-4 wt %, In some embodiments, the hole transport composition is present in an amount of 0.05 to 10% w/v, based on the total volume of the first liquid composition; in some embodiments, 0.1-5% w/v; in some embodiments, 1-4% w/v.

The workpiece, the deposition method, and the baking are the same as discussed above with respect to Formula I.

The thus-formed hole transport layer is resistant to mixing with additional liquid media which may be used to coat additional electroactive layers over the hole transport layer.
(vi) Composition Including Formula IV In some embodiments, the process includes the steps:
(1) providing a first liquid composition including a first liquid medium having dispersed therein a hole transport composition including:
(a) a material having at least one triarylamino group; and
(b) a material having Formula IV:

(IV)

wherein:
K is selected from the group consisting of alkyl, aryl, substituted derivatives thereof, and deuterated analogs thereof;
M is selected from the group consisting of alkyl, aryl, substituted derivatives thereof, and deuterated analogs thereof;
E is the same or different at each occurrence and is an end group selected from the group consisting of H, D, halide, alkyl, aryl, deuterated alkyl, and deuterated aryl;
G is selected from the group consisting of G1, G2, and deuterated analogs thereof

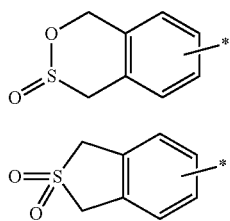

where the asterisk represents the point of attachment;
n is an integer greater than 0;
s1 and s2 represent mole fractions, such that s2≠0 and s1+s2=1;

(2) depositing the first liquid composition onto a workpiece to form a deposited layer; and
(3) baking the deposited layer at a predetermined temperature for a predetermined time to form a hole transport layer.

The first liquid medium is one in which the hole transport composition can be dissolved or dispersed at the desired level, and from which a film can be formed. A suitable liquid medium for a particular material can be readily determined by one skilled in the art.

Exemplary liquid media are discussed above with respect to Formula I.

The hole transport composition is generally present in an amount of 0.05 to 10 wt %, based on the total weight of the first liquid composition; in some embodiments, 0.1-5 wt %; in some embodiments, 1-4 wt %.

In some embodiments, the hole transport composition is present in an amount of 0.05 to 10% w/v, based on the total volume of the first liquid composition; in some embodiments, 0.1-5% w/v; in some embodiments, 1-4% w/v.

The workpiece, the deposition method, and the baking are the same as discussed above with respect to Formula I.

The thus-formed hole transport layer is resistant to mixing with additional liquid media which may be used to coat additional electroactive layers over the hole transport layer.

4. Electronic Devices

In some embodiments, an electronic device includes an anode, a cathode, and a hole transport layer therebetween, wherein the hole transport layer is made from a hole transport material having Formula I, Formula Ia, or Formula II:

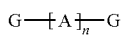  (I)

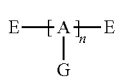  (Ia)

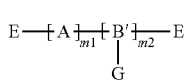  (II)

wherein:
A is an aromatic moiety including at least one triarylamino group;
B' is an aromatic moiety;
E is the same or different at each occurrence and is an end group selected from the group consisting of H, D, halide, alkyl, aryl, deuterated alkyl, and deuterated aryl;
G is selected from the group consisting of G1, G2, and deuterated analogs thereof

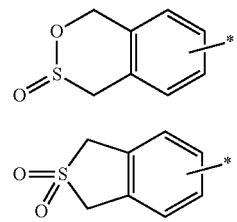

where the asterisk represents the point of attachment;
n is an integer greater than 0;
m1 and m2 represent non-zero mole fractions, such that m1+m2=1.

In some embodiments, an organic electronic device includes an anode, a cathode, and a hole transport layer therebetween, wherein the hole transport layer is made from a hole transport material including:
(a) a material having at least one triarylamino group; and
(b) a material having Formula III, Formula IIIa, or Formula IV:

  (III)

  (IIIa)

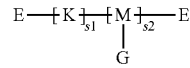  (IV)

wherein:
J is an aromatic moiety;
K is selected from the group consisting of alkyl, aryl, substituted derivatives thereof, and deuterated analogs thereof;
M is selected from the group consisting of alkyl, aryl, substituted derivatives thereof, and deuterated analogs thereof;
E is the same or different at each occurrence and is an end group selected from the group consisting of H, D, halide, alkyl, aryl, deuterated alkyl, and deuterated aryl;
G is selected from the group consisting of G1, G2, and deuterated analogs thereof

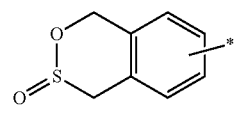

where the asterisk represents the point of attachment;
n is an integer greater than 0;
s1 and s2 represent mole fractions, such that s2≠0 and s1+s2=1.

In some embodiments, the electronic device includes a hole transport layer made according to one of the processes described above.

Organic electronic devices that may benefit from the materials and process as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure is shown in FIG. 1. The device 100 has a first electrical contact layer, an anode layer 110 and a second electrical contact layer, a cathode layer 160, and a photoactive layer 140 between them. In some embodiments, photoactive layer 140 is an electroluminescent layer. Additional layers may optionally be present. Adjacent to the anode may be a hole injection layer 120, sometimes referred to as a buffer layer. Adjacent to the hole injection layer may be a hole transport layer 130, including hole transport material. Adjacent to the cathode may be an electron transport layer 150, including electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the active layers.

Figure 2:
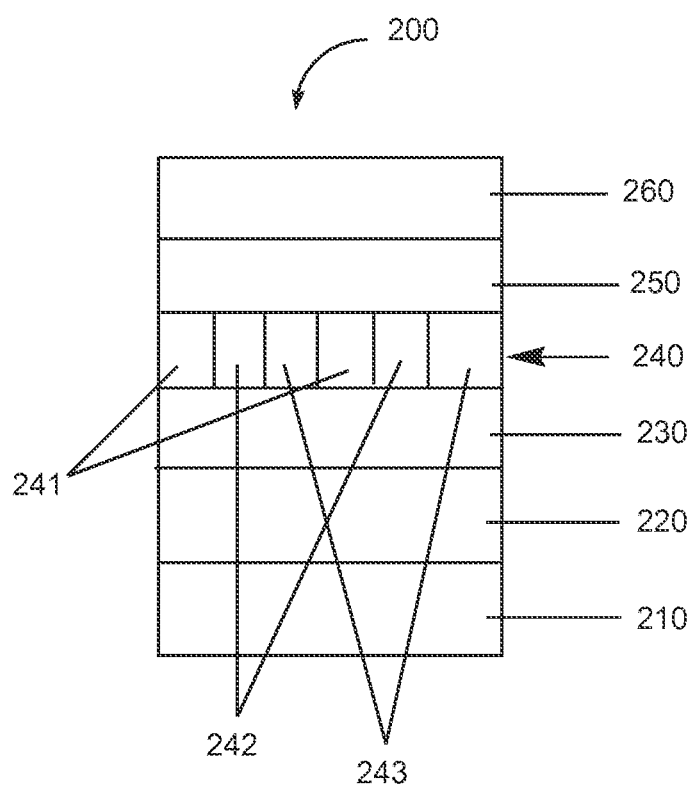
FIG. 2 includes another illustration of an organic electronic device.

In some embodiments, in order to achieve full color, the light-emitting layer is pixellated, with subpixel units for each of the different colors. An illustration of a pixellated device is shown in FIG. 2. The device 200 has anode 210, hole injection layer 220, hole transport layer 230, electroluminescent layer 240, electron transport layer 250, and cathode 260. The electroluminescent layer is divided into subpixels 241, 242, 243, which are repeated across the layer. In some embodiments, the subpixels represent red, blue and green color emission. Although three different subpixel units are depicted in FIG. 2, two or more than three subpixel units may be used.

The different layers will be discussed further herein with reference to FIG. 1. However, the discussion applies to FIG. 2 and other configurations as well.

In some embodiments, the different layers have the following range of thicknesses: anode 110, 500-5000 Å, in one embodiment 1000-2000 Å; hole injection layer 120, 50-2000 Å, in one embodiment 200-1000 Å; hole transport layer 130, 50-2000 Å, in one embodiment 200-1000 Å; electroluminescent layer 140, 10-2000 Å, in one embodiment 100-1000 Å; electron transport layer 150, 50-2000 Å, in one embodiment 100-1000 Å; cathode 160, 200-10000 Å, in one embodiment 300-5000 Å. The desired ratio of layer thicknesses will depend on the exact nature of the materials used.

The hole transport materials and the hole transport composition are useful in layer 130. The processes described above are useful for making the hole transport layer 130, where the layer is resistant to mixing with overcooling solvents.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also be composed of an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

Optional hole injection layer 120 includes hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions.

The hole injection layer can be formed with polymeric materials, such as polyaniline (PAM) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer 120 can include charge transfer compounds, and the like, such as copper phthalocyanine and the tetrathiafulvalene-tetracyanoquinodimethane system (TTF-TCNQ). In some embodiments, the hole injection layer 120 is made from a dispersion of a conducting polymer and a colloid-forming polymeric acid. Such materials have been described in, for example, published U.S. patent applications 2004-0102577, 2004-0127637, and 2005-0205860.

In some embodiments, one or more additional layers of hole transport mated (not shown) can be present. Examples of hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4',4"-tris(N,N-diphenyl-amino)-triphenylamine (TDATA); 4,4',4"-tris(N-3-methylphenyl-N-phenyl-amino)-triphenylamine (MTDATA); N,N'-diphenyl-N,N'-bis(3-methylphenyl)-[1,1'-biphenyl]-4,4'-diamine (TPD); 4,4'-bis(carbazol-9-yl)biphenyl (CBP); 1,3-bis(carbazol-9-yl)benzene (mCP); 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); α-phenyl-4-N,N-diphenylaminostyrene (TPS); p-(diethylamino)benzaldehyde diphenylhydrazone (DEM triphenylamine (TPA); bis[4-(N,N-diethylamino)-2-methylphenyl](4-methylphenyl)methane (MPMP); 1-phenyl-3-[p-(diethylamino)styryl]-5-[p-(dieihylamino)phenyl] pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Depending upon the application of the device, the photoactive layer 140 can be a light-emitting layer that is activated by an applied voltage (such as in a light-emitting diode or light-emitting electrochemical cell), a layer of material that responds to radiant energy and generates a signal with or without an applied bias voltage (such as in a photodetector). In some embodiments, the photoactive layer includes an organic electroluminescent ("EL") material. Any EL material can be used in the devices, including, but not limited to, small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. In some cases the small molecule fluorescent or organometallic materials are deposited as a dopant with one or more host materials to improve processing and/or electronic properties. Examples of host materials include, but are not limited to, chrysenes, phenanthrenes, triphenylenes, phenanthrolines, naphthalenes, anthracenes, quinolines, isoquinolines, quinoxalines, phenylpyridines, benzodifurans, and metal quinolinate complexes. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Optional layer 150 can function both to facilitate electron transport, and also serve as a hole injection layer or confinement layer to prevent quenching of the exciton at layer interfaces. Preferably, this layer promotes electron mobility and reduces exciton quenching. Examples of electron transport materials which can be used in the optional electron transport layer 150, include metal chelated oxinoid compounds, including metal quinolate derivatives such as tris (8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole) benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, $Li_2O$, Cs-containing organometallic compounds, CsF, $Cs_2O$, and $Cs_2CO_3$ can also be deposited between the organic layer and the cathode layer to lower the operating voltage. This layer may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

In some embodiments, the device is fabricated by liquid deposition of the hole injection layer, the hole transport layer, and the photoactive layer, and by vapor deposition of the anode, the electron transport layer, an electron injection layer and the cathode.

It is understood that the efficiency of devices made with the new compositions described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In some embodiments, the device has the following structure, in order: anode, hole injection layer, hole transport layer, photoactive layer, electron transport layer, electron injection layer, cathode, Although methods and materials similar or equivalent to those described herein can be used in the practice or testing of the present invention, suitable methods and materials are described below. In addition, the materials, methods, and examples are illustrative only and not intended to be limiting.

EXAMPLES

The concepts described herein will be further described in the following examples, which do not limit the scope of the invention described in the claims.

Synthesis Example 1

This example illustrates the preparation of hole transport material having Formula I, HT8.

Step 1:

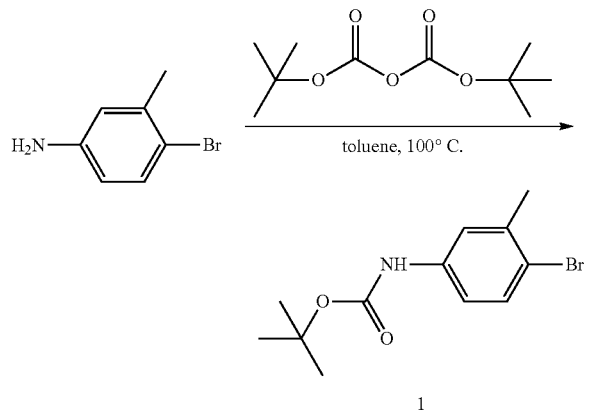

The reaction mixture of 4-bromo-3-methylaniline (11 g, 59 12 mmol) and (Boc)$_2$O (12.9 g, 59.12 mmol) in toluene (110 ml) was stirred at 100° C. for 40 h under nitrogen. After concentration of the reaction mixture under reduced pressure, 15.9 g (94% yield) of boc-NH-4-bromo-3-methylaniline, 1, was obtained as a white solid by column chromatography (5-10% ethyl acetate in hexane).

Step 2:

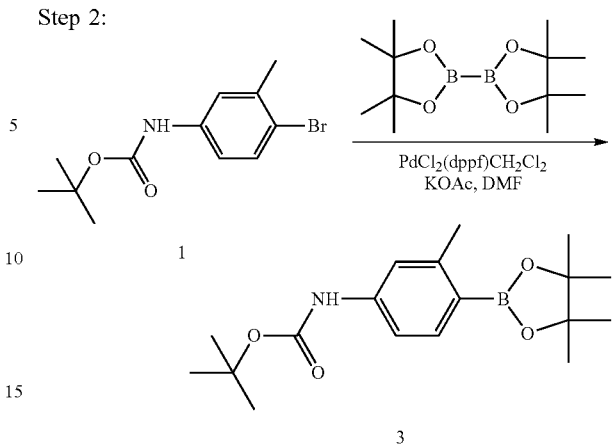

In a glove box a mixture at the boc-NH-4-bromo-3-methylaniline, 1, (20.77 g, 72.58 mmol), diboron pinacol ester (22.12 g, 87.09 mmol), 1,1'-bis-(diphenylphosphino)ferrocine palladium dichloride (1.43 g, 1.96 mmol), and potassium acetate (21.37 g, 217.7 mmol) in dry degassed DMF (300 mL) was stirred at 80° C. for 16 hrs in an oil bath. The mixture was cooled to room temperature and concentrated under reduced pressure. DCM (100 mL) was added to the mixture which was filtered through a pad of Celite. The filtrate was concentrated to rusty oil which was purified on a silica gel column chromatography (5-10% EtOAc/hexane) to provide the product, 3, (18.57 g, 77% yield) as a white solid.

Step 3:

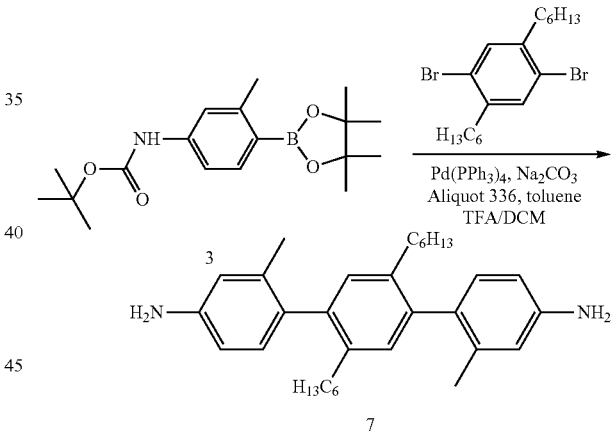

In the dry box the mixture of boronic acid pinacol ester, 3, (5.6 g, 16.82 mmol), 1,4-dibromo-2,5- dihexylbenzene (3.4 g, 8.4 mmol), Aliquat 336 (0.8 g), and Pd(PPh$_3$)$_4$ (0.486 g, 0.421 mmol) in degassed toluene (100 mL) was prepared. Outside dry box, the degassed Na$_2$CO$_3$ (2.67 g, 25.23 mmol in 50 mL of water) solution was added to the former mixture under nitrogen, and then the resultant mixture was stirred at 90° C. for 42 hrs. The organic, layer was separated and the aqueous layer was extracted with ethyl acetate. The combined organic layers were dried over anhydrous MgSO$_4$. Filtration, concentration of the filtrate, and then the silica column chromatography (0-3% ethyl acetate in hexane) provided the desired product (2.11 g, 38% yield) as a viscous liquid. This diboc-protected material was deprotected by the overnight reaction at room temperature with TFA solution (5 mL of TEA in 50 mL of DCM). Concentration of the reaction mixture followed by the neutralization with saturated NaHCO$_3$, then silica column chromatography (30% ethylacetate in hexane) provided the desired diamine material, 7, (1.16 g, 80% yield) as a viscous liquid, Step 4:

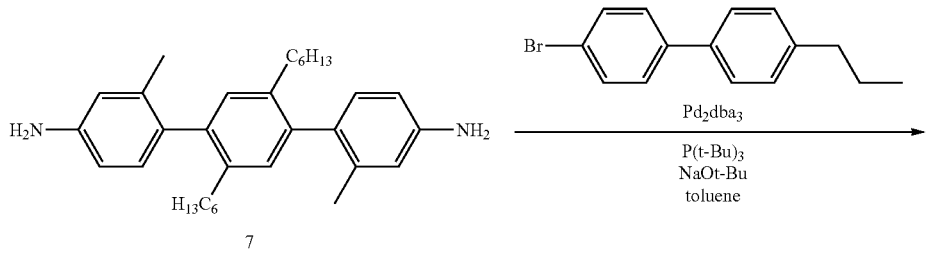

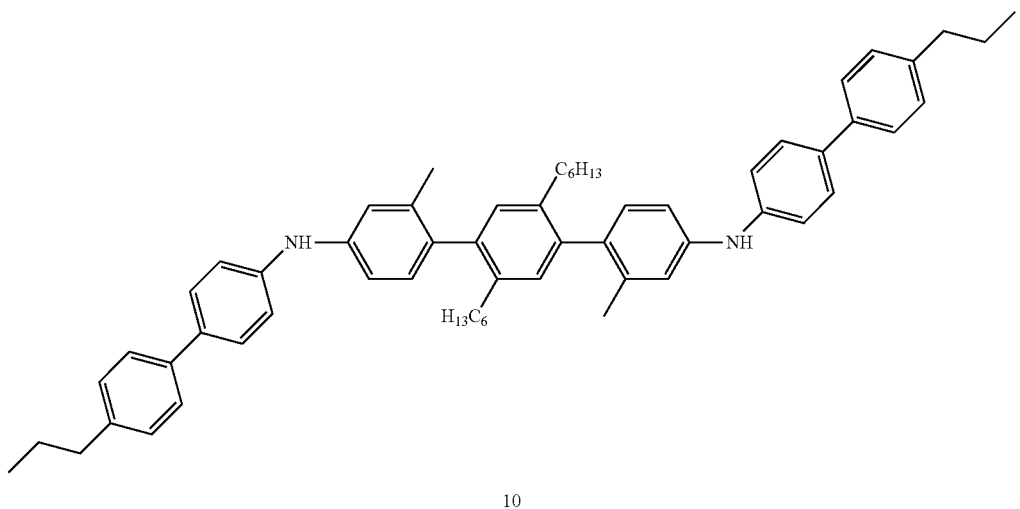

To the solution of diamine, 7, (1.06 g, 2.32 mmol) and 4-bromo-4'-propyl-biphenyl (1.28 g, 4.65 mmol) in toluene (20 mL) was added the solution of pd$_2$dba$_3$ (128 mg, 0.139 mmol) and P(t-Bu)$_3$ (57 mg, 0.278 mmol) in toluene (10 mL), followed by the addition of NaOt-Bu (0.45 g, 4.65 mmol) under nitrogen. The resultant mixture was stirred at room temperature overnight. The mixture was filtered through a short silica bed and the filtrate was concentrated under reduced pressure. By column chromatography (10-30% toluene in hexane) 1.35 g of product 10 was obtained as a solid (69% yield).

Step 5:

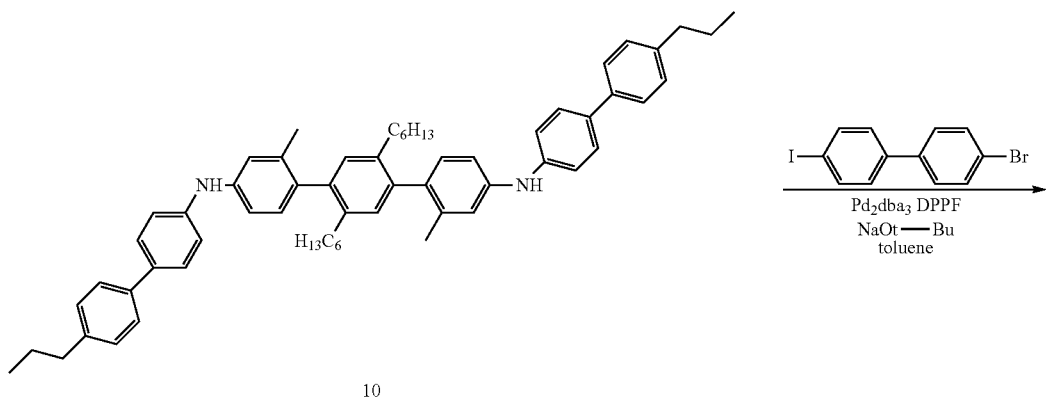

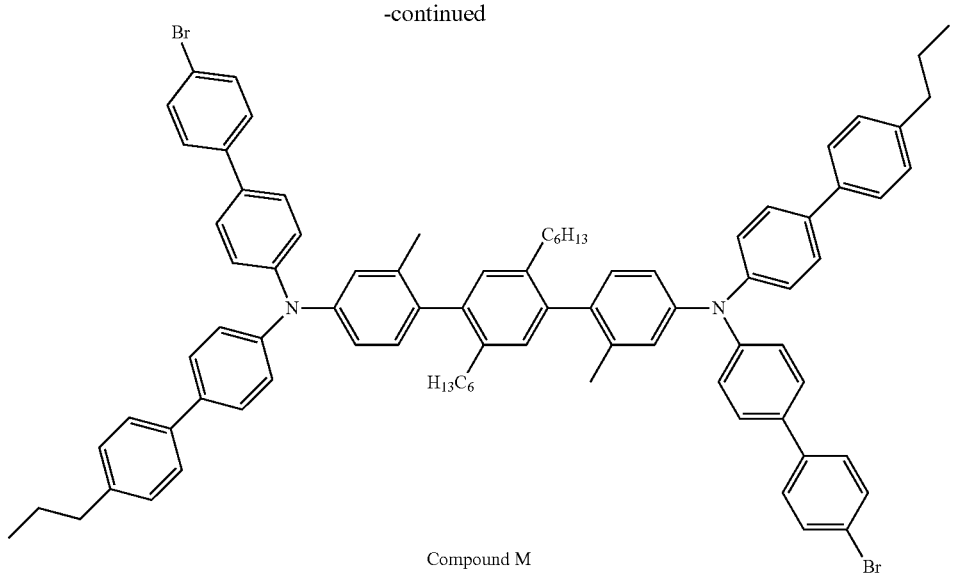

Compound M

To the solution of diamine, 10, (1.25 g, 1.48 mmol) and 4-bromo-4'-iodobiphenyl (1.59 g, 4.44 mmol) in toluene (30 mL) was added the solution of pd$_2$dba$_3$ (37 mg, 0.04 mmol) and DPPF (43 mg, 0.078 mmol) in toluene (10 mL), followed by the addition of NaOt-Bu (0.355 g, 3.70 mmol) under nitrogen. The resultant mixture was stirred at 95° C. for 16 hrs. The mixture was filtered through a short silica bed and the filtrate was concentrated under reduced pressure. By column chromatography (0-12% toluene in hexane) 1.10 g of product, Compound M, was obtained as a solid (57% yield).

Step 6:

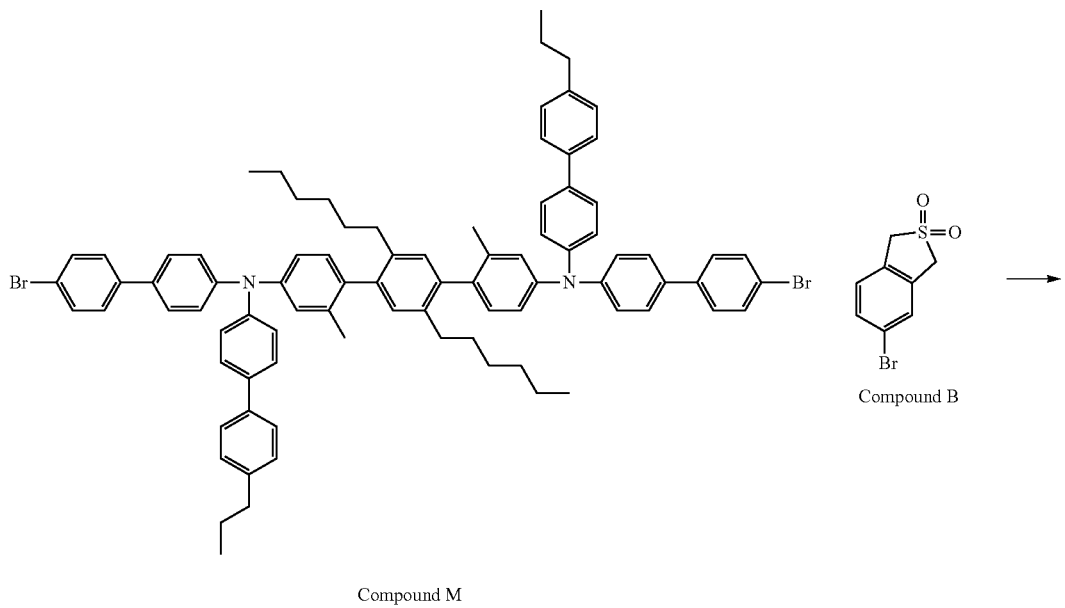

Compound M        Compound B

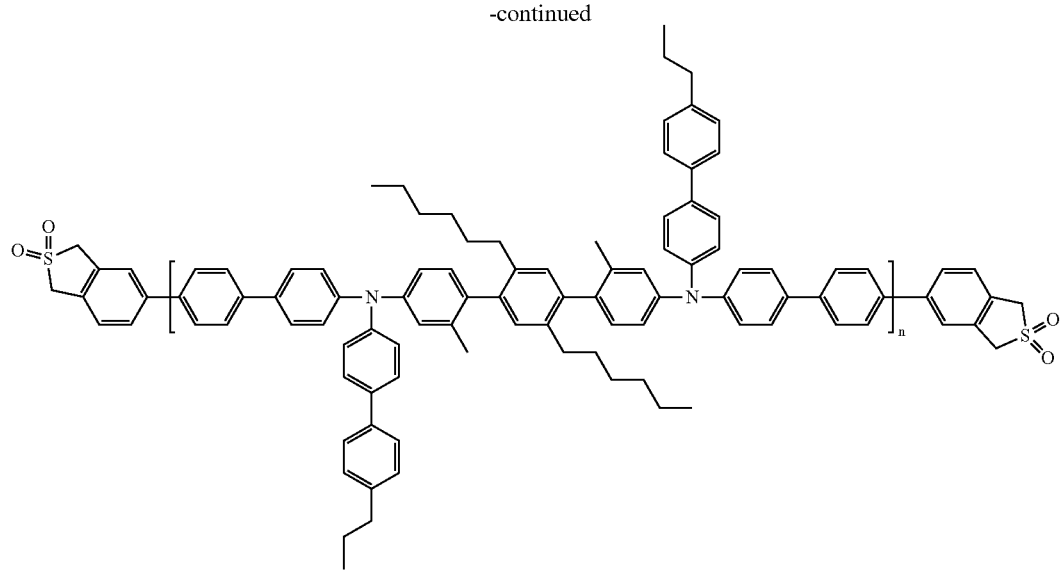
Compound M (0.370 mmol) and compound B (0.030 mmol) we added to a scintillation vial and dissolved in 12 mL toluene. A clean, dry 50 mL Schlenk tube was charged with bis(1,5-cyclooctadiene)nickel(0) (0.808 mmol), 2,2'-Dipyridyl (0.808 mmol) and 1,5-cyclooctadiene (0.808 mmol)
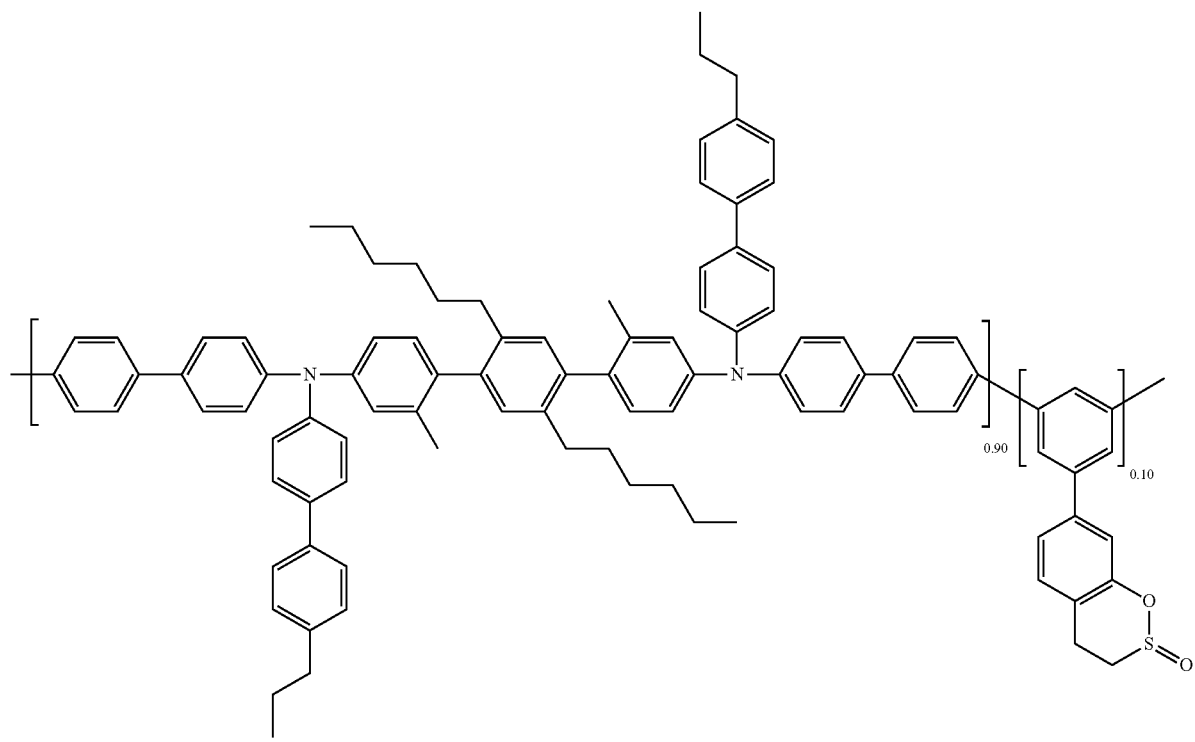

Synthesis Example 4

This illustrates how a material having Formula III, Compound 1, could be prepared.

Compound 1

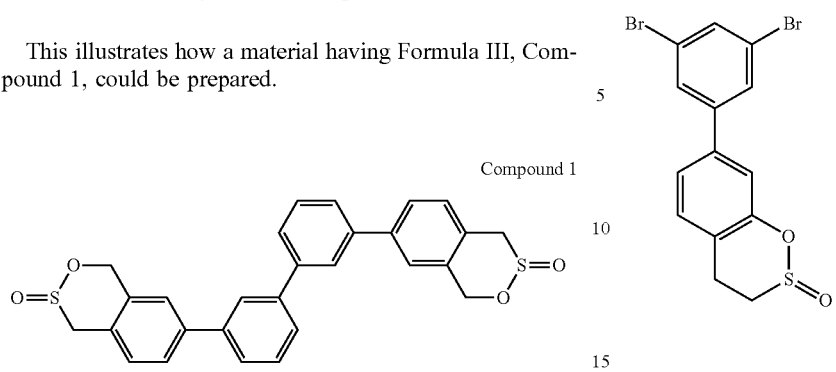

Synthesis of Compound 1

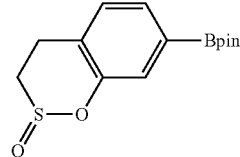

Compound G-Bpin

+

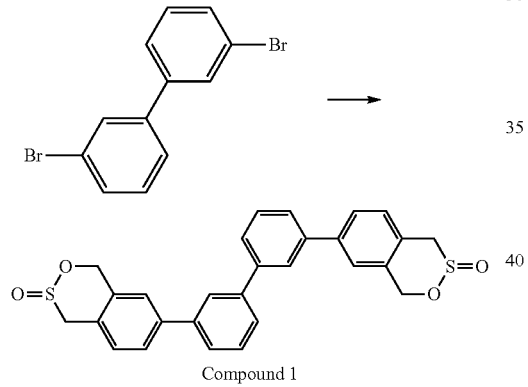

Compound 1

Compound 1 will be synthesized by reaction compound G-Bpin with 0.5 equivalents of 3,3dibromebiphenyl in a two-to-one mixture of toluene and water using Pd(PPh3)4 as the catalyst and K2CO3 (six equivalents) as the base. The mixture wilt be heated to reflux until the starting materials are consumed. The product will be isolated by cooling at room temperature, separating the layers and purifying the organic layer using silica chromatography.

Synthesis Example 5

This illustrates how a hole transport material having Formula IV could be prepared.

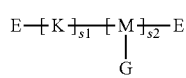
(IV)

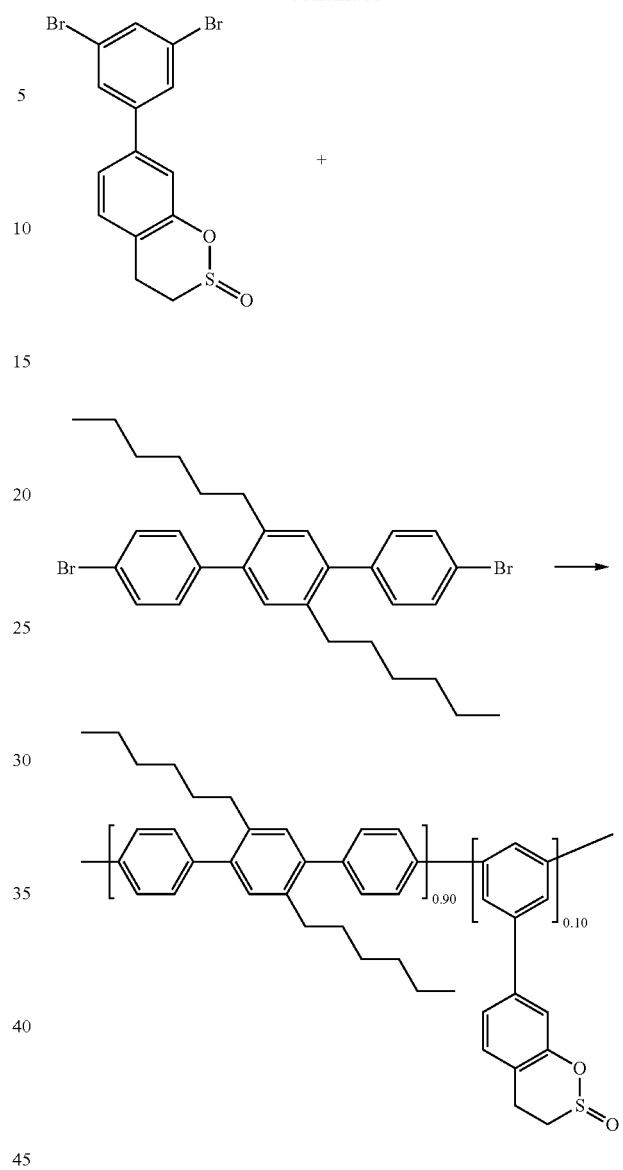

Synthesis of Compound E5

Compound E5 will be synthesized using the procedure of Synthesis Example 1, where compound 3A will be used instead of compound B in a ratio of M to 3A of 9 to 1 to yield the above polymer.

Synthesis Example 6

This example illustrates how a compound of Formula Ia could be prepared.

(Ia)

Compound E6a will be synthesized using the procedure outlined in the scheme below:

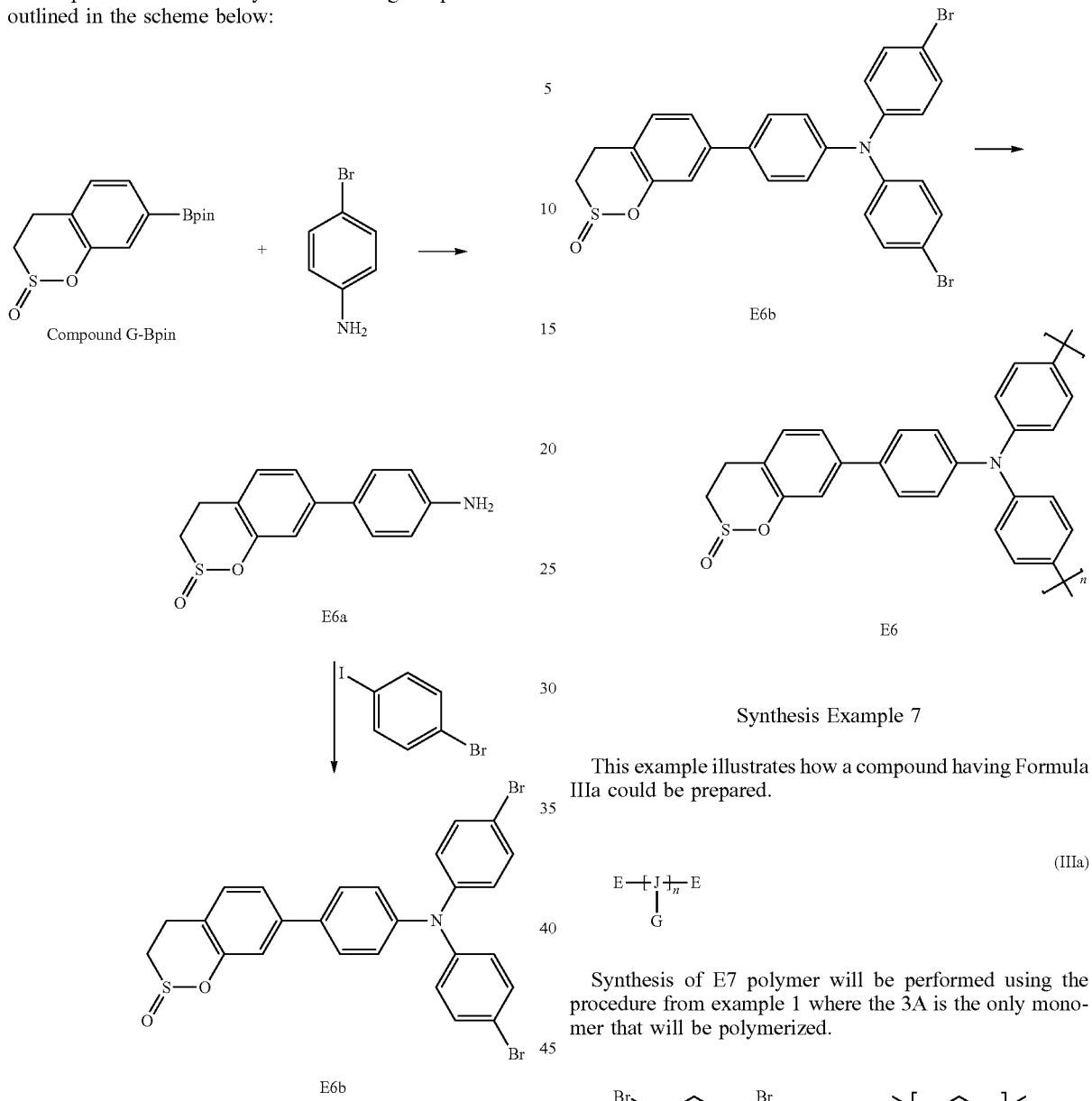

Compound E6a will be synthesized by reaction Compound G-Bpin with 1.1 equivalents of 4-/bromo-aniline in a two-to-one mixture of toluene and water using Pd(PPh3)4 as the catalyst and K2CO3 (three equivalents) as the base. The mixture will be heated to reflux until the starting materials are consumed. The product will be isolated by cooling at room temperature separating the layers and purifying the organic layer using silica chromatography.

Compound E6b will be synthesized by reacting E6A with 1.2 equivalents of iodobromo benzene in toluene with Pd2(dba)2 and dppf as the catalyst system and NaOtBu as the base. The reaction mixture will be heated to 90 C until it is completed and the product will be purified using silica chromatography.

Synthesis of E6 will be performed using procedure outlines in Example 1 except that E6b will be the only monomer to yield E6.

Synthesis Example 7

This example illustrates how a compound having Formula IIIa could be prepared.

(IIIa)

Synthesis of E7 polymer will be performed using the procedure from example 1 where the 3A is the only monomer that will be polymerized.

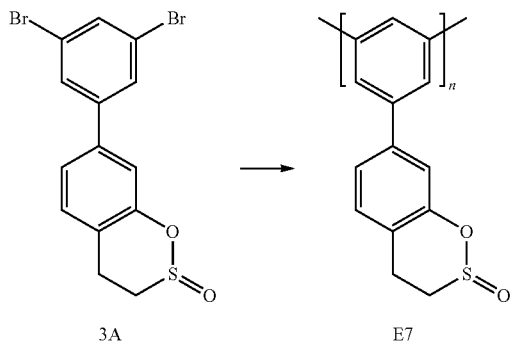

OLED Devices
(1) Materials
HIJ-1 is an electrically conductive polymer doped with a polymeric fluorinated sulfonic acid.
HT-A is a copolymer of a triarylamine and a fluorene
Host-1 is a deuterated diaryl anthracene compound.

E-1 is a deuterated bis(diarylamino)chrysene

ET-1 is a diarylfluoranthene compound.

EIJ-1 is a metal quinolate compound.

The devices had the following structure on a glass substrate:

anode=ITO (50 nm)

hole injection layer=HIJ-1 (100 nm)

first hole transport layer=HT-1 (10 nm)

second hole transport layer=discussed below photoactive layer=Host-1:E-1 in 93:7 weight ratio (43 nm), electron transport layer=ET-1 (20 nm)

electron injection layer/cathode=EIJ-1/Al (3/100 nm)

(2) Device Fabrication (SCOLEDT)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission.

The patterned ITO substrates were cleaned and spin-coated with an aqueous dispersion of a hole injection material (HIJ-1). A first hole transport layer was formed by spin-coating a solution of HT-A in toluene (0.4% w/v). After heating to remove solvent, the layer was exposed to UV light, rinsed with anisole, and heated to dry. After cooling, a second hole transport layer was formed by spin-coating a solution of hole transport material in anisole (2.0% w/v). The hole transport layer was baked as indicated. The workpieces were then spin-coated with a solution of the photoactive layer materials in methyl benzoate and heated to remove solvent. The workpieces were masked and placed in a vacuum chamber. A layer of electron transport material (ET-1) was deposited by thermal evaporation, followed by a layer of electron injection material (EIJ-1). Masks were then changed in vacuo and a layer of Al was deposited by thermal evaporation. The chamber was vented, and the devices were encapsulated using a glass lid, desiccant, and UV curable epoxy.

(3) Device Characterization

The OLED samples were characterized by measuring their (1) current-voltage (I-V) curves, (2) electroluminescence luminance versus voltage, and (3) electroluminescence spectra versus voltage. All three measurements were performed at the same time and controlled by a computer. The current efficiency of the device at a certain voltage is determined by dividing the electroluminescence luminance of the LED by the current density needed to run the device. The unit is a cd/A. The color coordinates were determined using either a Minolta CS-100 meter or a Photoresearch PR-705 meter.

Device Examples 1-3

These examples illustrate the preparation of devices including a hole transport layer made from a material having Formula I.

The materials and conditions for the second hole transport layer are given in Table 1 below.

The device results are given in Table 2.

TABLE 1

| | Second Hole Transport Layer | | |
| --- | --- | --- | --- |
| Example | Material | Thickness (nm) | Baking Temperature (° C.) |
| 1 | HT8 | 100 | 295 |
| 2 | HT8 | 100 | 250 |
| 3 | HT9/HT10* | 130 | 295 |

*from Synthesis Example 2

TABLE 2

| | Device results | | | |
| --- | --- | --- | --- | --- |
| Example | Voltage @ 15 mA/cm$^2$ | E.Q.E. (%) | C.E. (cd/A) | P.E. (lm/W) |
| 1 | 6.3 | 5.8 | 4.6 | 2.2 |
| 2 | 6.1 | 1.3 | 1.3 | 0.5 |
| 3 | 15.3 | 1.0 | 1.5 | 0.3 |

All data @ 1000 nits.
EQE is the external quantum efficiency;
CE is the current efficiency;
P.E. is the power efficiency.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within

What is claimed is:

1. A hole transport material having Formula I, Formula Ia, or Formula II:

$$G-(A)_n-G \quad (I)$$

$$E-(A)_n-E \\ \phantom{E-(A}|\phantom{)}\\ \phantom{E-(A)}G \quad (Ia)$$

$$E-(A)_{m1}-(B')_{m2}-E \\ \phantom{E-(A)_{m1}}|\phantom{)}\\ \phantom{E-(A)_{m1}-(}G \quad (II)$$

wherein:

A is selected from the group consisting of formula A-2, formula A-3, and formula A-4

$$\left[ \begin{array}{c} Ar^{4a} \diagdown_{N} \diagup Ar^{5a} \\ |_{n1} \\ *-Ar^3 \diagdown_N \diagup L \diagdown_N \diagup X \\ | \quad\quad | \\ Ar^4 \quad Ar^5 \end{array} \right]_n -* \quad A\text{-}2$$

wherein:

Ar$^3$, Ar$^4$, Ar$^{4a}$, Ar$^5$ and Ar$^{5a}$ are the same or different and are aryl groups;

L is the same or different at each occurrence and is aryl, (CR'2)q, adamantyl, bicyclic cyclohexyl, or a bicyclic group having aliphatic rings connected through a single atom;

R' is the same or different at each occurrence and is H, D, alkyl, fluoroalkyl, aryl, deuterated alkyl, deuterated fluoroalkyl, and deuterated aryl;

X is the same or different at each occurrence and is selected from an aryl group, and a deuterated aryl group, with the proviso that N is not bonded directly to G;

n is an integer greater than 0;

n1 is 0 or 1;

q is an integer from 1-5; and

In Formula Ia, G is bonded directly or through a substituent group to one or more of Ar$^4$, Ar$^{4a}$, Ar$^5$, or Ar$^{5a}$ A-3: *—((R$^1$)$_a$ phenyl)$_f$—N(Ar$^6$)—((R$^2$)$_b$ phenyl)—((R$^3$)$_c$ phenyl)$_g$ A-4 continued: (R$^4$)$_d$ phenyl—N(Ar$^7$)—((R$^5$)$_e$ phenyl)$_h$—* wherein:

Ar$^6$ and Ar$^7$ are the same or different and are aryl groups;

R$^1$ through R$^5$ are independently the same or different at each occurrence and are selected from the group consisting of D, F, alkyl, aryl, alkoxy, silyl, deuterated alkyl, deuterated aryl, deuterated alkoxy, and deuterated silyl;

a through e are independently an integer from 0 to 4;

f is 1 or 2;

g is 0, 1 or 2;

h is 1 or 2; and

In Formula Ia, G is bonded directly or through a substituent group to one or more of Ar$^6$, Ar$^7$, R$^2$, R$^3$, R$^4$ or R$^5$ $$*—(Ar^8)_k\diagdown_N\diagup(Ar^8)_l—[T^1—T^2]—(Ar^8)_l\diagdown_N\diagup(Ar^8)_k—* \quad A\text{-}4 \\ \phantom{*—(Ar^8)_k\diagdown_N}|\phantom{(Ar^8)_l—[T^1—T^2]—(Ar^8)_l\diagdown_N}|\\ \phantom{*—(Ar^8)_k\diagdown_}Ar^9 \phantom{(Ar^8)_l—[T^1—T^2]—(Ar^8)_l\diagdown_}Ar^9$$

wherein:

Ar$^8$ is the same or different at each occurrence and is selected from the group consisting of phenylene, substituted phenylene, naphthylene, substituted naphthylene, and deuterated analogs thereof;

Ar$^9$ is the same or different at each occurrence and is an aryl group;

T$^1$ and T$^2$ are independently the same or different at each occurrence and are conjugated moieties which are connected in a non-planar configuration;

k is the same or different at each occurrence and is an integer from 1 to 6;

l is the same or different at each occurrence and is an integer from 1 to 6; and In Formula Ia, G is bonded directly or through a substituent group to one or more of Ar$^8$ or Ar$^9$;

B' is an aromatic moiety;

E is the same or different at each occurrence and is an end group selected from the group consisting of H, D, halide, alkyl, aryl, deuterated alkyl, and deuterated aryl;

G is selected from the group consisting of G1, G2, and deuterated analogs thereof G1: isochromane-S,S-dioxide-type structure (O=S(=O) fused bicyclic with O in ring)

G2: isothiazole/benzo-fused S,S-dioxide structure (O=S=O)

where the asterisk represents the point of attachment;
n is an integer greater than 0; and
m1 and m2 represent non-zero mole fractions, such that m1+m2=1.

2. The hole transport material of claim 1 having Formula I.

3. The hole transport material of claim 1 having Formula Ia.

4. The hole transport material of claim 1 having Formula II.

5. The hole transport material of claim 1, wherein G is selected from the group consisting of G1-a, G1-b, G1-c, G1-d, and mixtures thereof

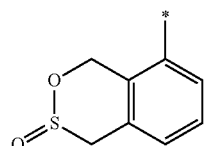
G1-a

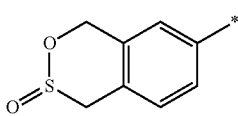
G1-b

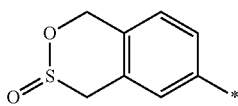
G1-c

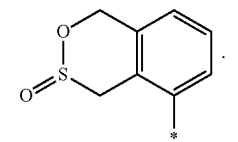
G1-d

6. The hole transport material of claim 5, wherein G is selected from the group consisting of G1-b, G1-c, and mixtures thereof.

7. The hole transport material of claim 1, wherein G is selected from the group consisting of G2-a, G2-b, and mixtures thereof

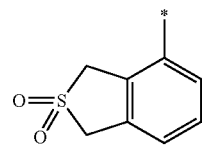
G2-a

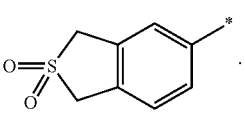
G2-b

8. The hole transport material of claim 7, wherein G is G2-b.

9. A hole transport material having Formula Ia or Formula II:

(Ia)

(II)

wherein:
A has formula A-1

A-1 wherein:
$Ar^1$-$Ar^2$ are the same or different and are aryl groups; and
X is the same or different at each occurrence and is selected from an aryl group, and a deuterated aryl group, with the proviso that N is not bonded directly to G; and
in Formula Ia, G is bonded directly or through a substituent group to $Ar^2$;
B' is an aromatic moiety;
E is the same or different at each occurrence and is an end group selected from the group consisting of H, D, alkyl, aryl, deuterated alkyl, and deuterated aryl;
G is selected from the group consisting of G1, G2, and deuterated analogs thereof

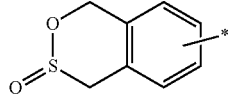
G1

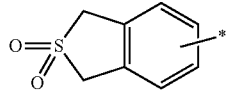
G2 where the asterisk represents the point of attachment;
n is an integer greater than 0; and
m1 and m2 represent non-zero mole fractions, such that m1+m2=1.

10. The hole transport material of claim 1, wherein B' has formula B-1

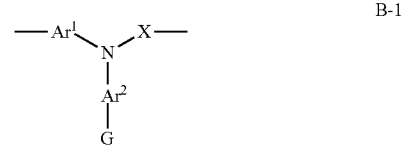
B-1 wherein:
$Ar^1$-$Ar^2$ are the same or different and are aryl groups; and
X is the same or different at each occurrence and is selected from a single bond, an aryl group, and a deuterated aryl group.

11. The hole transport material of claim 1, wherein B' has formula B-2

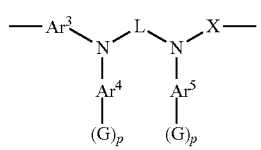

B-2 wherein:
Ar³-Ar⁵ are the same or different and are aryl groups;
L is the same or different at each occurrence and is aryl, (CR'2)q, adamantyl, bicyclic cyclohexyl, or a bicyclic group having aliphatic rings connected through a single atom;
R' is the same or different at each occurrence and is H, D, alkyl, fluoroalkyl, aryl, deuterated alkyl, deuterated fluoroalkyl, and deuterated aryl;
X is the same or different at each occurrence and is selected from a single bond, an aryl group, and a deuterated aryl group;
p is the same or different at each occurrence and is 0 or 1, with the proviso that at least one p=1; and
q is an integer from 1-5.

12. The hole transport material of claim 1, wherein B' has formula B-3

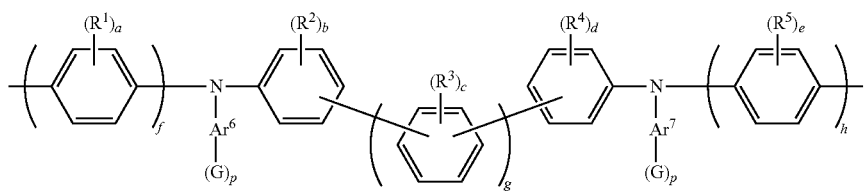

B-3 wherein:
Ar⁶ and Ar⁷ are the same or different and are aryl groups;
R¹ through R⁵ are independently the same or different at each occurrence and are selected from the group consisting of D, F, alkyl, aryl, alkoxy, silyl, deuterated alkyl, deuterated aryl, deuterated alkoxy, and deuterated silyl;
a through e are independently an integer from 0 to 4;
f is 1 or 2;
g is 0, 1 or 2; h is 1 or 2; and
p is the same or different at each occurrence and is 0 or 1, with the proviso that at least one p=1.

13. The hole transport material of claim 1, wherein B' has formula B-4

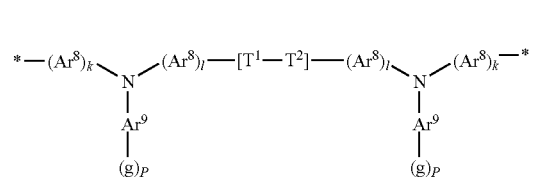

b-4 wherein:
Ar⁸ is the same or different at each occurrence and is selected from the group consisting of phenylene, substituted phenylene, naphthylene, substituted naphthylene, and deuterated analogs thereof;
Ar⁹ is the same or different at each occurrence and is an aryl group;
T¹ and T² are independently the same or different at each occurrence and are conjugated moieties which are connected in a non-planar configuration;
k is the same or different at each occurrence and is an integer from 1 to 6; and
p is the same or different at each occurrence, with the proviso that at least one p=1.

14. A hole transport material having Formula I:

(I)

wherein:
A is formula A-1

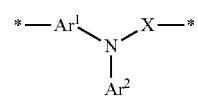

A-1 wherein:

Ar¹-Ar² are the same or different and are aryl groups;
X is the same or different at each occurrence and is selected from an aryl group, and a deuterated aryl group, with the proviso that N is not bonded directly to G; and
G is selected from the group consisting of G1, G2, and deuterated analogs thereof

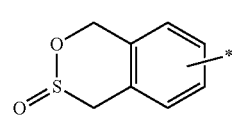

G1

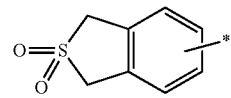

G2 where the asterisk represents the point of attachment;
n is an integer greater than 2; and
m1 and m2 represent non-zero mole fractions, such that m1+m2=1.

15. The hole transport material of claim 1, wherein the hole transport material is selected from the group consisting of following compounds:

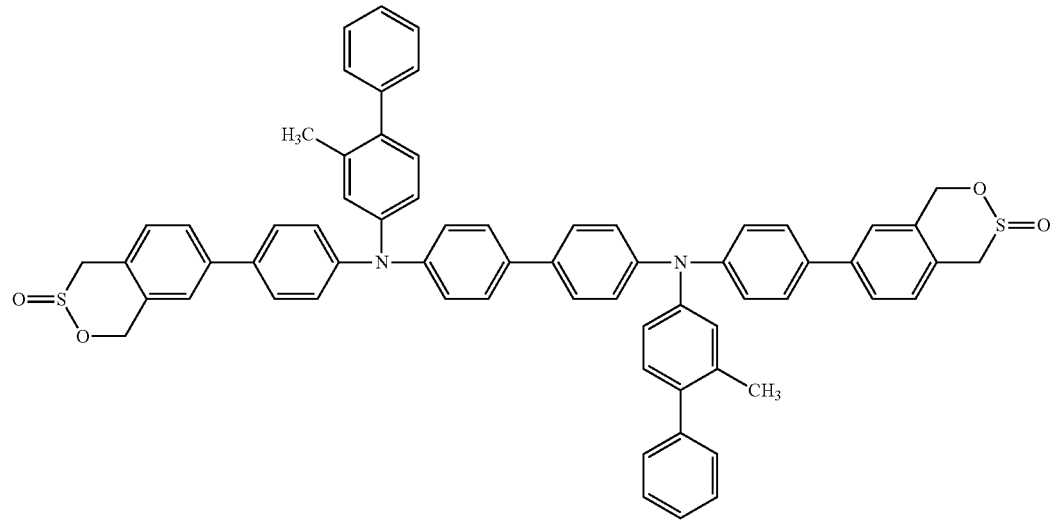
HT2
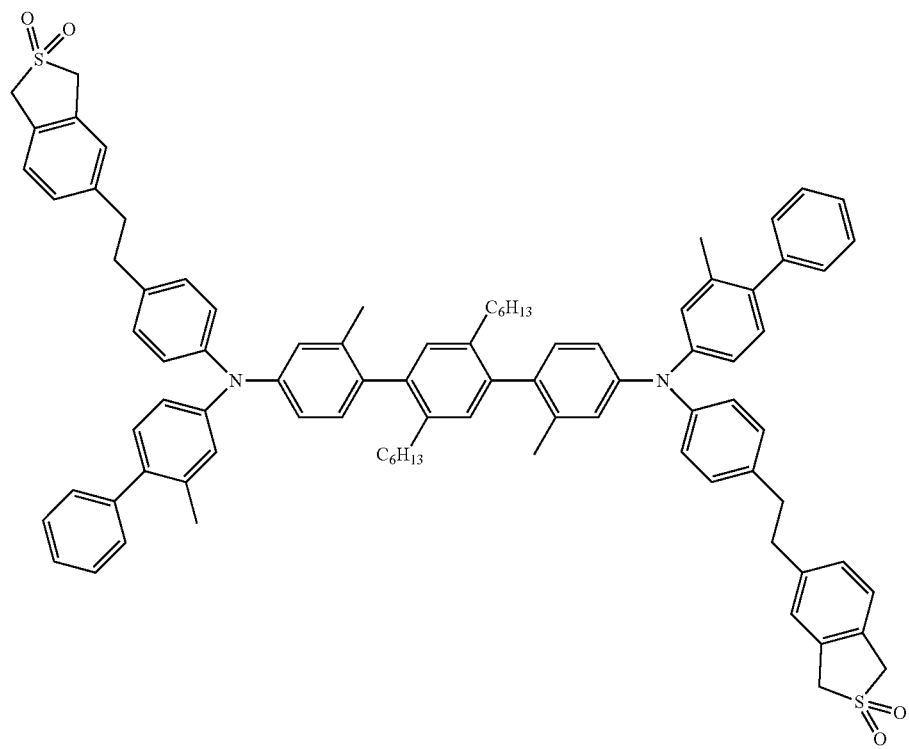
HT3

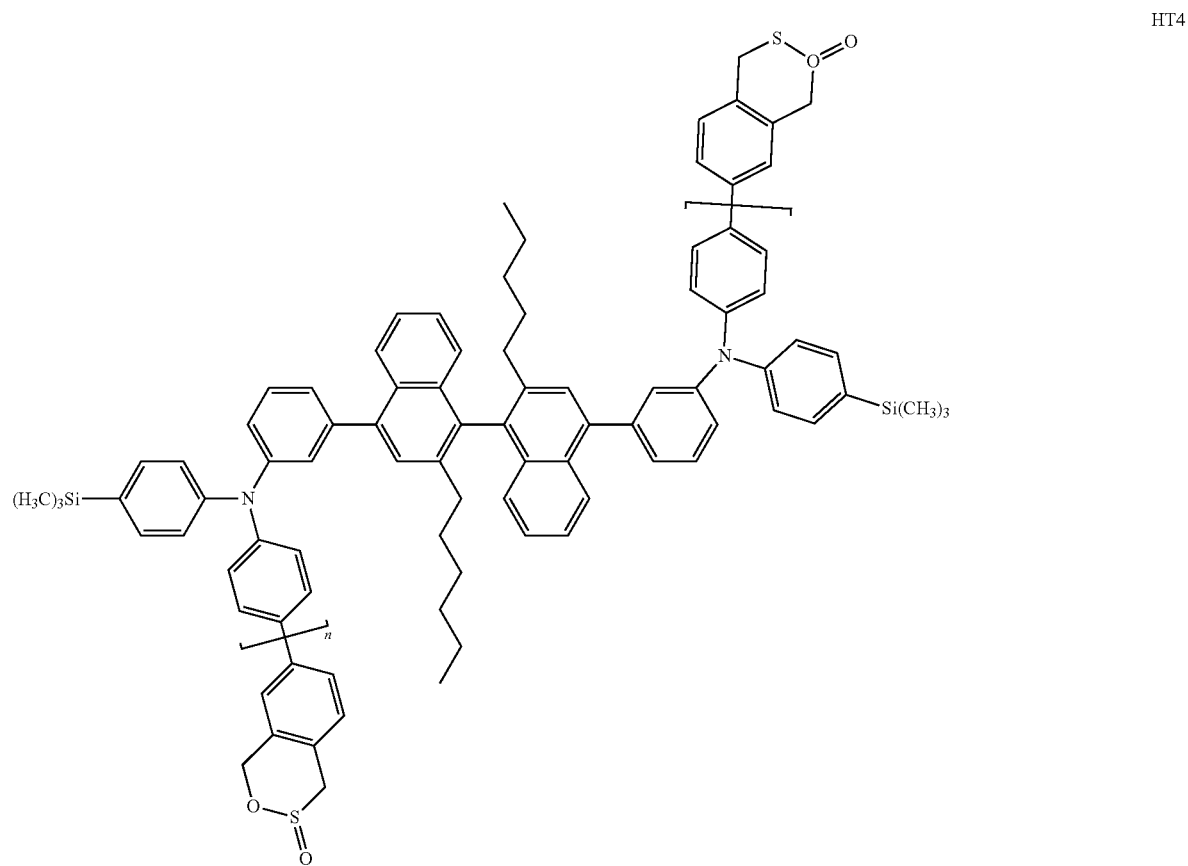
HT4
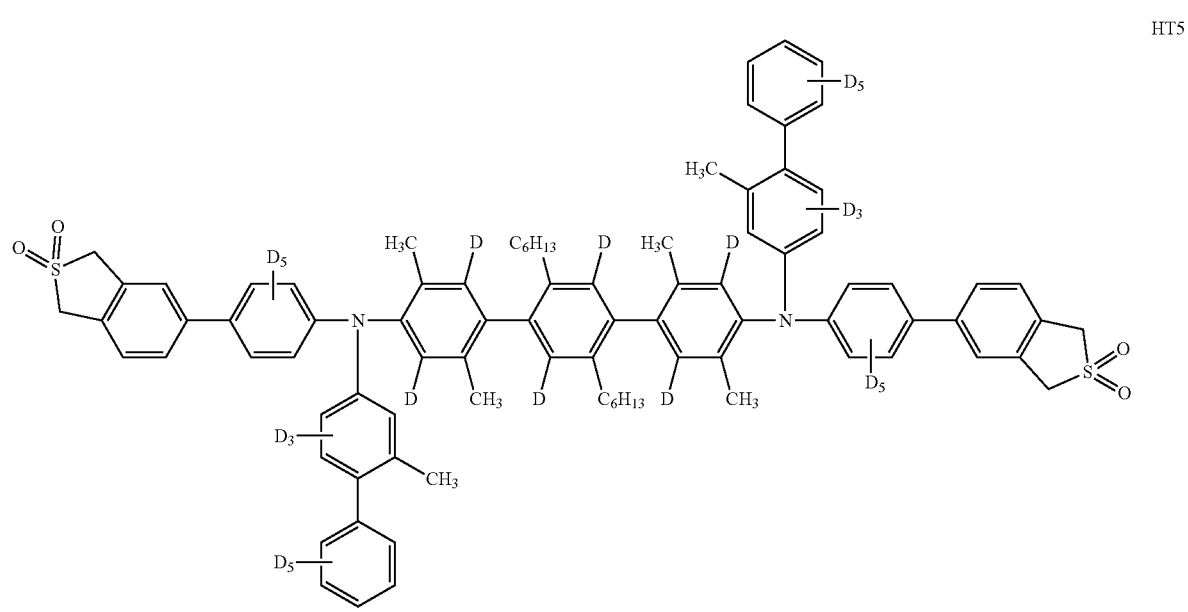
HT5

-continued
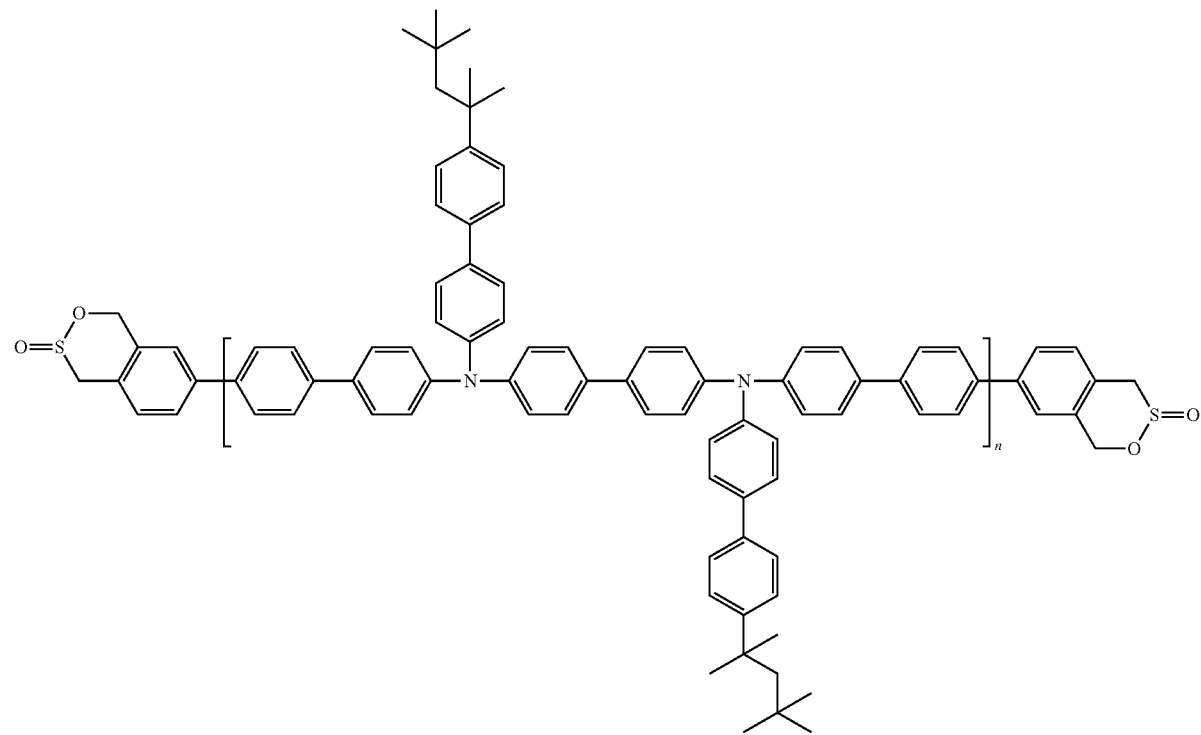
HT6
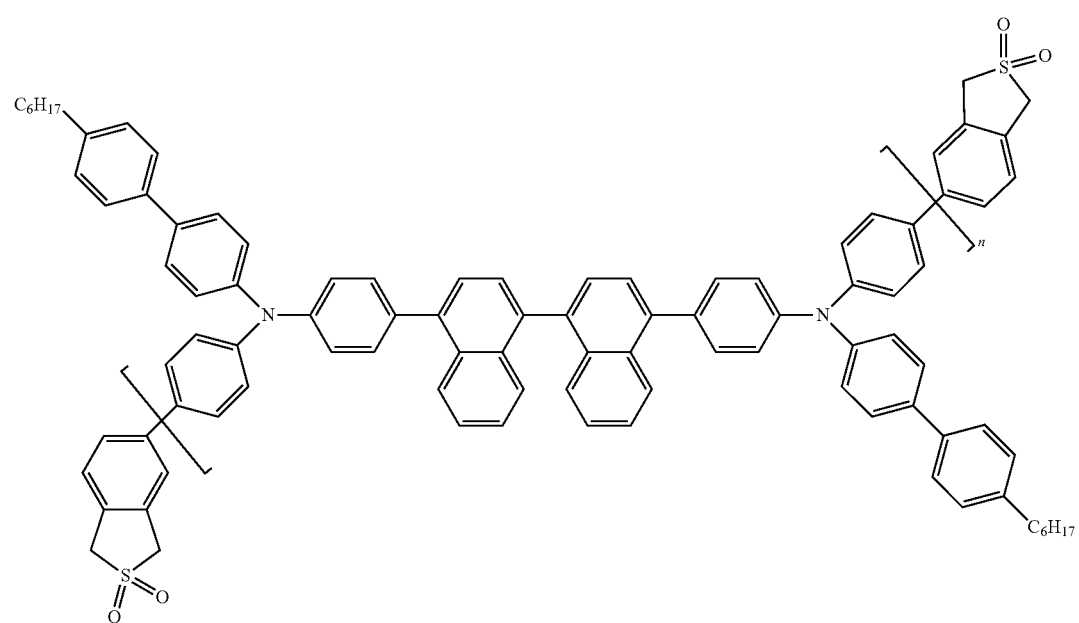
HT7

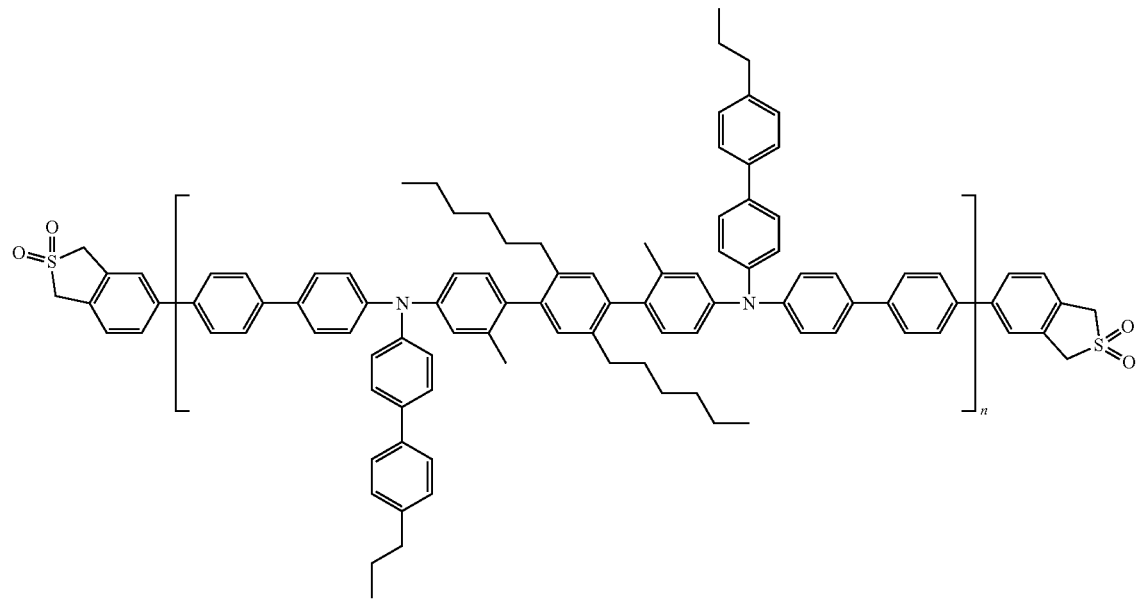
HT8
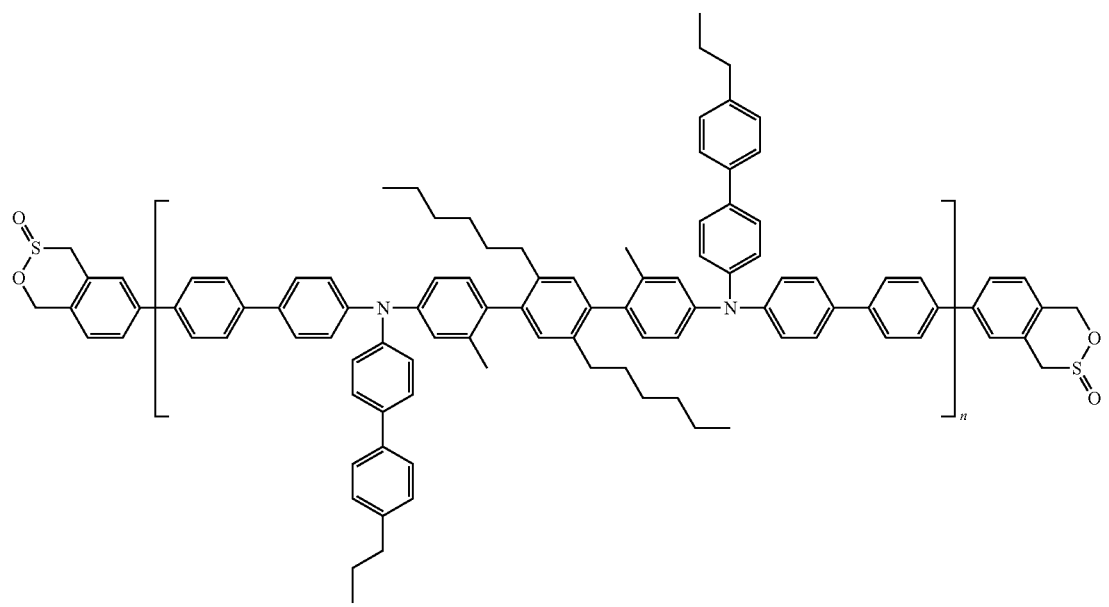
HT9

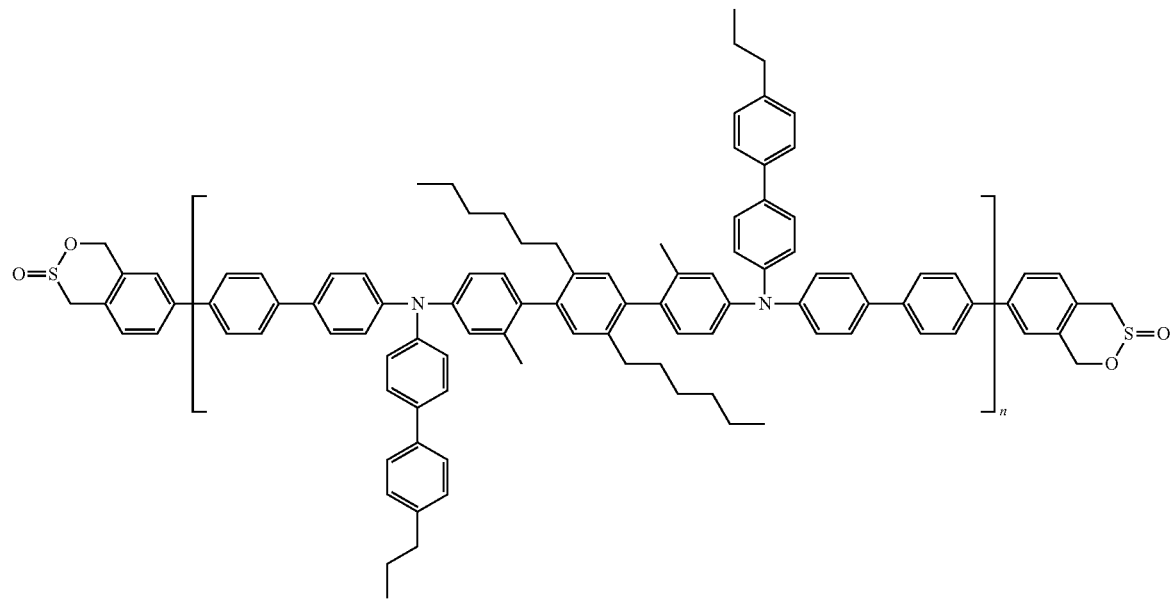
HT10
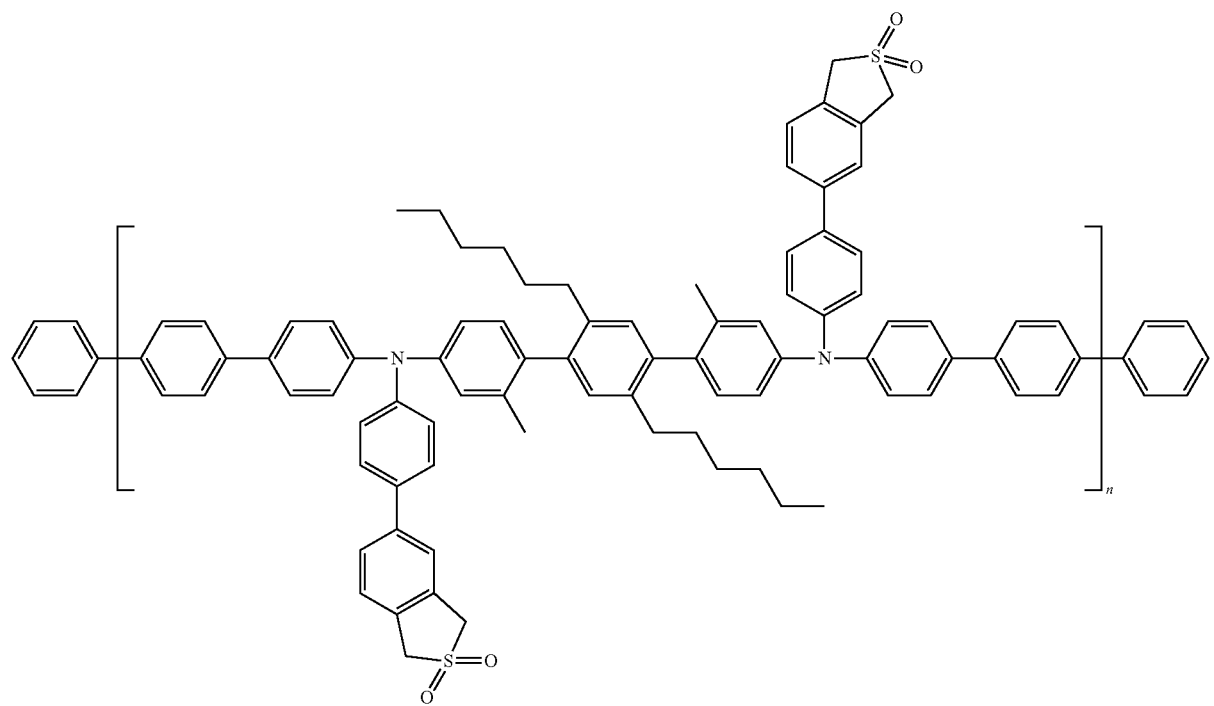
HT12

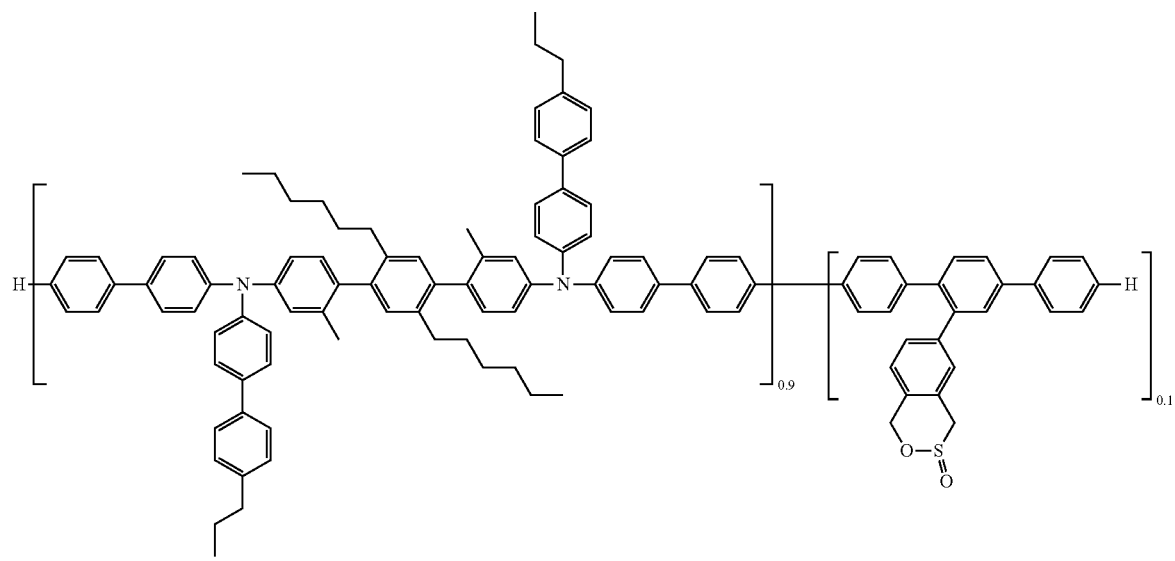
HT13
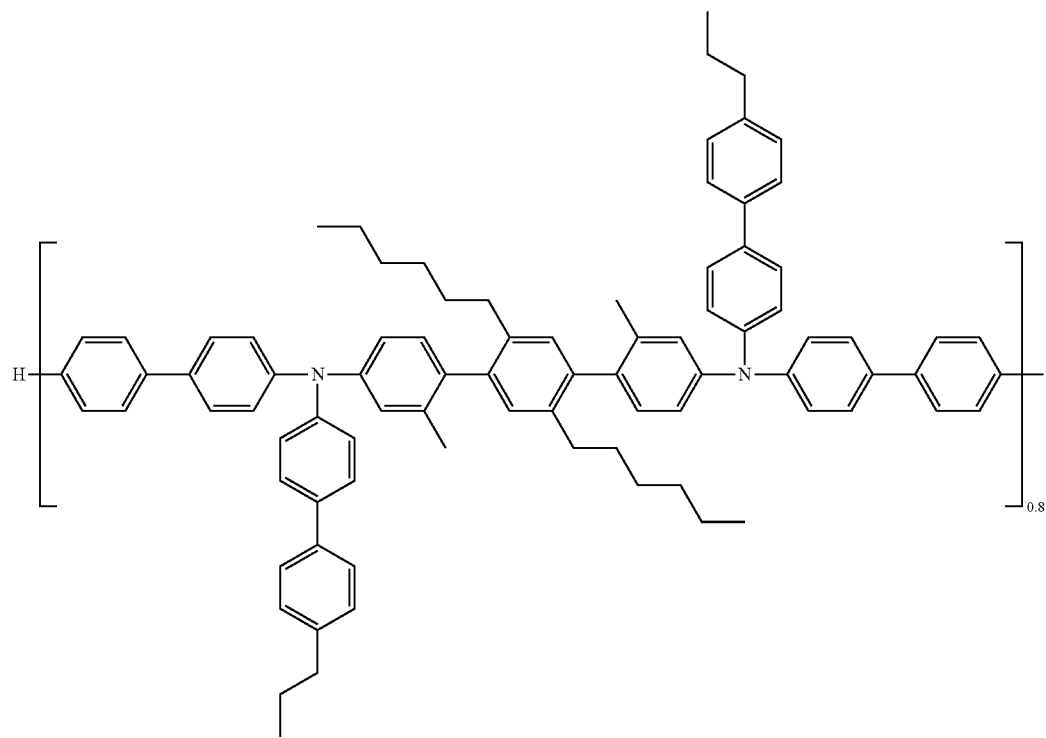
HT14

-continued
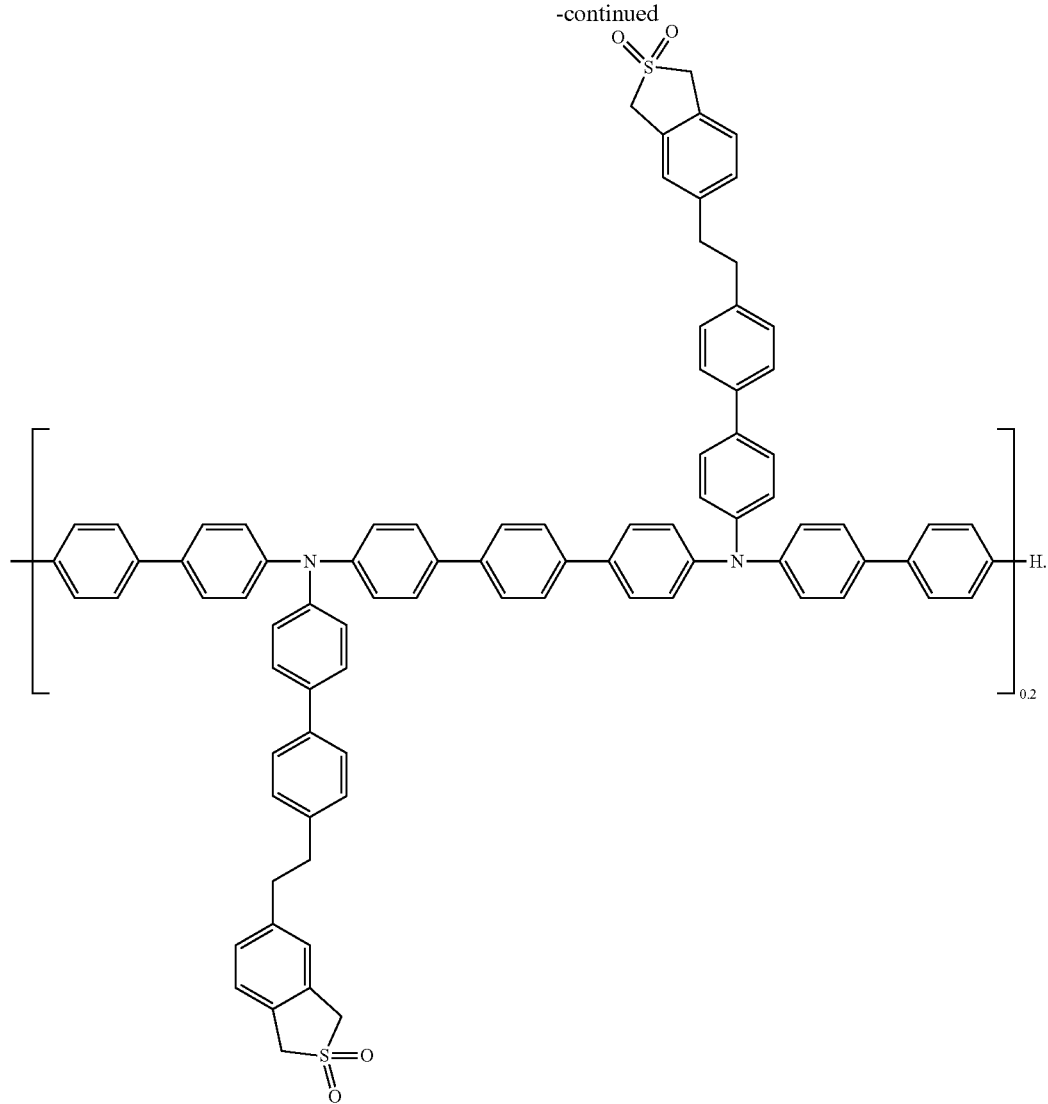
where n ≥ 20.
* * * * *